United States Patent
Griffioen et al.

(10) Patent No.: US 9,023,852 B2
(45) Date of Patent: May 5, 2015

(54) 1, 2, 4-THIADIAZOL-5-YLPIPERAZINE DERIVATIVES USEFUL IN THE TREATMENT OF NEURODEGENERATIVE DISEASES

(75) Inventors: Gerard Griffioen, Linden (BE); Matthias Nettekoven, Grenzach-Wyhlen (DE); Katrien Princen, Heverlee (BE); Hasane Ratni, Habsheim (FR); Walter Vifian, Gelterkinden (CH)

(73) Assignee: Remynd NV, Heverlee (BE)

( * ) Notice: Subject to any disclaimer, the term of this patent is extended or adjusted under 35 U.S.C. 154(b) by 0 days.

(21) Appl. No.: 14/127,779

(22) PCT Filed: Jun. 29, 2012

(86) PCT No.: PCT/EP2012/062778
§ 371 (c)(1),
(2), (4) Date: Dec. 19, 2013

(87) PCT Pub. No.: WO2013/004642
PCT Pub. Date: Jan. 10, 2013

(65) Prior Publication Data
US 2014/0128404 A1    May 8, 2014

(30) Foreign Application Priority Data
Jul. 1, 2011   (EP) ..................................... 11172324

(51) Int. Cl.
| | | |
|---|---|---|
| *A61K 31/497* | (2006.01) | |
| *C07D 413/00* | (2006.01) | |
| *C07D 417/00* | (2006.01) | |
| *C07D 419/00* | (2006.01) | |
| *C07D 285/135* | (2006.01) | |
| *C07D 285/08* | (2006.01) | |
| *C07D 417/04* | (2006.01) | |
| *C07D 417/12* | (2006.01) | |
| *C07D 417/14* | (2006.01) | |

(52) U.S. Cl.
CPC .......... *C07D 285/135* (2013.01); *C07D 285/08* (2013.01); *C07D 417/04* (2013.01); *C07D 417/12* (2013.01); *C07D 417/14* (2013.01)

(58) Field of Classification Search
USPC ..................................... 514/252.11; 544/367
See application file for complete search history.

(56) References Cited

FOREIGN PATENT DOCUMENTS

WO    2007090617 A2    8/2007

OTHER PUBLICATIONS

Written Opinion of the International Searching Authority for International Application No. PCT/EP2012/062778, dated Jan. 1, 2014 (4 pages).

*Primary Examiner* — Marcos Sznaidman
(74) *Attorney, Agent, or Firm* — Lathrop & Gage LLP; James H. Velema, Esq.

(57) ABSTRACT

The present invention relates to a compound of formula (IA) The present invention also relates to the use of the compound of formula IA for treating certain neurodegenerative disorders characterized by cytotoxic TAU misfolding and/or aggregation.

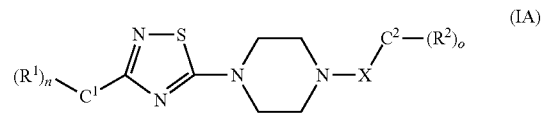

22 Claims, No Drawings

1, 2, 4-THIADIAZOL-5-YLPIPERAZINE DERIVATIVES USEFUL IN THE TREATMENT OF NEURODEGENERATIVE DISEASES

RELATED APPLICATIONS

This application is a 35 U.S.C. §371 filing of International Application No. PCT/EP2012/062778, filed Jun. 29, 2012; which claims priority to European Patent Application No. 11172324.3, filed on Jul. 1, 2011. The entire contents of each are incorporated herein by reference.

FIELD OF THE INVENTION

The present invention relates to arylthiadiazoles and their use for treating certain neurodegenerative disorders characterized by cytotoxic TAU misfolding and/or aggregation.

BACKGROUND OF THE INVENTION

TAU is a protein with the ability to bind- and consequently stabilise and define-microtubule structure and function in neurons. The binding of TAU to microtubules is regulated by phosphorylation of TAU; several TAU phosphorylation sites and their corresponding kinases have been identified which control phosphorylation status of TAU and consequently modulate the affinity of TAU-binding to microtubules.

Tauopathies are characterised by insoluble aggregates or polymers of hyperphosphorylated TAU which are formed by self-polymerisation of TAU monomers.

An important aspect of the TAU aggregation is its associated cytotoxicity, which reduces neuronal integrity and functionality and ultimately resulting in disease symptoms. A direct role of TAU in disease onset has been established unequivocally by the elucidation of familial mutations in TAU, which appear to be responsible for a very early and sometimes aggressive form of tauopathy. Such mutations comprise changes in the amino acid sequence of TAU that—directly or indirectly promote neurotoxic aggregation.

Alzheimer's disease is the best known of these, where TAU protein is deposited within neurons in the form of neurofibrillary tangles (NFTs). They were first described by the eponymous Alois Alzheimer in one of his patients suffering from the disorder.

Currently used treatments for tauopathies, including Alzheimer's disease, offer only symptomatic benefit without impacting the underlying neurodegeneration.

WO2007/090617 discloses substituted 1,2,4-thiadiazole derivatives for use in the treatment of an α-synucleopathy such as Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease.

Treatments aimed to suppress cytotoxic TAU misfolding and/or aggregation, in order to delay or halt the progression of disease, are presently not available. Thus there is a need for new treatments that target the underlying molecular mechanism of noxious TAU misfolding and/or aggregation in order to reduce neuronal cell death and/or degeneration in patients suffering from tauopathies such as Alzheimer's disease (AD).

SUMMARY OF THE INVENTION

A first aspect of the present invention relates to compounds of formula IA

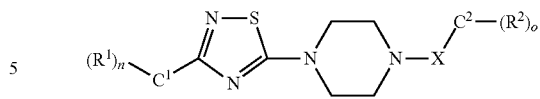

wherein $R^1$ is hydrogen; lower alkyl; lower alkyl substituted by halogen; halogen; lower alkoxy; lower alkoxy substituted by halogen; or cyano;

$R^2$ is hydrogen; lower alkyl; lower alkyl substituted by halogen; halogen; lower alkoxy; or is lower alkoxy substituted by halogen;

$C^1$ is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl;

$C^2$ is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl;

X is —CH—; —CH$_2$—CHR—; —CH$_2$—CH$_2$—CH$_2$—; —CH$_2$C(O)—; —CHR'—CH$_2$—;

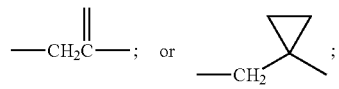

R is hydrogen; hydroxyl; halogen or lower alkyl;

R' is lower alkyl;

n is 1 or 2; if n is 2, $R^1$ may be independently selected from each other;

o is 1 or 2; if o is 2, $R^2$ may be independently selected from each other;

or to a pharmaceutically active salt thereof to a stereoisomeric form, including an individual diastereoisomer or enantiomer of the compound of formula IA as well as to a racemic or non-racemic mixture thereof.

A second aspect of the invention relates to a process for preparation of compounds of formula AI according to a first aspect of the invention, which process comprises coupling a compound of formula

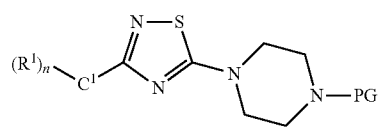

with a compound of formula

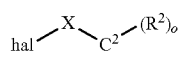

to give a compound of formula

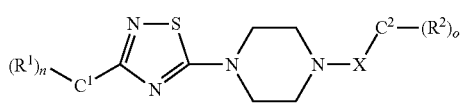

wherein the definitions are as described in the first aspect of the invention, wherein PG is hydrogen or a protecting group, wherein hal is a halogen or if desired, converting the compounds obtained into pharmaceutically acceptable acid addition salts.

A third aspect of the invention relates to a medicament containing one or more compounds according to the first aspect of the invention and pharmaceutically acceptable excipients.

A fourth aspect of the invention relates to a medicament according to the third aspect, for use in the treatment of a disease selected from the group consisting of are Alzheimer's disease, Pick's disease, corticobasal degeneration, progressive supranuclear palsy, frontotemporal dementia, and parkinsonism (linked to chromosome 17, FTDP-17).

A fifth aspect of the invention relates to the use of a compound according to the first aspect of the invention for the manufacture of medicaments for the treatment of Alzheimer's disease, Pick's disease, corticobasal degeneration, progressive supranuclear palsy, frontotemporal dementia and parkinsonism (linked to chromosome 17, FTDP-17).

A sixth aspect of the invention relates to a method for the treatment of Alzheimer's disease, Pick's disease, corticobasal degeneration, progressive supranuclear palsy, frontotemporal dementia and parkinsonism (linked to chromosome 17, FTDP-17), which method comprising administering an effective amount of a compound as defined in the first aspect of the invention.

DETAILED DESCRIPTION

In an embodiment, the present invention encompasses a compound of formula IA, wherein, $R^1$ is hydrogen; lower alkyl; lower alkyl substituted by halogen; halogen; lower alkoxy; lower alkoxy substituted by halogen; or is cyano; preferably $R^1$ is lower alkyl substituted by halogen; halogen; or lower alkoxy; preferably $R^1$ is lower alkyl substituted by halogen; or halogen;

$R^2$ is hydrogen; lower alkyl; lower alkyl substituted by halogen; halogen; lower alkoxy; or is lower alkoxy substituted by halogen; preferably $R^2$ is hydrogen; lower alkyl; halogen; or is lower alkoxy; preferably $R^2$ is hydrogen; halogen; or is lower alkoxy;

$C_1$ is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl; preferably $C_1$ is phenyl; pyridine-2-yl; pyridine-3-yl; pyridine-4-yl; thiophen-2-yl; pyrazine-2-yl; pyridazin-4-yl; pyrimidin-5-yl; piperidin-lyl; or tetrahydro-2H-pyran-4-yl; preferably $C_1$ is phenyl; pyridine-2-yl; pyridine-3-yl; pyridine-4-yl; pyrazine-2-yl; pyridazin-4-yl; pyrimidin-5-yl; or piperidin-lyl; preferably $C_1$ is phenyl; pyridine-3-yl; pyridine-4-yl; pyrazine-2-yl; pyridazin-4-yl; or piperidin-lyl; preferably $C_1$ is phenyl; pyridine-3-yl; pyridine-4-yl; or pyridazin-4-yl; preferably $C_1$ is phenyl; or pyridine-3-yl;

$C_2$ is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl; preferably $C_2$ is phenyl; pyridine-2-yl; pyridine-3-yl; pyridine-4-yl; pyrazine-2-yl; pyridazin-4-yl; pyrimidin-5-yl; piperidin-lyl; tetrahydro-2H-pyran-4-yl; or cycloalkyl; preferably $C_2$ is phenyl; pyridine-2-yl; pyridine-3-yl; pyridine-4-yl; piperidin-lyl; tetrahydro-2H-pyran-4-yl; or cycloalkyl; preferably $C_2$ is phenyl; pyridine-3-yl; pyridine-4-yl; or tetrahydro-2H-pyran-4-yl; preferably $C_2$ is phenyl; pyridine-3-yl; pyridine-4-yl; or tetrahydro-2H-pyran-4-yl;

X is —CH$_2$—; —CH$_2$—CHR—; —CH$_2$—CH$_2$—CH$_2$—; —CH$_2$C(O)—; —CHR'—CH$_2$—;

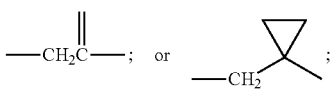

preferably X is —CH$_2$—; —CH$_2$—CHR—; —CH$_2$—CH$_2$—CH$_2$—; —CHR'—CH$_2$—; or

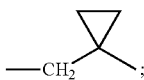

preferably X is —CH$_2$—; —CH$_2$—CHR—; —CH$_2$—CH$_2$—CH$_2$—; or —CHR'—CH$_2$—; preferably X is —CH$_2$—; —CH$_2$—CHR—; or —CHR'—CH$_2$—;

R is hydrogen; hydroxyl; halogen or lower alkyl; preferably R is hydrogen; halogen or lower alkyl; preferably R is hydrogen or halogen;

n is 1 or 2; if n is 2, $R^1$ may be independently from each other; preferably n is 1;

o is 1 or 2; if o is 2, $R^2$ may be independently from each other; preferably o is 1.

In an embodiment, the invention provides compounds of formula IA wherein $R^1$ is hydrogen; $C_{1-6}$alkyl; $C_{1-6}$alkyl substituted by halogen; halogen; lower alkoxy; $C_{1-6}$alkoxy substituted by halogen; or is cyano; preferably $R^1$ is $C_{1-6}$alkyl substituted by halogen; halogen; or $C_{1-6}$alkoxy; preferably $R^1$ is $C_{1-6}$alkyl substituted by halogen; or halogen;

$R^2$ is hydrogen; $C_{1-6}$alkyl; $C_{1-6}$alkyl substituted by halogen; $C_{1-6}$alkoxy; or is $C_{1-6}$alkoxy substituted by halogen; preferably $R^2$ is hydrogen; $C_{1-6}$alkyl; halogen; or is $C_{1-6}$alkoxy; preferably $R^2$ is hydrogen; halogen; or is $C_{1-6}$alkoxy;

$C_1$ is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl; preferably $C_1$ is phenyl; pyridine-2-yl; pyridine-3-yl; pyridine-4-yl; thiophen-2-yl; pyrazine-2-yl; pyridazin-4-yl; pyrimidin-5-yl; piperidin-lyl; or tetrahydro-2H-pyran-4-yl; preferably $C_1$ is phenyl; pyridine-2-yl; pyridine-3-yl; pyridine-4-yl; pyrazine-2-yl; pyridazin-4-yl; pyrimidin-5-yl; or piperidin-lyl; preferably $C_1$ is phenyl; pyridine-3-yl; pyridine-4-yl; pyrazine-2-yl; pyridazin-4-yl; or piperidin-lyl; preferably $C_1$ is phenyl; pyridine-3-yl; pyridine-4-yl; or pyridazin-4-yl; preferably $C_1$ is phenyl; or pyridine-3-yl;

$C_2$ is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl; preferably $C_2$ is phenyl; pyridine-2-yl; pyridine-3-yl; pyridine-4-yl; pyrazine-2-yl; pyridazin-4-yl; pyrimidin-5-yl; piperidin-lyl; tetrahydro-2H-pyran-4-yl; or cycloalkyl; preferably $C_2$ is phenyl; pyridine-2-yl; pyridine-3-yl; pyridine-4-yl; piperidin-lyl; tetrahydro-2H-pyran-4-yl; or cycloalkyl; preferably $C_2$ is phenyl; pyridine-3-yl; pyridine- 4-yl; or tetrahydro-2H-pyran-4-yl; preferably $C^2$ is phenyl; pyridine-3-yl; pyridine-4-yl; or tetrahydro-2H-pyran-4-yl;

X is —$CH_2$—; —$CH_2$—CHR—; —$CH_2$—$CH_2$—$CH_2$—; —$CH_2$C(O)—; —CHR'—$CH_2$—;

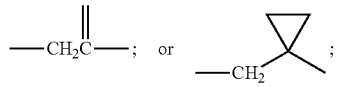

preferably X is —$CH_2$—; —$CH_2$—CHR—; —$CH_2$—$CH_2$—$CH_2$—; —CHR'—$CH_2$—; or

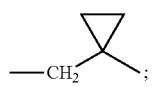

preferably X is —$CH_2$—; —$CH_2$—CHR—; —$CH_2$—$CH_2$—$CH_2$—; or —CHR'—$CH_2$—; preferably X is —$CH_2$—; —$CH_2$—CHR—; or —CHR'—$CH_2$—;

R is hydrogen; hydroxyl; halogen or $C_{1-6}$alkyl; preferably R is hydrogen; halogen or $C_{1-6}$alkyl; preferably R is hydrogen or halogen;

n is 1 or 2; if n is 2, $R^1$ may be independently from each other; preferably n is 1;

o is 1 or 2; if o is 2, $R^2$ may be independently from each other; preferably o is 1.

In another particular embodiment of the present invention, the compounds have a structure according to formula IA, wherein $C^1$ is selected from: phenyl; pyridine-2-yl; pyridine-3-yl; pyridine-4-yl; pyrazine-2-yl; pyridazin-4-yl; or pyrimidin-5-yl.

In another particular embodiment of the present invention, the compounds have a structure according to formula IA, wherein $C^2$ is selected from: phenyl; pyridine-2-yl; pyridine-3-yl; pyridine-4-yl; pyrazine-2-yl; tetrahydro-2H-pyran-4-yl; or cycloalkyl.

In a particular embodiment of the invention, the compounds have a structure of formula IA, whereby $C^1$ is pyridine-2-yl; pyridine-3-yl; or pyridine-4-yl; and $C^2$ is phenyl; yet more in particular $C^1$ is pyridine-3-yl; or pyridine-4-yl; yet more in particular $C^1$ is pyridine-3-yl.

In another particular embodiment of the present invention, the compounds have a structure according to formula IA, wherein $C^1$ is phenyl and $C^2$ is phenyl.

In another particular embodiment of the present invention, the compounds have a structure according to formula IA, wherein $C^1$ is phenyl; $C^2$ is phenyl and n is 1.

In another particular embodiment of the present invention, the compounds have a structure according to formula IA, wherein $C^1$ is phenyl; $C^2$ is phenyl and n is 2.

In another particular embodiment of the present invention, the compounds have a structure according to formula IA, wherein $C^1$ is phenyl; $C^2$ is phenyl and o is 1.

In another particular embodiment of the present invention, the compounds have a structure according to formula IA, wherein $C^1$ is phenyl; $C^2$ is phenyl and o is 2.

In another particular embodiment of the present invention, the compounds have a structure according to formula IA, wherein $C^1$ is phenyl and $C^2$ is tetrahydro-2H-pyran-4-yl.

In a particular embodiment of the invention, the compounds have a structure of formula IA, whereby $C^1$ is pyridine-2-yl; pyridine-3-yl; or pyridine-4-yl; and $C^2$ is tetrahydro-2H-pyran-4-yl; yet more in particular $C^1$ is pyridine-3-yl; or pyridine-4-yl; yet more in particular $C^1$ is pyridine-3-yl.

In a particular embodiment of the invention, the compounds have a structure of formula IA, whereby $C^1$ is phenyl; and $C^2$ is pyridine-2-yl; pyridine-3-yl; or pyridine-4-yl; yet more in particular $C^2$ is pyridine-3-yl; or pyridine-4-yl; yet more in particular $C^2$ is pyridine-3-yl.

In another particular embodiment of the present invention, the compounds have a structure according to formula IA, wherein $C^1$ is pyridazin-4-yl and $C^2$ is phenyl.

In a particular embodiment of the invention, the compounds have a structure of formula IA, whereby $C^1$ is pyridine-2-yl; pyridine-3-yl; or pyridine-4-yl; and $C^2$ is pyridine-3-yl; yet more in particular $C^1$ is pyridine-3-yl; or pyridine-4-yl; yet more in particular $C^1$ is pyridine-3-yl.

In a particular embodiment of the invention, the compounds have a structure of formula IA, whereby $C^1$ is pyridine-2-yl; pyridine-3-yl; or pyridine-4-yl; and $C^2$ is pyridine-4-yl; yet more in particular $C^1$ is pyridine-3-yl; or pyridine-4-yl; yet more in particular $C^1$ is pyridine-3-yl.

In a particular embodiment of the invention, the compounds have a structure of formula IA, whereby $C^1$ is pyridine-3-yl; and $C^2$ is pyridine-2-yl; pyridine-3-yl; or pyridine-4-yl; yet more in particular $C^2$ is pyridine-3-yl; or pyridine-4-yl; yet more in particular $C^2$ is pyridine-3-yl.

In a particular embodiment of the invention, the compounds have a structure of formula IA, whereby $C^1$ is pyridine-4-yl; and $C^2$ is pyridine-2-yl; pyridine-3-yl; or pyridine-4-yl; yet more in particular $C^2$ is pyridine-3-yl; or pyridine-4-yl; yet more in particular $C^2$ is pyridine-3-yl.

In a particular embodiment, the present invention relates to the following compounds, uses, medicaments and processes:

E1. A compound of formula I

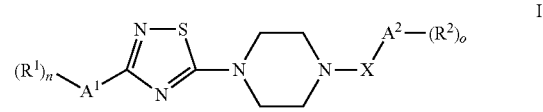

wherein $R^1$ is hydrogen; lower alkyl; lower alkyl substituted by halogen; halogen; lower alkoxy; lower alkoxy substituted by halogen; or cyano;

$R^2$ is hydrogen; lower alkyl; lower alkyl substituted by halogen; halogen; lower alkoxy; or is lower alkoxy substituted by halogen;

$A^1$ is phenyl; benzo[1,3]dioxol; pyridine-2-yl; pyridine-3-yl; pyridine-4-yl; thiophen-2-yl; pyrazine-2-yl; or cycloalkyl;

$A^2$ is phenyl; benzo[1,3]dioxol; pyridine-2-yl; pyridine-3-yl; pyridine-4-yl; thiophen-2-yl; pyrazine-2-yl; or cycloalkyl;

X is a bond; —$CH_2$—; —$CH_2$—CHR—; —$CH_2$—$CH_2$—$CH_2$—; —$CH_2$C(O)—; —C(O)NH—; —CHR'—$CH_2$—;

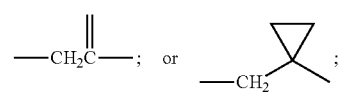

preferably is —$CH_2$—; —$CH_2$—CHR—; —$CH_2$—$CH_2$—$CH_2$—; —$CH_2$C(O)—; —CHR'—$CH_2$—;

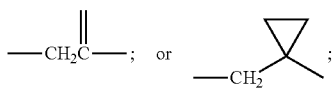

R is hydrogen; hydroxyl; halogen; or lower alkyl;
R' is lower alkyl;
n is 1 or 2; if n is 2, $R^1$ may be independently from each other;
o is 1 or 2; if o is 2, $R^2$ may be independently from each other;
or a pharmaceutically active salt thereof, a stereoisomeric form, including an individual diastereoisomer or enantiomer of the compound of formula (I) as well as a racemic or non-racemic mixture thereof.

E2. A compound of formula I according to E1, wherein $A^1$ and $A^2$ are both phenyl.

E3. Compound of formula I according to E2, which compounds are
1-(2,4-Dichloro-benzyl)-4-(3-p-tolyl-[1,2,4]thiadiazol-5-yl)-piperazine
1-Phenethyl-4-(3-p-tolyl-[1,2,4]thiadiazol-5-yl)-piperazine
1-[2-(3,4-Dichloro-phenyl)-ethyl]-4-(3-p-tolyl-[1,2,4]thiadiazol-5-yl)-piperazine
1-(2-Methyl-benzyl)-4-(3-p-tolyl-[1,2,4]thiadiazol-5-yl)-piperazine
1-[3-(4-Chloro-phenyl)-[1,2,4]thiadiazol-5-yl]-4-(2-methyl-benzyl)-piperazine
1-[3-(3-Methoxy-phenyl)-[1,2,4]thiadiazol-5-yl]-4-(2-methyl-benzyl)-piperazine
1-[3-(4-Chloro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(3-methoxy-phenyl)-[1,2,4]thiadiazol-5-yl]-piperazine
1-[2-(3-Methoxy-phenyl)-ethyl]-4-(3-p-tolyl-[1,2,4]thiadiazol-5-yl)-piperazine
1-[3-(4-Chloro-phenyl)-[1,2,4]thiadiazol-5-yl]-4-[2-(4-methoxy-phenyl)-ethyl]-piperazine
1-[2-(4-Methoxy-phenyl)-ethyl]-4-[3-(3-methoxy-phenyl)-[1,2,4]thiadiazol-5-yl]-piperazine
1-[2-(4-Methoxy-phenyl)-ethyl]-4-(3-p-tolyl-[1,2,4]thiadiazol-5-yl)-piperazine
1-[3-(4-Chloro-phenyl)-[1,2,4]thiadiazol-5-yl]-4-[2-(3-fluoro-phenyl)-ethyl]-piperazine
1-[2-(3-Chloro-phenyl)-ethyl]-4-[3-(4-chloro-phenyl)-[1,2,4]thiadiazol-5-yl]-piperazine
1-[3-(4-Chloro-phenyl)-[1,2,4]thiadiazol-5-yl]-4-(2-m-tolyl-ethyl)-piperazine
1-[3-(4-Chloro-phenyl)-[1,2,4]thiadiazol-5-yl]-4-[2-(4-fluoro-phenyl)-ethyl]-piperazine
1-[2-(4-Chloro-phenyl)-ethyl]-4-[3-(4-chloro-phenyl)-[1,2,4]thiadiazol-5-yl]-piperazine
1-[3-(4-Chloro-phenyl)-[1,2,4]thiadiazol-5-yl]-4-(2-p-tolyl-ethyl)-piperazine
1-[3-(4-Chloro-phenyl)-[1,2,4]thiadiazol-5-yl]-4-[2-(2-methoxy-phenyl)-ethyl]-piperazine
1-[3-(4-Chloro-phenyl)-[1,2,4]thiadiazol-5-yl]-4-[2-(2-fluoro-phenyl)-ethyl]-piperazine
1-[2-(2-Chloro-phenyl)-ethyl]-4-[3-(4-chloro-phenyl)-[1,2,4]thiadiazol-5-yl]-piperazine
1-[3-(3,5-Dichloro-phenyl)-[1,2,4]thiadiazol-5-yl]-4-[2-(3-methoxy-phenyl)-ethyl]-piperazine
1-[3-(4-Chloro-phenyl)-[1,2,4]thiadiazol-5-yl]-4-[3-(3-methoxy-phenyl)-propyl]-piperazine
1-[3-(4-Fluoro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(2-methoxy-phenyl)-[1,2,4]thiadiazol-5-yl]-piperazine
1-[2-(3-Methoxy-phenyl)-ethyl]-4-[3-(4-trifluoromethoxy-phenyl)-[1,2,4]thiadiazol-5-yl]-piperazine
1-[2-(4-Methoxy-phenyl)-ethyl]-4-[3-(4-trifluoromethoxy-phenyl)-[1,2,4]thiadiazol-5-yl]-piperazine
1-[3-(4-Chloro-phenyl)-[1,2,4]thiadiazol-5-yl]-4-[2-(3-trifluoromethoxy-phenyl)-ethyl]-piperazine
1-[3-(4-Chloro-phenyl)-[1,2,4]thiadiazol-5-yl]-4-[3-(2-methoxy-phenyl)-propyl]-piperazine
1-[2-(4-Methoxy-phenyl)-ethyl]-4-[3-(4-methoxy-phenyl)-[1,2,4]thiadiazol-5-yl]-piperazine
1-[3-(3-Chloro-phenyl)-[1,2,4]thiadiazol-5-yl]-4-[2-(4-methoxy-phenyl)-ethyl]-piperazine
1-[2-(4-Methoxy-phenyl)-ethyl]-4-[3-(2-methoxy-phenyl)-[1,2,4]thiadiazol-5-yl]-piperazine
1-[3-(3,5-Dichloro-phenyl)-[1,2,4]thiadiazol-5-yl]-4-[2-(4-methoxy-phenyl)-ethyl]-piperazine
1-[3-(4-Fluoro-phenyl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(4-methoxy-phenyl)-[1,2,4]thiadiazol-5-yl]-piperazine
1-[3-(4-Chloro-phenyl)-[1,2,4]thiadiazol-5-yl]-4-[2-(4-ethoxy-phenyl)-ethyl]-piperazine
1-[3-(4-Chloro-phenyl)-[1,2,4]thiadiazol-5-yl]-4-[2-(3-isopropoxy-phenyl)-ethyl]-piperazine
1-[3-(4-Chloro-phenyl)-[1,2,4]thiadiazol-5-yl]-4-[3-(4-methoxy-phenyl)-propyl]-piperazine
2-{4-[3-(4-Chloro-phenyl)-[1,2,4]thiadiazol-5-yl]-piperazin-1-yl}-1-(4-methoxy-phenyl)-ethanone
2-{4-[3-(4-Chloro-phenyl)-[1,2,4]thiadiazol-5-yl]-piperazin-1-yl}-1-(4-methoxy-phenyl)-ethanol
1-[3-(4-Chloro-2-fluoro-phenyl)-[1,2,4]thiadiazol-5-yl]-4-[2-(3-methoxy-phenyl)-ethyl]-piperazine
1-[3-(4-Chloro-2-fluoro-phenyl)-[1,2,4]thiadiazol-5-yl]-4-[2-(4-methoxy-phenyl)-ethyl]-piperazine
1-[3-(2-Chloro-phenyl)-[1,2,4]thiadiazol-5-yl]-4-[2-(3-methoxy-phenyl)-ethyl]-piperazine
1-[3-(2-Chloro-phenyl)-[1,2,4]thiadiazol-5-yl]-4-[2-(4-methoxy-phenyl)-ethyl]-piperazine
1-[3-(4-Chloro-phenyl)-[1,2,4]thiadiazol-5-yl]-4-[2-(4-methoxy-phenyl)-allyl]-piperazine
2-{4-[3-(4-Chloro-phenyl)-[1,2,4]thiadiazol-5-yl]-piperazin-1-yl}-1-(3-methoxy-phenyl)-ethanone
2-{4-[3-(4-Chloro-phenyl)-[1,2,4]thiadiazol-5-yl]-piperazin-1-yl}-1-(3-methoxy-phenyl)-ethanol
2-{4-[3-(4-Chloro-phenyl)-[1,2,4]thiadiazol-5-yl]-piperazin-1-yl}-1-(3-fluoro-phenyl)-ethanone
2-{4-[3-(4-Chloro-phenyl)-[1,2,4]thiadiazol-5-yl]-piperazin-1-yl}-1-(3-fluoro-phenyl)-ethanol
1-[3-(4-Chloro-phenyl)-[1,2,4]thiadiazol-5-yl]-4-[2-fluoro-2-(4-methoxy-phenyl)-ethyl]-piperazine
1-[3-(4-Chloro-phenyl)-[1,2,4]thiadiazol-5-yl]-4-[2-fluoro-2-(3-methoxy-phenyl)-ethyl]-piperazine
1-[3-(4-Fluoro-2-methoxy-phenyl)-[1,2,4]thiadiazol-5-yl]-4-[2-(3-methoxy-phenyl)-ethyl]-piperazine
1-[3-(4-Fluoro-2-methoxy-phenyl)-[1,2,4]thiadiazol-5-yl]-4-[2-(4-methoxy-phenyl)-ethyl]-piperazine
1-[1-(4-Chloro-phenyl)-cyclopropylmethyl]-4-[3-(4-chloro-phenyl)-[1,2,4]thiadiazol-5-yl]-piperazine
1-[3-(4-Chloro-phenyl)-[1,2,4]thiadiazol-5-yl]-4-[2-(3-difluoromethoxy-phenyl)-ethyl]-piperazine
1-[3-(4-Chloro-phenyl)-[1,2,4]thiadiazol-5-yl]-4-[2-(4-difluoromethoxy-phenyl)-ethyl]-piperazine
1-[3-(4-Chloro-phenyl)-[1,2,4]thiadiazol-5-yl]-4-[2-(4-isopropoxy-phenyl)-ethyl]-piperazine 1-[3-(4-Chloro-phenyl)-[1,2,4]thiadiazol-5-yl]-4-[2-(4-methoxy-phenyl)-propyl]-piperazine
1-[3-(4-Chloro-phenyl)-[1,2,4]thiadiazol-5-yl]-4-[2-(4-methoxy-phenyl)-1-methyl-ethyl]-piperazine
4-(5-{4-[2-(4-Methoxy-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(3-fluoro-4-methoxy-phenyl)-ethyl]-piperazine
3-(5-{4-[2-(4-Methoxy-phenyl)-ethyl]-piperazin-1-yl}-[1,2,4]thiadiazol-3-yl)-benzonitrile
1-[3-(3-Chloro-phenyl)-[1,2,4]thiadiazol-5-yl]-4-phenethyl-piperazine
1-[3-(3-Fluoro-phenyl)-[1,2,4]thiadiazol-5-yl]-4-phenethyl-piperazine
1-[3-(3-Fluoro-phenyl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(4-fluoro-phenyl)-ethyl]-piperazine
1-[2-(4-Fluoro-phenyl)-ethyl]-4-[3-(3-fluoro-phenyl)-[1,2,4]thiadiazol-5-yl]-piperazine
1-[2-(4-Chloro-phenyl)-ethyl]-4-[3-(3-chloro-phenyl)-[1,2,4]thiadiazol-5-yl]-piperazine
1-[2-(4-Chloro-phenyl)-ethyl]-4-[3-(3-fluoro-phenyl)-[1,2,4]thiadiazol-5-yl]-piperazine
1-[3-(3-Chloro-phenyl)-[1,2,4]thiadiazol-5-yl]-4-(2-methyl-benzyl)-piperazine
1-[3-(3-Fluoro-phenyl)-[1,2,4]thiadiazol-5-yl]-4-(2-methyl-benzyl)-piperazine
1-[3-(3,4-Difluoro-phenyl)-[1,2,4]thiadiazol-5-yl]-4-phenethyl-piperazine
1-[3-(3,4-Difluoro-phenyl)-[1,2,4]thiadiazol-5-yl]-4-[2-(4-methoxy-phenyl)-ethyl]-piperazine
1-[3-(3,4-Difluoro-phenyl)-[1,2,4]thiadiazol-5-yl]-4-[2-(4-fluoro-phenyl)-ethyl]-piperazine
1-[2-(4-Chloro-phenyl)-ethyl]-4-[3-(3,4-difluoro-phenyl)-[1,2,4]thiadiazol-5-yl]-piperazine
1-[3-(3,4-Difluoro-phenyl)-[1,2,4]thiadiazol-5-yl]-4-(2-methyl-benzyl)-piperazine
4-[5-(4-Phenethyl-piperazin-1-yl)-[1,2,4]thiadiazol-3-yl]-benzonitrile
3-[5-(4-Phenethyl-piperazin-1-yl)-[1,2,4]thiadiazol-3-yl]-benzonitrile
4-(5-{4-[2-(4-Fluoro-phenyl)-ethyl]-piperazin-1-yl}-[1,2,4]thiadiazol-3-yl)-benzonitrile
3-(5-{4-[2-(4-Fluoro-phenyl)-ethyl]-piperazin-1-yl}-[1,2,4]thiadiazol-3-yl)-benzonitrile
4-(5-{4-[2-(4-Chloro-phenyl)-ethyl]-piperazin-1-yl}-[1,2,4]thiadiazol-3-yl)-benzonitrile
3-(5-{4-[2-(4-Chloro-phenyl)-ethyl]-piperazin-1-yl}-[1,2,4]thiadiazol-3-yl)-benzonitrile
4-{5-[4-(2-Methyl-benzyl)-piperazin-1-yl]-[1,2,4]thiadiazol-3-yl}-benzonitrile
3-{5-[4-(2-Methyl-benzyl)-piperazin-1-yl]-[1,2,4]thiadiazol-3-yl}-benzonitrile
1-[3-(4-Chloro-phenyl)-[1,2,4]thiadiazol-5-yl]-4-[2-(3,4-difluoro-phenyl)-ethyl]-piperazine
1-[3-(3-Chloro-phenyl)-[1,2,4]thiadiazol-5-yl]-4-[2-(3,4-difluoro-phenyl)-ethyl]-piperazine
1-[2-(3,4-Difluoro-phenyl)-ethyl]-4-[3-(3,4-difluoro-phenyl)-[1,2,4]thiadiazol-5-yl]-piperazine
3-(5-{4-[2-(3,4-Difluoro-phenyl)-ethyl]-piperazin-1-yl}-[1,2,4]thiadiazol-3-yl)-benzonitrile
4-(5-{4-[2-(3,4-Difluoro-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(3-trifluoromethyl-phenyl)-ethyl]-piperazine
1-[3-(3-Fluoro-phenyl)-[1,2,4]thiadiazol-5-yl]-4-[2-(3-trifluoromethyl-phenyl)-ethyl]-piperazine
1-[3-(3-Chloro-phenyl)-[1,2,4]thiadiazol-5-yl]-4-[2-(3-trifluoromethyl-phenyl)-ethyl]-piperazine
4-(5-{4-[2-(3-Trifluoromethyl-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(4-trifluoromethyl-phenyl)-ethyl]-piperazine
1-[3-(3-Chloro-phenyl)-[1,2,4]thiadiazol-5-yl]-4-[2-(4-trifluoromethyl-phenyl)-ethyl]-piperazine
1-[3-(3,4-Difluoro-phenyl)-[1,2,4]thiadiazol-5-yl]-4-[2-(4-trifluoromethyl-phenyl)-ethyl]-piperazine or
4-(5-{4-[2-(4-Trifluoromethyl-phenyl)-ethyl]-piperazin-1-yl}-[1,2,4]thiadiazol-3-yl)-benzonitrile.

E4. A compound of formula I according to E1, wherein at least one of $A^1$ or $A^2$ is pyridine-2-yl, pyridine-3-yl or pyridine-4-yl.

E5. Compounds of formula I according to E4, which compounds are
1-[2-(3-Methoxy-phenyl)-ethyl]-4-(3-pyridin-4-yl-[1,2,4]thiadiazol-5-yl)-piperazine
1-[2-(3-Methoxy-phenyl)-ethyl]-4-[3-(6-trifluoromethyl-pyridin-3-yl)-[1,2,4]thiadiazol-5-yl]-piperazine
1-[2-(4-Methoxy-phenyl)-ethyl]-4-[3-(6-trifluoromethyl-pyridin-3-yl)-[1,2,4]thiadiazol-5-yl]-piperazine
1-[2-(4-Methoxy-phenyl)-ethyl]-4-(3-pyridin-4-yl-[1,2,4]thiadiazol-5-yl)-piperazine
1-[3-(4-Chloro-phenyl)-[1,2,4]thiadiazol-5-yl]-4-[2-(2-methoxy-pyridin-4-yl)-ethyl]-piperazine
1-[3-(4-Chloro-phenyl)-[1,2,4]thiadiazol-5-yl]-4-[2-(6-methoxy-pyridin-3-yl)-ethyl]-piperazine
1-[3-(3-Chloro-phenyl)-[1,2,4]thiadiazol-5-yl]-4-[2-(2-methoxy-pyridin-4-yl)-ethyl]-piperazine
1-[3-(3-Fluoro-phenyl)-[1,2,4]thiadiazol-5-yl]-4-[2-(2-methoxy-pyridin-4-yl)-ethyl]-piperazine
1-[3-(5-Chloro-pyridin-3-yl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(6-methoxy-pyridin-3-yl)-ethyl]-piperazine
1-[3-(6-Methyl-pyridin-3-yl)-[1,2,4]thiadiazol-5-yl]-4-phenethyl-piperazine
1-[2-(4-Methoxy-phenyl)-ethyl]-4-[3-(6-methyl-pyridin-3-yl)-[1,2,4]thiadiazol-5-yl]-piperazine
1-[2-(4-Fluoro-phenyl)-ethyl]-4-[3-(6-methyl-pyridin-3-yl)-[1,2,4]thiadiazol-5-yl]-piperazine
1-[2-(2-Methoxy-pyridin-4-yl)-ethyl]-4-[3-(6-methyl-pyridin-3-yl)-[1,2,4]thiadiazol-5-yl]-piperazine
1-[2-(4-Chloro-phenyl)-ethyl]-4-[3-(6-methyl-pyridin-3-yl)-[1,2,4]thiadiazol-5-yl]-piperazine
1-[3-(3-Fluoro-phenyl)-[1,2,4]thiadiazol-5-yl]-4-[2-(6-methoxy-pyridin-3-yl)-ethyl]-piperazine
1-[3-(3,4-Difluoro-phenyl)-[1,2,4]thiadiazol-5-yl]-4-[2-(6-methoxy-pyridin-3-yl)-ethyl]-piperazine
1-[3-(3,4-Difluoro-phenyl)-[1,2,4]thiadiazol-5-yl]-4-[2-(2-methoxy-pyridin-4-yl)-ethyl]-piperazine
4-(5-{4-[2-(6-Methoxy-pyridin-3-yl)-ethyl]-piperazin-1-yl}-[1,2,4]thiadiazol-3-yl)-benzonitrile
3-(5-{4-[2-(6-Methoxy-pyridin-3-yl)-ethyl]-piperazin-1-yl}-[1,2,4]thiadiazol-3-yl)-benzonitrile
4-(5-{4-[2-(2-Methoxy-pyridin-4-yl)-ethyl]-piperazin-1-yl}-[1,2,4]thiadiazol-3-yl)-benzonitrile
3-(5-{4-[2-(2-Methoxy-pyridin-4-yl)-ethyl]-piperazin-1-yl}-[1,2,4]thiadiazol-3-yl)-benzonitrile
1-[3-(4-Chloro-pyridin-2-yl)-[1,2,4]thiadiazol-5-yl]-4-phenethyl-piperazine
1-[3-(5-Chloro-pyridin-2-yl)-[1,2,4]thiadiazol-5-yl]-4-phenethyl-piperazine 1-[3-(4-Chloro-pyridin-2-yl)-[1,2,4]thiadiazol-5-yl]-4-[2-(4-fluoro-phenyl)-ethyl]-piperazine
1-[2-(4-Chloro-phenyl)-ethyl]-4-[3-(4-chloro-pyridin-2-yl)-[1,2,4]thiadiazol-5-yl]-piperazine
1-[2-(4-Chloro-phenyl)-ethyl]-4-[3-(5-chloro-pyridin-2-yl)-[1,2,4]thiadiazol-5-yl]-piperazine
1-[3-(4-Chloro-pyridin-2-yl)-[1,2,4]thiadiazol-5-yl]-4-[2-(4-methoxy-phenyl)-ethyl]-piperazine
1-[3-(5-Chloro-pyridin-2-yl)-[1,2,4]thiadiazol-5-yl]-4-[2-(4-methoxy-phenyl)-ethyl]-piperazine
1-[3-(4-Chloro-pyridin-2-yl)-[1,2,4]thiadiazol-5-yl]-4-[2-(2-methoxy-pyridin-4-yl)-ethyl]-piperazine
1-[3-(4-Chloro-pyridin-2-yl)-[1,2,4]thiadiazol-5-yl]-4-(2-methyl-benzyl)-piperazine
1-[3-(5-Chloro-pyridin-2-yl)-[1,2,4]thiadiazol-5-yl]-4-(2-methyl-benzyl)-piperazine
1-[3-(5-Chloro-pyridin-3-yl)-[1,2,4]thiadiazol-5-yl]-4-phenethyl-piperazine
1-[3-(5-Chloro-pyridin-3-yl)-[1,2,4]thiadiazol-5-yl]-4-[2-(4-fluoro-phenyl)-ethyl]-piperazine
1-[2-(4-Chloro-phenyl)-ethyl]-4-[3-(5-chloro-pyridin-3-yl)-[1,2,4]thiadiazol-5-yl]-piperazine
1-[3-(5-Chloro-pyridin-3-yl)-[1,2,4]thiadiazol-5-yl]-4-[2-(2-methoxy-pyridin-4-yl)-ethyl]-piperazine
1-[3-(5-Chloro-pyridin-2-yl)-[1,2,4]thiadiazol-5-yl]-4-[2-(3,4-difluoro-phenyl)-ethyl]-piperazine
1-[2-(3,4-Difluoro-phenyl)-ethyl]-4-[3-(6-methyl-pyridin-3-yl)-[1,2,4]thiadiazol-5-yl]-piperazine
1-[3-(5-Chloro-pyridin-3-yl)-[1,2,4]thiadiazol-5-yl]-4-[2-(3-trifluoromethyl-phenyl)-ethyl]-piperazine
1-(2-Methyl-benzyl)-4-[3-(6-methyl-pyridin-3-yl)-[1,2,4]thiadiazol-5-yl]-piperazine
1-[3-(5-Chloro-pyridin-3-yl)-[1,2,4]thiadiazol-5-yl]-4-(2-methyl-benzyl)-piperazine or
1-[3-(5-Chloro-pyridin-3-yl)-[1,2,4]thiadiazol-5-yl]-4-[2-(4-trifluoromethyl-phenyl)-ethyl]-piperazine.

E6. A compound of formula I according to E1, wherein one of $A^1$ or $A^2$ is benzo[1,3]dioxol.

E7. A compound of formula I according to E6, which compound is
1-Benzo[1,3]dioxol-5-ylmethyl-4-(3-p-tolyl-[1,2,4]thiadiazol-5-yl)-piperazine.

E8. A compound of formula I according to E1, wherein at least one of $A^1$ or $A^2$ is thiophen-2-yl.

E9. Compound of formula I according to E8, which compounds are
1-[2-(3-Methoxy-phenyl)-ethyl]-4-(3-thiophen-2-yl-[1,2,4]thiadiazol-5-yl)-piperazine or
1-[2-(4-Methoxy-phenyl)-ethyl]-4-(3-thiophen-2-yl-[1,2,4]thiadiazol-5-yl)-piperazine.

E10. A compound of formula I according to E1, wherein at least one of $A^1$ or $A^2$ are pyrazine-2-yl.

E11. Compounds of formula I according to E10, which compounds are
2-(5-{4-[2-(4-Methoxy-phenyl)-ethyl]-piperazin-1-yl}-[1,2,4]thiadiazol-3-yl)-pyrazine or
2-(5-{4-[2-(3-Methoxy-phenyl)-ethyl]-piperazin-1-yl}-[1,2,4]thiadiazol-3-yl)-pyrazine.

E12. A compound of formula I according to E1, wherein $A^2$ is cycloalkyl.

E13. Compounds of formula I according to E12, which compounds are
1-(2-Cyclohexyl-ethyl)-4-[3-(3,4-difluoro-phenyl)-[1,2,4]thiadiazol-5-yl]-piperazine or
1-(2-Cyclohexyl-ethyl)-4-[3-(3-fluoro-phenyl)-[1,2,4]thiadiazol-5-yl]-piperazine.

E14. A process for preparation of compounds of formula I according to E1, which process comprises coupling a compound of formula

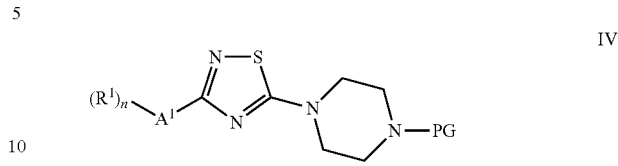

with a compound of formula

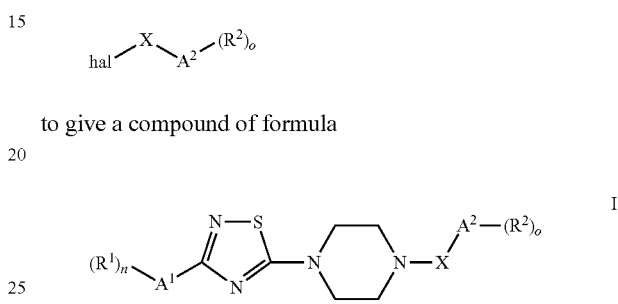

to give a compound of formula wherein the definitions are as described in E1, or
if desired, converting the compounds obtained into pharmaceutically acceptable acid addition salts.

E15. A compound according to any one of E1-E13, when manufactured according to a process of E14.

E16. A compound according to any one of E1-E13 for use as therapeutically active substance.

E17. A medicament containing one or more compounds as described in any one of E1 to E13 and pharmaceutically acceptable excipients.

E18. A medicament according to E17, wherein the illnesses which may be treated are Alzheimer's disease, Pick's disease, corticobasal degeneration, progressive supranuclear palsy, frontotemporal dementia and parkinsonism (linked to chromosome 17, FTDP-17).

E19. The use of a compound as claimed in any one of E1 to E13 for the treatment of Alzheimer's disease, Pick's disease, corticobasal degeneration, progressive supranuclear palsy, frontotemporal dementia and parkinsonism (linked to chromosome 17, FTDP-17).

E20. The use of a compound as claimed in any one of E1 to E13 for the manufacture of medicaments for the treatment of Alzheimer's disease, Pick's disease, corticobasal degeneration, progressive supranuclear palsy, frontotemporal dementia and parkinsonism (linked to chromosome 17, FTDP-17).

E21. A method for the treatment of Alzheimer's disease, Pick's disease, corticobasal degeneration, progressive supranuclear palsy, frontotemporal dementia and parkinsonism (linked to chromosome 17, FTDP-17), which method comprising administering an effective amount of a compound as defined in any one of E1-E13.

E22. The invention as described herein.

In an embodiment, the compounds of formula IA have a structure of formula I.

For example, the present invention encompasses a compound of formula I or IA, wherein $C^1$ has the same meaning as defined for $A^1$ and $C^2$ has the same meaning as defined for $A^2$; wherein,
$R^1$ is hydrogen; lower alkyl; lower alkyl substituted by halogen; halogen; lower alkoxy; lower alkoxy substituted by halogen; or is cyano; preferably $R^1$ is lower alkyl substituted by halogen; halogen; or lower alkoxy; preferably $R^1$ is lower alkyl substituted by halogen; or halogen;

$R^2$ is hydrogen; lower alkyl; lower alkyl substituted by halogen; halogen; lower alkoxy; or is lower alkoxy substituted by halogen; preferably $R^2$ is hydrogen; lower alkyl; halogen; or is lower alkoxy; preferably $R^2$ is hydrogen; halogen; or is lower alkoxy;

$A^1$ is phenyl; benzo[1,3]dioxol; pyridine-2-yl; pyridine-3-yl; pyridine-4-yl; thiophen-2-yl; pyrazine-2-yl; or cycloalkyl; preferably $A^1$ is phenyl; pyridine-2-yl; pyridine-3-yl; pyridine-4-yl; thiophen-2-yl; pyrazine-2-yl; or cycloalkyl; preferably $A^1$ is phenyl; pyridine-2-yl; pyridine-3-yl; pyridine-4-yl; pyrazine-2-yl; or cycloalkyl; preferably $A^1$ is phenyl; pyridine-2-yl; pyridine-3-yl; pyridine-4-yl; or pyrazine-2-yl; preferably $A^1$ is phenyl; pyridine-3-yl or pyridine-4-yl; preferably $A^1$ is phenyl; or pyridine-3-yl;

$A^2$ is phenyl; benzo[1,3]dioxol; pyridine-2-yl; pyridine-3-yl; pyridine-4-yl; pyrazine-2-yl; thiophen-2-yl; or cycloalkyl; preferably $A^2$ is phenyl; pyridine-2-yl; pyridine-3-yl; pyridine-4-yl; thiophen-2-yl; pyrazine-2-yl; or cycloalkyl; preferably $A^2$ is phenyl; pyridine-2-yl; pyridine-3-yl; pyridine-4-yl; or pyrazine-2-yl; preferably $A^2$ is phenyl; pyridine-3-yl; pyridine-4-yl; or pyrazine-2-yl; preferably $A^2$ is phenyl; pyridine-3-yl; or pyridine-4-yl;

X is a bond; —$CH_2$—; —$CH_2$—CHR—; —$CH_2$—$CH_2$—$CH_2$—; —$CH_2C(O)$—; —$C(O)NH$—; —CHR'—$CH_2$—;

—$CH_2\overset{\parallel}{C}$—; or —$CH_2$—△ ;

preferably X is —$CH_2$—; —$CH_2$—CHR—; —$CH_2$—$CH_2$—$CH_2$—; —$CH_2C(O)$—; —CHR'—$CH_2$—;

—$CH_2\overset{\parallel}{C}$—; or —$CH_2$—△ ;

preferably X is —$CH_2$—; —$CH_2$—CHR—; —$CH_2$—$CH_2$—$CH_2$—; —CHR'—$CH_2$—; or

—$CH_2$—△ ;

preferably X is —$CH_2$—; —$CH_2$—CHR—; —CHR'—$CH_2$—;

R is hydrogen; hydroxyl; halogen; or lower alkyl; preferably R is hydrogen; halogen or lower alkyl; preferably R is hydrogen or halogen;

R' is lower alkyl;

n is 1 or 2; if n is 2, $R^1$ may be independently from each other; preferably n is 1;

o is 1 or 2; if o is 2, $R^2$ may be independently from each other;

In a yet more particular embodiment, the compounds of the present invention have a structure according to formula I or IA, whereby X is —$CH_2$—; —$CH_2$—CHR—; —$CH_2$—$CH_2$—$CH_2$—; —$CH_2C(O)$—; —CHR'—$CH_2$—;

—$CH_2\overset{\parallel}{C}$—; or —$CH_2$—△ .

In a particular embodiment of the present invention, the compounds have a structure according to formula IA or formula I, wherein X is selected from —$CH_2$—CHR—; or —CHR'—$CH_2$—. In yet another particular embodiment, R is selected from hydrogen or lower alkyl. In a yet more particular embodiment, R is hydrogen.

In another particular embodiment of the present invention, the compounds have a structure according to formula IA or formula I, wherein X is selected from —$CH_2$—CHR—; or —CHR'—$CH_2$—. In yet another particular embodiment, R is hydrogen. In another particular embodiment of the present invention, the compounds have a structure according to formula I, wherein $A^1$ is selected from: phenyl; pyridine-2-yl; pyridine-3-yl; pyridine-4-yl; pyrazine-2-yl.

In another particular embodiment of the present invention, the compounds have a structure according to formula I, wherein $A^2$ is selected from: phenyl; pyridine-2-yl; pyridine-3-yl; pyridine-4-yl; pyrazine-2-yl; or cycloalkyl.

In a particular embodiment of the invention, the compounds have a structure of formula I, whereby $A^1$ is pyridine-2-yl; pyridine-3-yl; or pyridine-4-yl; and $A^2$ is phenyl; yet more in particular $A^1$ is pyridine-3-yl; or pyridine-4-yl; yet more in particular $A^1$ is pyridine-3-yl.

In another particular embodiment of the present invention, the compounds have a structure according to formula I, wherein $A^1$ is phenyl; $A^2$ is phenyl and n is 1.

In another particular embodiment of the present invention, the compounds have a structure according to formula I, wherein $A^1$ is phenyl; $A^2$ is phenyl and n is 2.

In another particular embodiment of the present invention, the compounds have a structure according to formula I, wherein $A^1$ is phenyl; $A^2$ is phenyl and o is 1.

In another particular embodiment of the present invention, the compounds have a structure according to formula I, wherein $A^1$ is phenyl; $A^2$ is phenyl and o is 2.

In a particular embodiment of the invention, the compounds have a structure of formula I, whereby $A^1$ is phenyl; and $A^2$ is pyridine-2-yl; pyridine-3-yl; or pyridine-4-yl; yet more in particular $A^2$ is pyridine-3-yl; or pyridine-4-yl; yet more in particular $A^2$ is pyridine-3-yl.

In a particular embodiment of the invention, the compounds have a structure of formula I, whereby $A^1$ is pyridine-2-yl; pyridine-3-yl; or pyridine-4-yl; and $A^2$ is pyridine-3-yl; yet more in particular $A^1$ is pyridine-3-yl; or pyridine-4-yl; yet more in particular $A^1$ is pyridine-3-yl.

In a particular embodiment of the invention, the compounds have a structure of formula I, whereby $A^1$ is pyridine-2-yl; pyridine-3-yl; or pyridine-4-yl; and $A^2$ is pyridine-4-yl; yet more in particular $A^1$ is pyridine-3-yl; or pyridine-4-yl; yet more in particular $A^1$ is pyridine-3-yl.

In a particular embodiment of the invention, the compounds have a structure of formula I, whereby $A^1$ is pyridine-3-yl; and $A^2$ is pyridine-2-yl; pyridine-3-yl; or pyridine-4-yl; yet more in particular $A^2$ is pyridine-3-yl; or pyridine-4-yl; yet more in particular $A^2$ is pyridine-3-yl.

In a particular embodiment of the invention, the compounds have a structure of formula I, whereby $A^1$ is pyridine- 4-yl; and A² is pyridine-2-yl; pyridine-3-yl; or pyridine-4-yl; yet more in particular A² is pyridine-3-yl; or pyridine-4-yl; yet more in particular A² is pyridine-3-yl.

The present compounds are useful for treating certain neurodegenerative disorders characterized by cytotoxic TAU misfolding and/or aggregation in order to delay or halt the progression of such diseases. Such diseases are summarized under the term tauopathy. The term "Tauopathy" refers to a disease characterised by dysfunctioning and/or toxicity of the TAU protein, characterised by oligomers, aggregates or polymers of said protein. Such diseases include, but are not limited to, Alzheimer's disease, Pick's disease, corticobasal degeneration, progressive supranuclear palsy, frontotemporal dementia and parkinsonism (linked to chromosome 17, FTDP-17).

Tauopathies are characterised by insoluble aggregates or polymers of hyperphosphorylated TAU which are formed by self-polymerisation of TAU monomers. The precise molecular mechanisms involved in TAU aggregation are not precisely known, but may involve a partial denaturation or misfolding of TAU in conformations which have a high propensity to self-organise into higher order structures. The misfolding and aggregation may be triggered by hyperphosphorylation of TAU, although at present, it cannot be excluded that such aberrant phosphorylation is a consequence rather than the cause of aggregation.

TAU is a protein with the ability to bind- and consequently stabilise and define-microtubule structure and function in neurons. The binding of TAU to microtubules is regulated by phosphorylation of TAU; several TAU phosphorylation sites and their corresponding kinases have been identified which control phosphorylation status of TAU and consequently modulate the affinity of TAU-binding to microtubules.

An important aspect of the TAU aggregation is its associated cytotoxicity, which reduces neuronal integrity and functionality and ultimately resulting in disease symptoms. A direct role of TAU in disease onset has been established unequivocally by the elucidation of familial mutations in TAU, which appear to be responsible for a very early and sometimes aggressive form of tauopathy. Such mutations comprise changes in the amino acid sequence of TAU that—directly or indirectly promote neurotoxic aggregation.

Alzheimer's disease is the best known of these, where TAU protein is deposited within neurons in the form of neurofibrillary tangles (NFTs). They were first described by the eponymous Alois Alzheimer in one of his patients suffering from the disorder. The term "Alzheimer's disease" as used herein, refers to a chronic progressive nervous disease characterised by neurodegeneration with as most important (early) symptom being memory loss. As the disease advances, symptoms may include confusion, irritability and aggression, mood swings, language breakdown, long-term memory loss, and the general withdrawal of the sufferer as their senses decline.

Tangles are formed by hyperphosphorylation of a microtubule-associated protein known as TAU, causing it to aggregate in an insoluble form. (These aggregations of hyperphosphorylated TAU protein are also referred to as PHF, or "paired helical filaments"). The precise mechanism of tangle formation is not completely understood, and it is still controversial whether tangles are a primary causative factor in the disease or play a more peripheral role. AD is also classified as an amyloidosis because of the presence of senile plaques.

Other conditions in which neurofibrillary tangles are commonly observed include: Progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia with NFTs, similar to AD, but without plaques, ganglioglioma and gangliocytoma, meningioangiomatosis, subacute sclerosing panencephalitis, tuberous sclerosis, Hallervorden-Spatz disease, and lipofuscinosis.

The non-Alzheimer's tauopathies are sometimes grouped together as "Pick's complex". In Pick's disease and corticobasal degeneration TAU proteins are deposited in the form of inclusion bodies within swollen or "ballooned" neurons. Argyrophilic grain disease (AGD), another type of dementia, is marked by the presence of abundant argyrophilic grains and coiled bodies on microscopic examination of brain tissue.

Similar compounds as described in formula IA and I of the present invention have been described in WO2007/090617.

In contradiction to the findings in WO2007/090617, it has been found that if there is no linking group between the phenyl moiety and the thiadiazole group, there was a marked decrease of the clearance (Clint), in particular in the human in-vitro microsomes assay. It is very important for a drug to have a moderate or low clearance, as this often leads to a higher oral bioavailability. Reducing the clearance of a compound/drug, could then potentially reduce drastically the daily dose required for efficacy and therefore give also a much better safety profile as well. Therefore a low clearance is an essential feature for therapeutic applicability.

The following examples in the table below highlight these finding, where the use of compounds, wherein no linking group between the phenyl moiety and the thiadiazole group exists, have led to compounds with a lower clearance (Clint) and higher metabolic stability (MAB) in human in vitro microsomes.

Microsomal Stability Testing—Assay Description

The microsomal stability assay measures the rate of disappearance of a test compound from an incubation containing human or animal liver microsomes and metabolic cofactors (typically NADPH). The assay is primarily used for ranking the relative CYP-mediated metabolism propensities of compounds within a chemical series and as a guide to selecting sufficiently stable compounds for pharmacokinetics and pharmacodynamics experiments. [In addition to CYPs, microsomally located enzymes which also make use of NADPH (such as flavone mono-oxygenases) and those which require no cofactors (such as carboxylesterases) are active.]

Incubations are performed in 96-well deep-well plates with a final incubation volume of 600 µL. Incubations contain (finally) 1-2 µM test compound, 0.5 mg/mL liver microsomes (typically human, rat or mouse) and NADPH regenerating system. 50 µL aliquots are removed after 1, 3, 6, 9, 15, 25, 35 and 45 minutes and quenched in 150 µL acetonitrile containing internal standard. Samples are then cooled and centrifuged before analysis by LC-MS/MS.

Log peak area ratio (test compound peak area/internal standard peak area) is plotted against incubation time and a linear fit made to the data with emphasis upon the initial rate of compound disappearance. The slope of the fit is then used to calculate the intrinsic clearance:

$$Cl_{int}(\mu L/min/mg) = -slope(min^{-1}) * 1000/[\text{protein concentration (mg/mL)}]$$

TABLE 1

| Compounds disclosed in WO2007/090617 | MAB and Clint data | Compounds disclosed in the present application | MAB and Clint data |
|---|---|---|---|
| According to WO2007/090617 | Clint. (Hum/Rat) 39/482 uL/min/mg protein | Example 2 | Clint. (Hum/Rat) 19/48 uL/min/mg protein |
| According to WO2007/090617 | Clint. (Hum/Rat) 46/103 uL/min/mg protein | Example 88 | Clint. (Hum/Rat) 12/23 uL/min/mg protein |

As it can be seen in the table above, it has been found a marked increase of metabolic stability (increase MAB, decrease of the clearance Clint) in particular in human in vitro microsomes.

Objects of the present invention are new compounds of formula IA and I and their pharmaceutically acceptable salts, their use for the treatment of diseases related to the biological function of dysfunction of TAU protein, which diseases comprise Alzheimer's disease, Pick's disease, corticobasal degeneration, progressive supranuclear palsy, frontotemporal dementia and parkinsonism (linked to chromosome 17, FTDP-17), their manufacture and medicaments based on a compound in accordance with the invention in the control or prevention of illnesses.

The preferred indication using the compounds of the present invention is Alzheimer's disease.

As used herein, the term "lower alkyl" denotes a saturated straight- or branched-chain group containing from 1 to 7 carbon atoms, preferably from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "lower alkoxy substituted by halogen" denotes an alkoxyl group as defined above, wherein at least one hydrogen atom is replaced by halogen, for example $OCF_3$, $OCHF_2$, $OCH_2F$, $OCH_2CF_3$, $OCH_2CH_2CF_3$, $OCH_2CF_2CF_3$ and the like.

The term "halogen" denotes chlorine, iodine, fluorine and bromine.

The term "cycloalkyl" is an alkylene ring, containing from 3 to 6 carbon ring atoms. Preferred is cyclopropyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

One embodiment of the invention are compounds of formula IA, wherein $C^1$ and $C^2$ are both phenyl, for example the following compounds 1-(2,4-Dichloro-benzyl)-4-(3-p-tolyl-[1,2,4]thiadiazol-5-yl)-piperazine
1-Phenethyl-4-(3-p-tolyl-[1,2,4]thiadiazol-5-yl)-piperazine
1-[2-(3,4-Dichloro-phenyl)-ethyl]-4-(3-p-tolyl-[1,2,4]thiadiazol-5-yl)-piperazine
1-(2-Methyl-benzyl)-4-(3-p-tolyl-[1,2,4]thiadiazol-5-yl)-piperazine
1-[3-(4-Chloro-phenyl)-[1,2,4]thiadiazol-5-yl]-4-(2-methyl-benzyl)-piperazine
1-[3-(3-Methoxy-phenyl)-[1,2,4]thiadiazol-5-yl]-4-(2-methyl-benzyl)-piperazine
1-[3-(4-Chloro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(3-methoxy-phenyl)-[1,2,4]thiadiazol-5-yl]-piperazine
1-[2-(3-Methoxy-phenyl)-ethyl]-4-(3-p-tolyl-[1,2,4]thiadiazol-5-yl)-piperazine
1-[3-(4-Chloro-phenyl)-[1,2,4]thiadiazol-5-yl]-4-[2-(4-methoxy-phenyl)-ethyl]-piperazine
1-[2-(4-Methoxy-phenyl)-ethyl]-4-[3-(3-methoxy-phenyl)-[1,2,4]thiadiazol-5-yl]-piperazine
1-[2-(4-Methoxy-phenyl)-ethyl]-4-(3-p-tolyl-[1,2,4]thiadiazol-5-yl)-piperazine
1-[3-(4-Chloro-phenyl)-[1,2,4]thiadiazol-5-yl]-4-[2-(3-fluoro-phenyl)-ethyl]-piperazine
1-[2-(3-Chloro-phenyl)-ethyl]-4-[3-(4-chloro-phenyl)-[1,2,4]thiadiazol-5-yl]-piperazine 1-[3-(4-Chloro-phenyl)-[1,2,4]thiadiazol-5-yl]-4-(2-m-tolyl-ethyl)-piperazine
1-[3-(4-Chloro-phenyl)-[1,2,4]thiadiazol-5-yl]-4-[2-(4-fluoro-phenyl)-ethyl]-piperazine
1-[2-(4-Chloro-phenyl)-ethyl]-4-[3-(4-chloro-phenyl)-[1,2,4]thiadiazol-5-yl]-piperazine
1-[3-(4-Chloro-phenyl)-[1,2,4]thiadiazol-5-yl]-4-(2-p-tolyl-ethyl)-piperazine
1-[3-(4-Chloro-phenyl)-[1,2,4]thiadiazol-5-yl]-4-[2-(2-methoxy-phenyl)-ethyl]-piperazine
1-[3-(4-Chloro-phenyl)-[1,2,4]thiadiazol-5-yl]-4-[2-(2-fluoro-phenyl)-ethyl]-piperazine
1-[2-(2-Chloro-phenyl)-ethyl]-4-[3-(4-chloro-phenyl)-[1,2,4]thiadiazol-5-yl]-piperazine
1-[3-(3,5-Dichloro-phenyl)-[1,2,4]thiadiazol-5-yl]-4-[2-(3-methoxy-phenyl)-ethyl]-piperazine
1-[3-(4-Chloro-phenyl)-[1,2,4]thiadiazol-5-yl]-4-[3-(3-methoxy-phenyl)-propyl]-piperazine
1-[3-(4-Fluoro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(2-methoxy-phenyl)-[1,2,4]thiadiazol-5-yl]-piperazine
1-[2-(3-Methoxy-phenyl)-ethyl]-4-[3-(4-trifluoromethoxy-phenyl)-[1,2,4]thiadiazol-5-yl]-piperazine
1-[2-(4-Methoxy-phenyl)-ethyl]-4-[3-(4-trifluoromethoxy-phenyl)-[1,2,4]thiadiazol-5-yl]-piperazine
1-[3-(4-Chloro-phenyl)-[1,2,4]thiadiazol-5-yl]-4-[2-(3-trifluoromethoxy-phenyl)-ethyl]-piperazine
1-[3-(4-Chloro-phenyl)-[1,2,4]thiadiazol-5-yl]-4-[3-(2-methoxy-phenyl)-propyl]-piperazine
1-[2-(4-Methoxy-phenyl)-ethyl]-4-[3-(4-methoxy-phenyl)-[1,2,4]thiadiazol-5-yl]-piperazine
1-[3-(3-Chloro-phenyl)-[1,2,4]thiadiazol-5-yl]-4-[2-(4-methoxy-phenyl)-ethyl]-piperazine
1-[2-(4-Methoxy-phenyl)-ethyl]-4-[3-(2-methoxy-phenyl)-[1,2,4]thiadiazol-5-yl]-piperazine
1-[3-(3,5-Dichloro-phenyl)-[1,2,4]thiadiazol-5-yl]-4-[2-(4-methoxy-phenyl)-ethyl]-piperazine
1-[3-(4-Fluoro-phenyl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(4-methoxy-phenyl)-[1,2,4]thiadiazol-5-yl]-piperazine
1-[3-(4-Chloro-phenyl)-[1,2,4]thiadiazol-5-yl]-4-[2-(4-ethoxy-phenyl)-ethyl]-piperazine
1-[3-(4-Chloro-phenyl)-[1,2,4]thiadiazol-5-yl]-4-[2-(3-isopropoxy-phenyl)-ethyl]-piperazine
1-[3-(4-Chloro-phenyl)-[1,2,4]thiadiazol-5-yl]-4-[3-(4-methoxy-phenyl)-propyl]-piperazine
2-{4-[3-(4-Chloro-phenyl)-[1,2,4]thiadiazol-5-yl]-piperazin-1-yl}-1-(4-methoxy-phenyl)-ethanone
2-{4-[3-(4-Chloro-phenyl)-[1,2,4]thiadiazol-5-yl]-piperazin-1-yl}-1-(4-methoxy-phenyl)-ethanol
1-[3-(4-Chloro-2-fluoro-phenyl)-[1,2,4]thiadiazol-5-yl]-4-[2-(3-methoxy-phenyl)-ethyl]-piperazine
1-[3-(4-Chloro-2-fluoro-phenyl)-[1,2,4]thiadiazol-5-yl]-4-[2-(4-methoxy-phenyl)-ethyl]-piperazine
1-[3-(2-Chloro-phenyl)-[1,2,4]thiadiazol-5-yl]-4-[2-(3-methoxy-phenyl)-ethyl]-piperazine
1-[3-(2-Chloro-phenyl)-[1,2,4]thiadiazol-5-yl]-4-[2-(4-methoxy-phenyl)-ethyl]-piperazine
1-[3-(4-Chloro-phenyl)-[1,2,4]thiadiazol-5-yl]-4-[2-(4-methoxy-phenyl)-allyl]-piperazine
2-{4-[3-(4-Chloro-phenyl)-[1,2,4]thiadiazol-5-yl]-piperazin-1-yl}-1-(3-methoxy-phenyl)-ethanone
2-{4-[3-(4-Chloro-phenyl)-[1,2,4]thiadiazol-5-yl]-piperazin-1-yl}-1-(3-methoxy-phenyl)-ethanol
2-{4-[3-(4-Chloro-phenyl)-[1,2,4]thiadiazol-5-yl]-piperazin-1-yl}-1-(3-fluoro-phenyl)-ethanone
2-{4-[3-(4-Chloro-phenyl)-[1,2,4]thiadiazol-5-yl]-piperazin-1-yl}-1-(3-fluoro-phenyl)-ethanol
1-[3-(4-Chloro-phenyl)-[1,2,4]thiadiazol-5-yl]-4-[2-fluoro-2-(4-methoxy-phenyl)-ethyl]-piperazine
1-[3-(4-Chloro-phenyl)-[1,2,4]thiadiazol-5-yl]-4-[2-fluoro-2-(3-methoxy-phenyl)-ethyl]-piperazine
1-[3-(4-Fluoro-2-methoxy-phenyl)-[1,2,4]thiadiazol-5-yl]-4-[2-(3-methoxy-phenyl)-ethyl]-piperazine
1-[3-(4-Fluoro-2-methoxy-phenyl)-[1,2,4]thiadiazol-5-yl]-4-[2-(4-methoxy-phenyl)-ethyl]-piperazine
1-[1-(4-Chloro-phenyl)-cyclopropylmethyl]-4-[3-(4-chloro-phenyl)-[1,2,4]thiadiazol-5-yl]-piperazine
1-[3-(4-Chloro-phenyl)-[1,2,4]thiadiazol-5-yl]-4-[2-(3-difluoromethoxy-phenyl)-ethyl]-piperazine
1-[3-(4-Chloro-phenyl)-[1,2,4]thiadiazol-5-yl]-4-[2-(4-difluoromethoxy-phenyl)-ethyl]-piperazine
1-[3-(4-Chloro-phenyl)-[1,2,4]thiadiazol-5-yl]-4-[2-(4-isopropoxy-phenyl)-ethyl]-piperazine
1-[3-(4-Chloro-phenyl)-[1,2,4]thiadiazol-5-yl]-4-[2-(4-methoxy-phenyl)-propyl]-piperazine
1-[3-(4-Chloro-phenyl)-[1,2,4]thiadiazol-5-yl]-4-[2-(4-methoxy-phenyl)-1-methyl-ethyl]-piperazine
4-(5-{4-[2-(4-Methoxy-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(3-fluoro-4-methoxy-phenyl)-ethyl]-piperazine
3-(5-{4-[2-(4-Methoxy-phenyl)-ethyl]-piperazin-1-yl}-[1,2,4]thiadiazol-3-yl)-benzonitrile
1-[3-(3-Chloro-phenyl)-[1,2,4]thiadiazol-5-yl]-4-phenethyl-piperazine
1-[3-(3-Fluoro-phenyl)-[1,2,4]thiadiazol-5-yl]-4-phenethyl-piperazine
1-[3-(3-Fluoro-phenyl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(4-fluoro-phenyl)-ethyl]-piperazine
1-[2-(4-Fluoro-phenyl)-ethyl]-4-[3-(3-fluoro-phenyl)-[1,2,4]thiadiazol-5-yl]-piperazine
1-[2-(4-Chloro-phenyl)-ethyl]-4-[3-(3-chloro-phenyl)-[1,2,4]thiadiazol-5-yl]-piperazine
1-[2-(4-Chloro-phenyl)-ethyl]-4-[3-(3-fluoro-phenyl)-[1,2,4]thiadiazol-5-yl]-piperazine
1-[3-(3-Chloro-phenyl)-[1,2,4]thiadiazol-5-yl]-4-(2-methyl-benzyl)-piperazine
1-[3-(3-Fluoro-phenyl)-[1,2,4]thiadiazol-5-yl]-4-(2-methyl-benzyl)-piperazine
1-[3-(3,4-Difluoro-phenyl)-[1,2,4]thiadiazol-5-yl]-4-phenethyl-piperazine
1-[3-(3,4-Difluoro-phenyl)-[1,2,4]thiadiazol-5-yl]-4-[2-(4-methoxy-phenyl)-ethyl]-piperazine
1-[3-(3,4-Difluoro-phenyl)-[1,2,4]thiadiazol-5-yl]-4-[2-(4-fluoro-phenyl)-ethyl]-piperazine
1-[2-(4-Chloro-phenyl)-ethyl]-4-[3-(3,4-difluoro-phenyl)-[1,2,4]thiadiazol-5-yl]-piperazine
1-[3-(3,4-Difluoro-phenyl)-[1,2,4]thiadiazol-5-yl]-4-(2-methyl-benzyl)-piperazine
4-[5-(4-Phenethyl-piperazin-1-yl)-[1,2,4]thiadiazol-3-yl]-benzonitrile
3-[5-(4-Phenethyl-piperazin-1-yl)-[1,2,4]thiadiazol-3-yl]-benzonitrile
4-(5-{4-[2-(4-Fluoro-phenyl)-ethyl]-piperazin-1-yl}-[1,2,4]thiadiazol-3-yl)-benzonitrile 3-(5-{4-[2-(4-Fluoro-phenyl)-ethyl]-piperazin-1-yl}-[1,2,4]thiadiazol-3-yl)-benzonitrile
4-(5-{4-[2-(4-Chloro-phenyl)-ethyl]-piperazin-1-yl}-[1,2,4]thiadiazol-3-yl)-benzonitrile
3-(5-{4-[2-(4-Chloro-phenyl)-ethyl]-piperazin-1-yl}-[1,2,4]thiadiazol-3-yl)-benzonitrile
4-{5-[4-(2-Methyl-benzyl)-piperazin-1-yl]-[1,2,4]thiadiazol-3-yl}-benzonitrile
3-{5-[4-(2-Methyl-benzyl)-piperazin-1-yl]-[1,2,4]thiadiazol-3-yl}-benzonitrile
1-[3-(4-Chloro-phenyl)-[1,2,4]thiadiazol-5-yl]-4-[2-(3,4-difluoro-phenyl)-ethyl]-piperazine
1-[3-(3-Chloro-phenyl)-[1,2,4]thiadiazol-5-yl]-4-[2-(3,4-difluoro-phenyl)-ethyl]-piperazine
1-[2-(3,4-Difluoro-phenyl)-ethyl]-4-[3-(3,4-difluoro-phenyl)-[1,2,4]thiadiazol-5-yl]-piperazine
3-(5-{4-[2-(3,4-Difluoro-phenyl)-ethyl]-piperazin-1-yl}-[1,2,4]thiadiazol-3-yl)-benzonitrile
4-(5-{4-[2-(3,4-Difluoro-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(3-trifluoromethyl-phenyl)-ethyl]-piperazine
1-[3-(3-Fluoro-phenyl)-[1,2,4]thiadiazol-5-yl]-4-[2-(3-trifluoromethyl-phenyl)-ethyl]-piperazine
1-[3-(3-Chloro-phenyl)-[1,2,4]thiadiazol-5-yl]-4-[2-(3-trifluoromethyl-phenyl)-ethyl]-piperazine
4-(5-{4-[2-(3-Trifluoromethyl-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(4-trifluoromethyl-phenyl)-ethyl]-piperazine
1-[3-(3-Chloro-phenyl)-[1,2,4]thiadiazol-5-yl]-4-[2-(4-trifluoromethyl-phenyl)-ethyl]-piperazine
1-[3-(3,4-Difluoro-phenyl)-[1,2,4]thiadiazol-5-yl]-4-[2-(4-trifluoromethyl-phenyl)-ethyl]-piperazine
4-(5-{4-[2-(4-Trifluoromethyl-phenyl)-ethyl]-piperazin-1-yl}-[1,2,4]thiadiazol-3-yl)-benzonitrile.
5-(4-(3-phenylpropyl)piperazin-1-yl)-3-(p-tolyl)-1,2,4-thiadiazole
5-(4-(3,4-difluorophenethyl)piperazin-1-yl)-3-(3-fluorophenyl)-1,2,4-thiadiazole or
3-(3,4-difluorophenyl)-5-(4-(3-(trifluoromethyl)phenethyl)piperazin-1-yl)-1,2,4-thiadiazole.

One further embodiment of the invention are compounds of formula IA, wherein at least one of $C^1$ or $C^2$ is pyridine-2-yl, pyridine-3-yl or pyridine-4-yl, for example the following compounds 1-[2-(3-Methoxy-phenyl)-ethyl]-4-(3-pyridin-4-yl-[1,2,4]thiadiazol-5-yl)-piperazine
1-[2-(3-Methoxy-phenyl)-ethyl]-4-[3-(6-trifluoromethyl-pyridin-3-yl)-[1,2,4]thiadiazol-5-yl]-piperazine
1-[2-(4-Methoxy-phenyl)-ethyl]-4-[3-(6-trifluoromethyl-pyridin-3-yl)-[1,2,4]thiadiazol-5-yl]-piperazine
1-[2-(4-Methoxy-phenyl)-ethyl]-4-(3-pyridin-4-yl-[1,2,4]thiadiazol-5-yl)-piperazine
1-[3-(4-Chloro-phenyl)-[1,2,4]thiadiazol-5-yl]-4-[2-(2-methoxy-pyridin-4-yl)-ethyl]-piperazine
1-[3-(4-Chloro-phenyl)-[1,2,4]thiadiazol-5-yl]-4-[2-(6-methoxy-pyridin-3-yl)-ethyl]-piperazine
1-[3-(3-Chloro-phenyl)-[1,2,4]thiadiazol-5-yl]-4-[2-(2-methoxy-pyridin-4-yl)-ethyl]-piperazine
1-[3-(3-Fluoro-phenyl)-[1,2,4]thiadiazol-5-yl]-4-[2-(2-methoxy-pyridin-4-yl)-ethyl]-piperazine
1-[3-(5-Chloro-pyridin-3-yl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(6-methoxy-pyridin-3-yl)-ethyl]-piperazine
1-[3-(6-Methyl-pyridin-3-yl)-[1,2,4]thiadiazol-5-yl]-4-phenethyl-piperazine
1-[2-(4-Methoxy-phenyl)-ethyl]-4-[3-(6-methyl-pyridin-3-yl)-[1,2,4]thiadiazol-5-yl]-piperazine
1-[2-(4-Fluoro-phenyl)-ethyl]-4-[3-(6-methyl-pyridin-3-yl)-[1,2,4]thiadiazol-5-yl]-piperazine
1-[2-(2-Methoxy-pyridin-4-yl)-ethyl]-4-[3-(6-methyl-pyridin-3-yl)-[1,2,4]thiadiazol-5-yl]-piperazine
1-[2-(4-Chloro-phenyl)-ethyl]-4-[3-(6-methyl-pyridin-3-yl)-[1,2,4]thiadiazol-5-yl]-piperazine
1-[3-(3-Fluoro-phenyl)-[1,2,4]thiadiazol-5-yl]-4-[2-(6-methoxy-pyridin-3-yl)-ethyl]-piperazine
1-[3-(3,4-Difluoro-phenyl)-[1,2,4]thiadiazol-5-yl]-4-[2-(6-methoxy-pyridin-3-yl)-ethyl]-piperazine
1-[3-(3,4-Difluoro-phenyl)-[1,2,4]thiadiazol-5-yl]-4-[2-(2-methoxy-pyridin-4-yl)-ethyl]-piperazine
4-(5-{4-[2-(6-Methoxy-pyridin-3-yl)-ethyl]-piperazin-1-yl}-[1,2,4]thiadiazol-3-yl)-benzonitrile
3-(5-{4-[2-(6-Methoxy-pyridin-3-yl)-ethyl]-piperazin-1-yl}-[1,2,4]thiadiazol-3-yl)-benzonitrile
4-(5-{4-[2-(2-Methoxy-pyridin-4-yl)-ethyl]-piperazin-1-yl}-[1,2,4]thiadiazol-3-yl)-benzonitrile
3-(5-{4-[2-(2-Methoxy-pyridin-4-yl)-ethyl]-piperazin-1-yl}-[1,2,4]thiadiazol-3-yl)-benzonitrile
1-[3-(4-Chloro-pyridin-2-yl)-[1,2,4]thiadiazol-5-yl]-4-phenethyl-piperazine
1-[3-(5-Chloro-pyridin-2-yl)-[1,2,4]thiadiazol-5-yl]-4-phenethyl-piperazine
1-[3-(4-Chloro-pyridin-2-yl)-[1,2,4]thiadiazol-5-yl]-4-[2-(4-fluoro-phenyl)-ethyl]-piperazine
1-[2-(4-Chloro-phenyl)-ethyl]-4-[3-(4-chloro-pyridin-2-yl)-[1,2,4]thiadiazol-5-yl]-piperazine
1-[2-(4-Chloro-phenyl)-ethyl]-4-[3-(5-chloro-pyridin-2-yl)-[1,2,4]thiadiazol-5-yl]-piperazine
1-[3-(4-Chloro-pyridin-2-yl)-[1,2,4]thiadiazol-5-yl]-4-[2-(4-methoxy-phenyl)-ethyl]-piperazine
1-[3-(5-Chloro-pyridin-2-yl)-[1,2,4]thiadiazol-5-yl]-4-[2-(4-methoxy-phenyl)-ethyl]-piperazine
1-[3-(4-Chloro-pyridin-2-yl)-[1,2,4]thiadiazol-5-yl]-4-[2-(2-methoxy-pyridin-4-yl)-ethyl]-piperazine
1-[3-(4-Chloro-pyridin-2-yl)-[1,2,4]thiadiazol-5-yl]-4-(2-methyl-benzyl)-piperazine
1-[3-(5-Chloro-pyridin-2-yl)-[1,2,4]thiadiazol-5-yl]-4-(2-methyl-benzyl)-piperazine
1-[3-(5-Chloro-pyridin-3-yl)-[1,2,4]thiadiazol-5-yl]-4-phenethyl-piperazine
1-[3-(5-Chloro-pyridin-3-yl)-[1,2,4]thiadiazol-5-yl]-4-[2-(4-fluoro-phenyl)-ethyl]-piperazine
1-[2-(4-Chloro-phenyl)-ethyl]-4-[3-(5-chloro-pyridin-3-yl)-[1,2,4]thiadiazol-5-yl]-piperazine
1-[3-(5-Chloro-pyridin-3-yl)-[1,2,4]thiadiazol-5-yl]-4-[2-(2-methoxy-pyridin-4-yl)-ethyl]-piperazine
1-[3-(5-Chloro-pyridin-2-yl)-[1,2,4]thiadiazol-5-yl]-4-[2-(3,4-difluoro-phenyl)-ethyl]-piperazine
1-[2-(3,4-Difluoro-phenyl)-ethyl]-4-[3-(6-methyl-pyridin-3-yl)-[1,2,4]thiadiazol-5-yl]-piperazine
1-[3-(5-Chloro-pyridin-3-yl)-[1,2,4]thiadiazol-5-yl]-4-[2-(3-trifluoromethyl-phenyl)-ethyl]-piperazine
1-(2-Methyl-benzyl)-4-[3-(6-methyl-pyridin-3-yl)-[1,2,4]thiadiazol-5-yl]-piperazine
1-[3-(5-Chloro-pyridin-3-yl)-[1,2,4]thiadiazol-5-yl]-4-(2-methyl-benzyl)-piperazine
1-[3-(5-Chloro-pyridin-3-yl)-[1,2,4]thiadiazol-5-yl]-4-[2-(4-trifluoromethyl-phenyl)-ethyl]-piperazine.
3-(4-chloropyridin-2-yl)-5-(4-(3,4-difluorophenethyl)piperazin-1-yl)-1,2,4-thiadiazole 3-(4-chloropyridin-2-yl)-5-(4-(3-(trifluoromethyl)phenethyl)piperazin-1-yl)-1,2,4-thiadiazole 3-(5-chloropyridin-3-yl)-5-(4-(3,4-difluorophenethyl)piperazin-1-yl)-1,2,4-thiadiazole 3-(2-chloropyridin-4-yl)-5-(4-(2-(2-methoxypyridin-4-yl)ethyl)piperazin-1-yl)-1,2,4-thiadiazole 5-(4-(4-chlorophenethyl)piperazin-1-yl)-3-(2-chloropyridin-4-yl)-1,2,4-thiadiazole 3-(2-chloropyridin-4-yl)-5-(4-phenethylpiperazin-1-yl)-1,2,4-thiadiazole 3-(2-methylpyridin-4-yl)-5-(4-phenethylpiperazin-1-yl)-1,2,4-thiadiazole or 5-(4-(2-(2-methoxypyridin-4-yl)ethyl)piperazin-1-yl)-3-(2-methylpyridin-4-yl)-1,2,4-thiadiazole.

One further embodiment of the invention are compounds of formula IA, wherein $C^2$ is cycloalkyl, for example the following compounds 1-(2-Cyclohexyl-ethyl)-4-[3-(3,4-difluoro-phenyl)-[1,2,4]thiadiazol-5-yl]-piperazine 1-(2-Cyclohexyl-ethyl)-4-[3-(3-fluoro-phenyl)-[1,2,4]thiadiazol-5-yl]-piperazine 3-(4-chlorophenyl)-5-(4-(2-cyclohexylethyl)piperazin-1-yl)-1,2,4-thiadiazole or 3-(3-chlorophenyl)-5-(4-(2-cyclohexylethyl)piperazin-1-yl)-1,2,4-thiadiazole.

One further embodiment of the invention are compounds of formula IA, wherein $C^2$ is piperidin-lyl, for example the following compound 3-(5-chloropyridin-3-yl)-5-(4-(2-(piperidin-1-yl)ethyl)piperazin-1-yl)-1,2,4-thiadiazole.

One further embodiment of the invention are compounds of formula IA, wherein $C^2$ is tetrahydro-2H-pyran-4-yl, for example the following compounds 3-(3,4-difluorophenyl)-5-(4-(2-(tetrahydro-2H-pyran-4-yl)ethyl)piperazin-1-yl)-1,2,4-thiadiazole 3-(3-chlorophenyl)-5-(4-(2-(tetrahydro-2H-pyran-4-yl)ethyl)piperazin-1-yl)-1,2,4-thiadiazole 3-(5-chloropyridin-3-yl)-5-(4-(2-(tetrahydro-2H-pyran-4-yl)ethyl)piperazin-1-yl)-1,2,4-thiadiazole or 3-(4-chlorophenyl)-5-(4-(2-(tetrahydro-2H-pyran-4-yl)ethyl)piperazin-1-yl)-1,2,4-thiadiazole.

One further embodiment of the invention are compounds of formula IA, wherein $C^1$ is pyridazin-4-yl, for example the following compounds 3-(6-methylpyridazin-4-yl)-5-(4-phenethylpiperazin-1-yl)-1,2,4-thiadiazole 5-(4-(4-fluorophenethyl)piperazin-1-yl)-3-(6-methylpyridazin-4-yl)-1,2,4-thiadiazole 5-(4-(3,4-difluorophenethyl)piperazin-1-yl)-3-(6-methylpyridazin-4-yl)-1,2,4-thiadiazole 5-(4-(2-(2-methoxypyridin-4-yl)ethyl)piperazin-1-yl)-3-(6-methylpyridazin-4-yl)-1,2,4-thiadiazole or 5-(4-(4-methoxyphenethyl)piperazin-1-yl)-3-(6-methylpyridazin-4-yl)-1,2,4-thiadiazole.

One further embodiment of the invention are compounds of formula IA, wherein $C^1$ is pyrimidin-5-yl, for example the following compounds 3-(2-methylpyrimidin-5-yl)-5-(4-phenethylpiperazin-1-yl)-1,2,4-thiadiazole 5-(4-(4-methoxyphenethyl)piperazin-1-yl)-3-(2-methylpyrimidin-5-yl)-1,2,4-thiadiazole 5-(4-(4-chlorophenethyl)piperazin-1-yl)-3-(2-methylpyrimidin-5-yl)-1,2,4-thiadiazole 5-(4-(4-fluorophenethyl)piperazin-1-yl)-3-(2-methylpyrimidin-5-yl)-1,2,4-thiadiazole 5-(4-(3,4-difluorophenethyl)piperazin-1-yl)-3-(2-methylpyrimidin-5-yl)-1,2,4-thiadiazole or 5-(4-(2-(2-methoxypyridin-4-yl)ethyl)piperazin-1-yl)-3-(2-methylpyrimidin-5-yl)-1,2,4-thiadiazole.

One embodiment of the invention are compounds of formula I, wherein $A^1$ and $A^2$ are both phenyl, for example the following compounds 1-(2,4-Dichloro-benzyl)-4-(3-p-tolyl-[1,2,4]thiadiazol-5-yl)-piperazine; 1-Phenethyl-4-(3-p-tolyl-[1,2,4]thiadiazol-5-yl)-piperazine; 1-[2-(3,4-Dichloro-phenyl)-ethyl]-4-(3-p-tolyl-[1,2,4]thiadiazol-5-yl)-piperazine; 1-(2-Methyl-benzyl)-4-(3-p-tolyl-[1,2,4]thiadiazol-5-yl)-piperazine; 1-[3-(4-Chloro-phenyl)-[1,2,4]thiadiazol-5-yl]-4-(2-methyl-benzyl)-piperazine; 1-[3-(3-Methoxy-phenyl)-[1,2,4]thiadiazol-5-yl]-4-(2-methyl-benzyl)-piperazine; 1-[3-(4-Chloro-phenyl)-[1,2,4]thiadiazol-5-yl]-4-[2-(3-methoxy-phenyl)-ethyl]-piperazine; 1-[2-(3-Methoxy-phenyl)-ethyl]-4-[3-(3-methoxy-phenyl)-[1,2,4]thiadiazol-5-yl]-piperazine; 1-[2-(3-Methoxy-phenyl)-ethyl]-4-(3-p-tolyl-[1,2,4]thiadiazol-5-yl)-piperazine; 1-[3-(4-Chloro-phenyl)-[1,2,4]thiadiazol-5-yl]-4-[2-(4-methoxy-phenyl)-ethyl]-piperazine; 1-[2-(4-Methoxy-phenyl)-ethyl]-4-[3-(3-methoxy-phenyl)-[1,2,4]thiadiazol-5-yl]-piperazine; 1-[2-(4-Methoxy-phenyl)-ethyl]-4-(3-p-tolyl-[1,2,4]thiadiazol-5-yl)-piperazine; 1-[3-(4-Chloro-phenyl)-[1,2,4]thiadiazol-5-yl]-4-[2-(3-fluoro-phenyl)-ethyl]-piperazine; 1-[2-(3-Chloro-phenyl)-ethyl]-4-[3-(4-chloro-phenyl)-[1,2,4]thiadiazol-5-yl]-piperazine; 1-[3-(4-Chloro-phenyl)-[1,2,4]thiadiazol-5-yl]-4-(2-m-tolyl-ethyl)-piperazine; 1-[3-(4-Chloro-phenyl)-[1,2,4]thiadiazol-5-yl]-4-[2-(4-fluoro-phenyl)-ethyl]-piperazine; 1-[2-(4-Chloro-phenyl)-ethyl]-4-[3-(4-chloro-phenyl)-[1,2,4]thiadiazol-5-yl]-piperazine; 1-[3-(4-Chloro-phenyl)-[1,2,4]thiadiazol-5-yl]-4-(2-p-tolyl-ethyl)-piperazine; 1-[3-(4-Chloro-phenyl)-[1,2,4]thiadiazol-5-yl]-4-[2-(2-methoxy-phenyl)-ethyl]-piperazine; 1-[3-(4-Chloro-phenyl)-[1,2,4]thiadiazol-5-yl]-4-[2-(2-fluoro-phenyl)-ethyl]-piperazine; 1-[2-(2-Chloro-phenyl)-ethyl]-4-[3-(4-chloro-phenyl)-[1,2,4]thiadiazol-5-yl]-piperazine; 1-[3-(3,5-Dichloro-phenyl)-[1,2,4]thiadiazol-5-yl]-4-[2-(3-methoxy-phenyl)-ethyl]-piperazine; 1-[3-(4-Chloro-phenyl)-[1,2,4]thiadiazol-5-yl]-4-[3-(3-methoxy-phenyl)-propyl]-piperazine; 1-[3-(4-Fluoro-phenyl)-[1,2,4]thiadiazol-5-yl]-4-[2-(3-methoxy-phenyl)-ethyl]-piperazine; 1-[2-(3-Methoxy-phenyl)-ethyl]-4-[3-(2-methoxy-phenyl)-[1,2,4]thiadiazol-5-yl]-piperazine; 1-[2-(3-Methoxy-phenyl)-ethyl]-4-[3-(4-trifluoromethoxy-phenyl)-[1,2,4]thiadiazol-5-yl]-piperazine; 1-[2-(4-Methoxy-phenyl)-ethyl]-4-[3-(4-trifluoromethoxy-phenyl)-[1,2,4]thiadiazol-5-yl]-piperazine; 1-[3-(4-Chloro-phenyl)-[1,2,4]thiadiazol-5-yl]-4-[2-(3-trifluoromethoxy-phenyl)-ethyl]-piperazine; 1-[3-(4-Chloro-phenyl)-[1,2,4]thiadiazol-5-yl]-4-[3-(2-methoxy-phenyl)-propyl]-piperazine; 1-[2-(4-Methoxy-phenyl)-ethyl]-4-[3-(4-methoxy-phenyl)-[1,2,4]thiadiazol-5-yl]-piperazine; 1-[3-(3-Chloro-phenyl)-[1,2,4]thiadiazol-5-yl]-4-[2-(4-methoxy-phenyl)-ethyl]-piperazine 1-[2-(4-Methoxy-phenyl)-ethyl]-4-[3-(2-methoxy-phenyl)-[1,2,4]thiadiazol-5-yl]-piperazine; 1-[3-(3,5-Dichloro-phenyl)-[1,2,4]thiadiazol-5-yl]-4-[2-(4-methoxy-phenyl)-ethyl]-piperazine; 1-[3-(4-Fluoro-phenyl)-[1,2,4]thiadiazol-5-yl]-4-[2-(4-methoxy-phenyl)-ethyl]-piperazine 1-[3-(3-Chloro-phenyl)-[1,2,4]thiadiazol-5-yl]-4-[2-(3-methoxy-phenyl)-ethyl]-piperazine 1-[2-(3-Methoxy-phenyl)-ethyl]-4-[3-(4-methoxy-phenyl)-[1,2,4]thiadiazol-5-yl]-piperazine; 1-[3-(4-Chloro-phenyl)-[1,2,4]thiadiazol-5-yl]-4-[2-(4-ethoxy-phenyl)-ethyl]-piperazine 1-[3-(4-Chloro-phenyl)-[1,2,4]thiadiazol-5-yl]-4-[2-(3-isopropoxy-phenyl)- ethyl]-piperazine; 1-[3-(4-Chloro-phenyl)-[1,2,4]thiadiazol-5-yl]-4-[3-(4-methoxy-phenyl)-propyl]-piperazine; 2-{4-[3-(4-Chloro-phenyl)-[1,2,4]thiadiazol-5-yl]-piperazin-1-yl}-1-(4-methoxy-phenyl)-ethanone; 2-{4-[3-(4-Chloro-phenyl)-[1,2,4]thiadiazol-5-yl]-piperazin-1-yl}-1-(4-methoxy-phenyl)-ethanol; 1-[3-(4-Chloro-2-fluoro-phenyl)-[1,2,4]thiadiazol-5-yl]-4-[2-(3-methoxy-phenyl)-ethyl]-piperazine; 1-[3-(4-Chloro-2-fluoro-phenyl)-[1,2,4]thiadiazol-5-yl]-4-[2-(4-methoxy-phenyl)-ethyl]-piperazine; 1-[3-(2-Chloro-phenyl)-[1,2,4]thiadiazol-5-yl]-4-[2-(3-methoxy-phenyl)-ethyl]-piperazine 1-[3-(2-Chloro-phenyl)-[1,2,4]thiadiazol-5-yl]-4-[2-(4-methoxy-phenyl)-ethyl]-piperazine 1-[3-(4-Chloro-phenyl)-[1,2,4]thiadiazol-5-yl]-4-[2-(4-methoxy-phenyl)-allyl]-piperazine 2-{4-[3-(4-Chloro-phenyl)-[1,2,4]thiadiazol-5-yl]-piperazin-1-yl}-1-(3-methoxy-phenyl)-ethanone; 2-{4-[3-(4-Chloro-phenyl)-[1,2,4]thiadiazol-5-yl]-piperazin-1-yl}-1-(3-methoxy-phenyl)-ethanol; 2-{4-[3-(4-Chloro-phenyl)-[1,2,4]thiadiazol-5-yl]-piperazin-1-yl}-1-(3-fluoro-phenyl)-ethanone; 2-{4-[3-(4-Chloro-phenyl)-[1,2,4]thiadiazol-5-yl]-piperazin-1-yl}-1-(3-fluoro-phenyl)-ethanol; 1-[3-(4-Chloro-phenyl)-[1,2,4]thiadiazol-5-yl]-4-[2-fluoro-2-(4-methoxy-phenyl)-ethyl]-piperazine; 1-[3-(4-Chloro-phenyl)-[1,2,4]thiadiazol-5-yl]-4-[2-fluoro-2-(3-methoxy-phenyl)-ethyl]-piperazine; 1-[3-(4-Fluoro-2-methoxy-phenyl)-[1,2,4]thiadiazol-5-yl]-4-[2-(3-methoxy-phenyl)-ethyl]-piperazine; 1-[3-(4-Fluoro-2-methoxy-phenyl)-[1,2,4]thiadiazol-5-yl]-4-[2-(4-methoxy-phenyl)-ethyl]-piperazine; 1-[1-(4-Chloro-phenyl)-cyclopropylmethyl]-4-[3-(4-chloro-phenyl)-[1,2,4]thiadiazol-5-yl]-piperazine; 1-[3-(4-Chloro-phenyl)-[1,2,4]thiadiazol-5-yl]-4-[2-(3-difluoromethoxy-phenyl)-ethyl]-piperazine; 1-[3-(4-Chloro-phenyl)-[1,2,4]thiadiazol-5-yl]-4-[2-(4-difluoromethoxy-phenyl)-ethyl]-piperazine; 1-[3-(4-Chloro-phenyl)-[1,2,4]thiadiazol-5-yl]-4-[2-(4-isopropoxy-phenyl)-ethyl]-piperazine; 1-[3-(4-Chloro-phenyl)-[1,2,4]thiadiazol-5-yl]-4-[2-(4-methoxy-phenyl)-propyl]-piperazine; 1-[3-(4-Chloro-phenyl)-[1,2,4]thiadiazol-5-yl]-4-[2-(4-methoxy-phenyl)-1-methyl-ethyl]-piperazine; 4-(5-{4-[2-(4-Methoxy-phenyl)-ethyl]-piperazin-1-yl}-[1,2,4]thiadiazol-3-yl)-benzonitrile; 1-[3-(4-Chloro-phenyl)-[1,2,4]thiadiazol-5-yl]-4-[2-(3-fluoro-4-methoxy-phenyl)-ethyl]-piperazine; 3-(5-{4-[2-(4-Methoxy-phenyl)-ethyl]-piperazin-1-yl}-[1,2,4]thiadiazol-3-yl)-benzonitrile; 1-[3-(3-Chloro-phenyl)-[1,2,4]thiadiazol-5-yl]-4-phenethyl-piperazine; 1-[3-(3-Fluoro-phenyl)-[1,2,4]thiadiazol-5-yl]-4-phenethyl-piperazine; 1-[3-(3-Fluoro-phenyl)-[1,2,4]thiadiazol-5-yl]-4-[2-(4-methoxy-phenyl)-ethyl]-piperazine; 1-[3-(3-Chloro-phenyl)-[1,2,4]thiadiazol-5-yl]-4-[2-(4-fluoro-phenyl)-ethyl]-piperazine; 1-[2-(4-Fluoro-phenyl)-ethyl]-4-[3-(3-fluoro-phenyl)-[1,2,4]thiadiazol-5-yl]-piperazine; 1-[2-(4-Chloro-phenyl)-ethyl]-4-[3-(3-chloro-phenyl)-[1,2,4]thiadiazol-5-yl]-piperazine; 1-[2-(4-Chloro-phenyl)-ethyl]-4-[3-(3-fluoro-phenyl)-[1,2,4]thiadiazol-5-yl]-piperazine; 1-[3-(3-Chloro-phenyl)-[1,2,4]thiadiazol-5-yl]-4-(2-methyl-benzyl)-piperazine; 1-[3-(3-Fluoro-phenyl)-[1,2,4]thiadiazol-5-yl]-4-(2-methyl-benzyl)-piperazine; 1-[3-(3,4-Difluoro-phenyl)-[1,2,4]thiadiazol-5-yl]-4-phenethyl-piperazine; 1-[3-(3,4-Difluoro-phenyl)-[1,2,4]thiadiazol-5-yl]-4-[2-(4-methoxy-phenyl)-ethyl]-piperazine; 1-[3-(3,4-Difluoro-phenyl)-[1,2,4]thiadiazol-5-yl]-4-[2-(4-fluoro-phenyl)-ethyl]-piperazine; 1-[2-(4-Chloro-phenyl)-ethyl]-4-[3-(3,4-difluoro-phenyl)-[1,2,4]thiadiazol-5-yl]-piperazine; 1-[3-(3,4-Difluoro-phenyl)-[1,2,4]thiadiazol-5-yl]-4-(2-methyl-benzyl)-piperazine; 4-[5-(4-Phenethyl-piperazin-1-yl)-[1,2,4]thiadiazol-3-yl]-benzonitrile; 3-[5-(4-Phenethyl-piperazin-1-yl)-[1,2,4]thiadiazol-3-yl]-benzonitrile; 4-(5-{4-[2-(4-Fluoro-phenyl)-ethyl]-piperazin-1-yl}-[1,2,4]thiadiazol-3-yl)-benzonitrile; 3-(5-{4-[2-(4-Fluoro-phenyl)-ethyl]-piperazin-1-yl}-[1,2,4]thiadiazol-3-yl)-benzonitrile; 4-(5-{4-[2-(4-Chloro-phenyl)-ethyl]-piperazin-1-yl}-[1,2,4]thiadiazol-3-yl)-benzonitrile; 3-(5-{4-[2-(4-Chloro-phenyl)-ethyl]-piperazin-1-yl}-[1,2,4]thiadiazol-3-yl)-benzonitrile; 4-{5-[4-(2-Methyl-benzyl)-piperazin-1-yl]-[1,2,4]thiadiazol-3-yl}-benzonitrile; 3-{5-[4-(2-Methyl-benzyl)-piperazin-1-yl]-[1,2,4]thiadiazol-3-yl}-benzonitrile; 1-[3-(4-Chloro-phenyl)-[1,2,4]thiadiazol-5-yl]-4-[2-(3,4-difluoro-phenyl)-ethyl]-piperazine; 1-[3-(3-Chloro-phenyl)-[1,2,4]thiadiazol-5-yl]-4-[2-(3,4-difluoro-phenyl)-ethyl]-piperazine; 1-[2-(3,4-Difluoro-phenyl)-ethyl]-4-[3-(3,4-difluoro-phenyl)-[1,2,4]thiadiazol-5-yl]-piperazine; 3-(5-{4-[2-(3,4-Difluoro-phenyl)-ethyl]-piperazin-1-yl}-[1,2,4]thiadiazol-3-yl)-benzonitrile; 4-(5-{4-[2-(3,4-Difluoro-phenyl)-ethyl]-piperazin-1-yl}-[1,2,4]thiadiazol-3-yl)-benzonitrile; 1-[3-(4-Chloro-phenyl)-[1,2,4]thiadiazol-5-yl]-4-[2-(3-trifluoromethyl-phenyl)-ethyl]-piperazine; 1-[3-(3-Fluoro-phenyl)-[1,2,4]thiadiazol-5-yl]-4-[2-(3-trifluoromethyl-phenyl)-ethyl]-piperazine; 1-[3-(3-Chloro-phenyl)-[1,2,4]thiadiazol-5-yl]-4-[2-(3-trifluoromethyl-phenyl)-ethyl]-piperazine; 4-(5-{4-[2-(3-Trifluoromethyl-phenyl)-ethyl]-piperazin-1-yl}-[1,2,4]thiadiazol-3-yl)-benzonitrile; 1-[3-(4-Chloro-phenyl)-[1,2,4]thiadiazol-5-yl]-4-[2-(4-trifluoromethyl-phenyl)-ethyl]-piperazine; 1-[3-(3-Chloro-phenyl)-[1,2,4]thiadiazol-5-yl]-4-[2-(4-trifluoromethyl-phenyl)-ethyl]-piperazine; 1-[3-(3,4-Difluoro-phenyl)-[1,2,4]thiadiazol-5-yl]-4-[2-(4-trifluoromethyl-phenyl)-ethyl]-piperazine; or 4-(5-{4-[2-(4-Trifluoromethyl-phenyl)-ethyl]-piperazin-1-yl}-[1,2,4]thiadiazol-3-yl)-benzonitrile.

One further embodiment of the invention are compounds of formula I, wherein at least one of $A^1$ or $A^2$ is pyridine-2-yl, pyridine-3-yl or pyridine-4-yl, for example the following compounds: 1-[2-(3-Methoxy-phenyl)-ethyl]-4-(3-pyridin-4-yl-[1,2,4]thiadiazol-5-yl)-piperazine; 1-[2-(3-Methoxy-phenyl)-ethyl]-4-[3-(6-trifluoromethyl-pyridin-3-yl)-[1,2,4]thiadiazol-5-yl]-piperazine; 1-[2-(4-Methoxy-phenyl)-ethyl]-4-[3-(6-trifluoromethyl-pyridin-3-yl)-[1,2,4]thiadiazol-5-yl]-piperazine; 1-[2-(4-Methoxy-phenyl)-ethyl]-4-(3-pyridin-4-yl-[1,2,4]thiadiazol-5-yl)-piperazine; 1-[3-(4-Chloro-phenyl)-[1,2,4]thiadiazol-5-yl]-4-[2-(2-methoxy-pyridin-4-yl)-ethyl]-piperazine; 1-[3-(4-Chloro-phenyl)-[1,2,4]thiadiazol-5-yl]-4-[2-(6-methoxy-pyridin-3-yl)-ethyl]-piperazine 1-[3-(3-Chloro-phenyl)-[1,2,4]thiadiazol-5-yl]-4-[2-(2-methoxy-pyridin-4-yl)-ethyl]-piperazine; 1 [3-(3-Fluoro-phenyl)-[1,2,4]thiadiazol-5-yl]-4-[2-(2-methoxy-pyridin-4-yl)-ethyl]-piperazine; 1-[3-(5-Chloro-pyridin-3-yl)-[1,2,4]thiadiazol-5-yl]-4-[2-(4-methoxy-phenyl)-ethyl]-piperazine; 1-[3-(3-Chloro-phenyl)-[1,2,4]thiadiazol-5-yl]-4-[2-(6-methoxy-pyridin-3-yl)-ethyl]-piperazine; 1-[3-(6-Methyl-pyridin-3-yl)-[1,2,4]thiadiazol-5-yl]-4-phenethyl-piperazine; 1-[2-(4-Methoxy-phenyl)-ethyl]-4-[3-(6-methyl-pyridin-3-yl)-[1,2,4]thiadiazol-5-yl]-piperazine; 1-[2-(4-Fluoro-phenyl)-ethyl]-4-[3-(6-methyl-pyridin-3-yl)-[1,2,4]thiadiazol-5-yl]-piperazine; 1-[2-(2-Methoxy-pyridin-4-yl)-ethyl]-4-[3-(6-methyl-pyridin-3-yl)-[1,2,4]thiadiazol-5-yl]-piperazine; 1-[2-(4-Chloro-phenyl)-ethyl]-4-[3-(6-methyl-pyridin-3-yl)-[1,2,4]thiadiazol-5-yl]-piperazine; 1-[3-(3-Fluoro-phenyl)-[1,2,4]thiadiazol-5-yl]-4-[2-(6-methoxy-pyridin-3-yl)-ethyl]-piperazine; 1-[3-(3,4-Difluoro-phenyl)-[1,2,4]thiadiazol-5-yl]-4-[2-(6-methoxy-pyridin-3-yl)-ethyl]- piperazine; 1-[3-(3,4-Difluoro-phenyl)-[1,2,4]thiadiazol-5-yl]-4-[2-(2-methoxy-pyridin-4-yl)-ethyl]-piperazine; 4-(5-{4-[2-(6-Methoxy-pyridin-3-yl)-ethyl]-piperazin-1-yl}-[1,2,4]thiadiazol-3-yl)-benzonitrile; 3-(5-{4-[2-(6-Methoxy-pyridin-3-yl)-ethyl]-piperazin-1-yl}-[1,2,4]thiadiazol-3-yl)-benzonitrile; 4-(5-{4-[2-(2-Methoxy-pyridin-4-yl)-ethyl]-piperazin-1-yl}-[1,2,4]thiadiazol-3-yl)-benzonitrile; 3-(5-{4-[2-(2-Methoxy-pyridin-4-yl)-ethyl]-piperazin-1-yl}-[1,2,4]thiadiazol-3-yl)-benzonitrile; 1-[3-(4-Chloro-pyridin-2-yl)-[1,2,4]thiadiazol-5-yl]-4-phenethyl-piperazine; 1-[3-(5-Chloro-pyridin-2-yl)-[1,2,4]thiadiazol-5-yl]-4-phenethyl-piperazine; 1-[3-(4-Chloro-pyridin-2-yl)-[1,2,4]thiadiazol-5-yl]-4-[2-(4-fluoro-phenyl)-ethyl]-piperazine; 1-[2-(4-Chloro-phenyl)-ethyl]-4-[3-(4-chloro-pyridin-2-yl)-[1,2,4]thiadiazol-5-yl]-piperazine; 1-[2-(4-Chloro-phenyl)-ethyl]-4-[3-(5-chloro-pyridin-2-yl)-[1,2,4]thiadiazol-5-yl]-piperazine; 1-[3-(4-Chloro-pyridin-2-yl)-[1,2,4]thiadiazol-5-yl]-4-[2-(4-methoxy-phenyl)-ethyl]-piperazine; 1-[3-(5-Chloro-pyridin-2-yl)-[1,2,4]thiadiazol-5-yl]-4-[2-(4-methoxy-phenyl)-ethyl]-piperazine; 1-[3-(4-Chloro-pyridin-2-yl)-[1,2,4]thiadiazol-5-yl]-4-[2-(2-methoxy-pyridin-4-yl)-ethyl]-piperazine; 1-[3-(4-Chloro-pyridin-2-yl)-[1,2,4]thiadiazol-5-yl]-4-(2-methyl-benzyl)-piperazine; 1-[3-(5-Chloro-pyridin-2-yl)-[1,2,4]thiadiazol-5-yl]-4-(2-methyl-benzyl)-piperazine; 1-[3-(5-Chloro-pyridin-3-yl)-[1,2,4]thiadiazol-5-yl]-4-phenethyl-piperazine; 1-[3-(5-Chloro-pyridin-3-yl)-[1,2,4]thiadiazol-5-yl]-4-[2-(4-fluoro-phenyl)-ethyl]-piperazine; 1-[2-(4-Chloro-phenyl)-ethyl]-4-[3-(5-chloro-pyridin-3-yl)-[1,2,4]thiadiazol-5-yl]-piperazine; 1-[3-(5-Chloro-pyridin-3-yl)-[1,2,4]thiadiazol-5-yl]-4-[2-(2-methoxy-pyridin-4-yl)-ethyl]-piperazine; 1-[3-(5-Chloro-pyridin-2-yl)-[1,2,4]thiadiazol-5-yl]-4-[2-(3,4-difluoro-phenyl)-ethyl]-piperazine; 1-[2-(3,4-Difluoro-phenyl)-ethyl]-4-[3-(6-methyl-pyridin-3-yl)-[1,2,4]thiadiazol-5-yl]-piperazine; 1-[3-(5-Chloro-pyridin-3-yl)-[1,2,4]thiadiazol-5-yl]-4-[2-(3-trifluoromethyl-phenyl)-ethyl]-piperazine; 1-(2-Methyl-benzyl)-4-[3-(6-methyl-pyridin-3-yl)-[1,2,4]thiadiazol-5-yl]-piperazine; 1-[3-(5-Chloro-pyridin-3-yl)-[1,2,4]thiadiazol-5-yl]-4-(2-methyl-benzyl)-piperazine; or 1-[3-(5-Chloro-pyridin-3-yl)-[1,2,4]thiadiazol-5-yl]-4-[2-(4-trifluoromethyl-phenyl)-ethyl]-piperazine.

One further embodiment of the invention are compounds of formula I, wherein one of $A^1$ or $A^2$ is benzo[1,3]dioxol, for example the following compound: 1-Benzo[1,3]dioxol-5-yl-methyl-4-(3-p-tolyl-[1,2,4]thiadiazol-5-yl)-piperazine.

One further embodiment of the invention are compounds of formula I, wherein at least one of $A^1$ or $A^2$ is thiophen-2-yl, for example the following compounds: 1-[2-(3-Methoxy-phenyl)-ethyl]-4-(3-thiophen-2-yl-[1,2,4]thiadiazol-5-yl)-piperazine or 1-[2-(4-Methoxy-phenyl)-ethyl]-4-(3-thiophen-2-yl-[1,2,4]thiadiazol-5-yl)-piperazine.

One further embodiment of the invention are compounds of formula I, wherein at least one of $A^1$ or $A^2$ are pyrazine-2-yl, for example the following compounds: 2-(5-{4-[2-(4-Methoxy-phenyl)-ethyl]-piperazin-1-yl}-[1,2,4]thiadiazol-3-yl)-pyrazine; or 2-(5-{4-[2-(3-Methoxy-phenyl)-ethyl]-piperazin-1-yl}-[1,2,4]thiadiazol-3-yl)-pyrazine.

One further embodiment of the invention are compounds of formula I, wherein $A^2$ is cycloalkyl, for example the following compounds: 1-(2-Cyclohexyl-ethyl)-4-[3-(3,4-difluoro-phenyl)-[1,2,4]thiadiazol-5-yl]-piperazine; or 1-(2-Cyclohexyl-ethyl)-4-[3-(3-fluoro-phenyl)-[1,2,4]thiadiazol-5-yl]-piperazine.

The present compounds of formula IA or I, and their pharmaceutically acceptable salts can be prepared by methods known in the art, for example, by processes described below, which process comprises
coupling a compound of formula

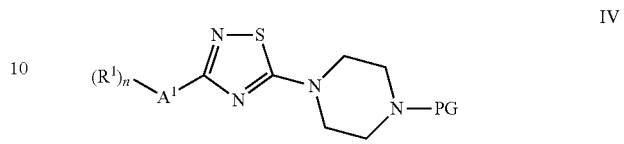

with a compound of formula

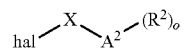

to give a compound of formula

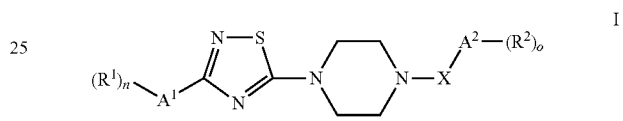

wherein PG is hydrogen or a protecting group such as tert-butyloxycarbonyl (BOC), 9-fluorenylmethyloxycarbonyl (FMOC) and the like, and hal is halogen such as chloro, bromo, fluoro, or iodo, wherein the definitions are as described above, or if desired, converting the compounds obtained into pharmaceutically acceptable acid addition salts. In an embodiment, $A^1$ has the same meaning as defined for $C^1$, and $A^2$ has the same meaning as defined for $C^2$.

General Experimental Part

The preparation of compounds of formula IA or I of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary.

In more detail, the compounds of formula IA or I can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux.

The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

romethyl mercaptan with a base (NEt$_3$, DIPEA and the like) to afford chloro-thiadiazole derivatives III.

b) Chloro-thiadiazole derivatives III are conveniently reacted with either substituted piperazine derivatives to directly access final thiadiazole derivatives I or alternatively III is reacted with a protected piperazine (PG=Boc, and the like) to afford thiadiazole derivatives IV.

c) Deprotection of IV is done under suitable conditions, in case of PG=Boc under acidic conditions, to yield the free piperazine derivatives which are conveniently reacted with suitable electrophiles to access final thiadiazole derivatives I

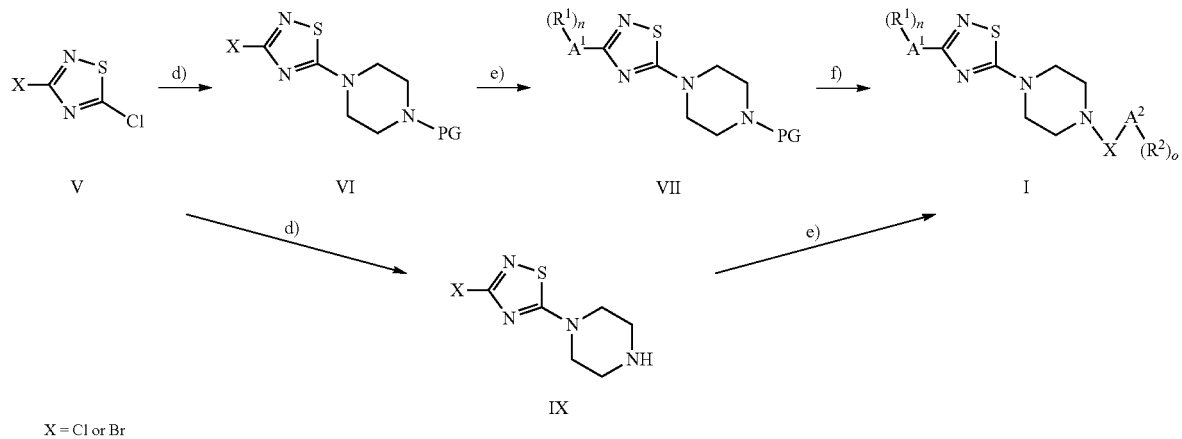

X = Cl or Br

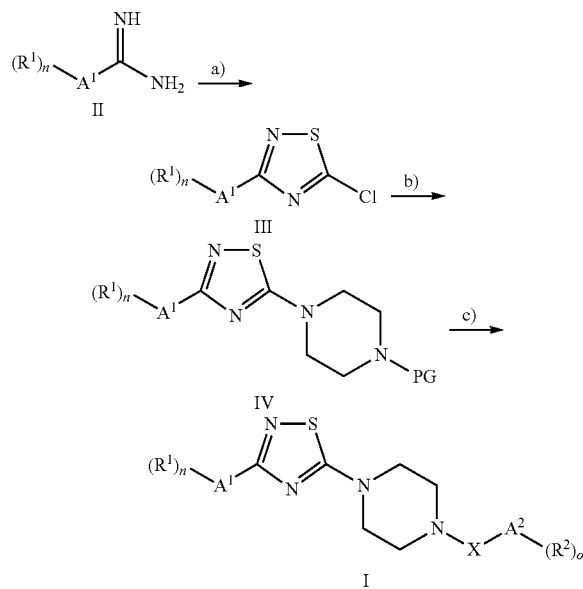

In an embodiment, $A^1$ has the same meaning as defined for $C^1$, and $A^2$ has the same meaning as defined for $C^2$.

a) Amidines II are either commercially available or can be synthesized according to methods known in the art. These amidine derivatives II are conveniently reacted with perchlod) 3-Bromo-5-chloro-1,2,4-thiadiazole and 3,5-dichloro-1,2,4-thiadiazole V are commercially available and can conveniently be reacted with protected (PG=Boc and the like) or substituted piperazines to yield thiadiazole derivatives VI or IX.

e) Thiadiazole derivatives VI or IX are conveniently reacted under Palladium catalysis with suitable boronic acids or esters to yield in case of IX the final derivatives I or in case of VI the protected thiadiazole derivatives VII.

f) Deprotection of VII is done under suitable conditions, in case of PG=Boc under acidic conditions, to yield the free piperazine derivatives which are conveniently reacted with suitable electrophiles to access final thiadiazole derivatives I.

EXPERIMENTAL PART

Abbreviations

DCM=dichloromethane;
DAST=dimethylaminosulfur trifluoride;
DIPEA=N,N-diisopropylethylamine;
DME=dimethoxyethane;
EtOH=ethanol;
EtOAc=ethyl acetate;
HPLC=high pressure liquid chromatography;
MeCN=Acetonitrile;
MeOH=methanol;
RT=room temperature;
THF=Tetrahydrofuran Exemplary compounds of the present invention are listed in table II.

TABLE 2

| Example | Chemical name |
| --- | --- |
| 2 | 1-Benzo[1,3]dioxol-5-ylmethyl-4-(3-p-tolyl-[1,2,4]thiadiazol-5-yl)-piperazine |
| 3 | 1-(2,4-Dichloro-benzyl)-4-(3-p-tolyl-[1,2,4]thiadiazol-5-yl)-piperazine |
| 4 | 1-Phenethyl-4-(3-p-tolyl-[1,2,4]thiadiazol-5-yl)-piperazine |
| 5 | 1-[2-(3,4-Dichloro-phenyl)-ethyl]-4-(3-p-tolyl-[1,2,4]thiadiazol-5-yl)-piperazine |
| 6 | 1-(2-Methyl-benzyl)-4-(3-p-tolyl-[1,2,4]thiadiazol-5-yl)-piperazine |
| 12 | 1-[3-(4-Chloro-phenyl)-[1,2,4]thiadiazol-5-yl]-4-(2-methyl-benzyl)-piperazine |
| 13 | 1-[3-(3-Methoxy-phenyl)-[1,2,4]thiadiazol-5-yl]-4-(2-methyl-benzyl)-piperazine |
| 14 | 1-[3-(4-Chloro-phenyl)-[1,2,4]thiadiazol-5-yl]-4-[2-(3-methoxy-phenyl)-ethyl]-piperazine |
| 15 | 1-[2-(3-Methoxy-phenyl)-ethyl]-4-[3-(3-methoxy-phenyl)-[1,2,4]thiadiazol-5-yl]-piperazine |
| 16 | 1-[2-(3-Methoxy-phenyl)-ethyl]-4-(3-p-tolyl-[1,2,4]thiadiazol-5-yl)-piperazine |
| 17 | 1-[3-(4-Chloro-phenyl)-[1,2,4]thiadiazol-5-yl]-4-[2-(4-methoxy-phenyl)-ethyl]-piperazine |
| 18 | 1-[2-(4-Methoxy-phenyl)-ethyl]-4-[3-(3-methoxy-phenyl)-[1,2,4]thiadiazol-5-yl]-piperazine |
| 19 | 1-[2-(4-Methoxy-phenyl)-ethyl]-4-(3-p-tolyl-[1,2,4]thiadiazol-5-yl)-piperazine |
| 20 | 1-[2-(3-Methoxy-phenyl)-ethyl]-4-(3-pyridin-4-yl-[1,2,4]thiadiazol-5-yl)-piperazine |
| 21 | 1-[3-(4-Chloro-phenyl)-[1,2,4]thiadiazol-5-yl]-4-[2-(3-fluoro-phenyl)-ethyl]-piperazine |
| 22 | 1-[2-(3-Chloro-phenyl)-ethyl]-4-[3-(4-chloro-phenyl)-[1,2,4]thiadiazol-5-yl]-piperazine |
| 23 | 1-[3-(4-Chloro-phenyl)-[1,2,4]thiadiazol-5-yl]-4-(2-m-tolyl-ethyl)-piperazine |
| 24 | 1-[3-(4-Chloro-phenyl)-[1,2,4]thiadiazol-5-yl]-4-[2-(4-fluoro-phenyl)-ethyl]-piperazine |
| 25 | 1-[2-(4-Chloro-phenyl)-ethyl]-4-[3-(4-chloro-phenyl)-[1,2,4]thiadiazol-5-yl]-piperazine |
| 26 | 1-[3-(4-Chloro-phenyl)-[1,2,4]thiadiazol-5-yl]-4-(2-p-tolyl-ethyl)-piperazine |
| 27 | 1-[3-(4-Chloro-phenyl)-[1,2,4]thiadiazol-5-yl]-4-[2-(2-methoxy-phenyl)-ethyl]-piperazine |
| 28 | 1-[3-(4-Chloro-phenyl)-[1,2,4]thiadiazol-5-yl]-4-[2-(2-fluoro-phenyl)-ethyl]-piperazine |
| 29 | 1-[2-(2-Chloro-phenyl)-ethyl]-4-[3-(4-chloro-phenyl)-[1,2,4]thiadiazol-5-yl]-piperazine |
| 30 | 1-[2-(3-Methoxy-phenyl)-ethyl]-4-[3-(6-trifluoromethyl-pyridin-3-yl)-[1,2,4]thiadiazol-5-yl]-piperazine |
| 31 | 1-[3-(3,5-Dichloro-phenyl)-[1,2,4]thiadiazol-5-yl]-4-[2-(3-methoxy-phenyl)-ethyl]-piperazine |
| 32 | 1-[3-(4-Chloro-phenyl)-[1,2,4]thiadiazol-5-yl]-4-[3-(3-methoxy-phenyl)-propyl]-piperazine |
| 33 | 1-[2-(3-Methoxy-phenyl)-ethyl]-4-(3-thiophen-2-yl-[1,2,4]thiadiazol-5-yl)-piperazine |
| 34 | 1-[3-(4-Fluoro-phenyl)-[1,2,4]thiadiazol-5-yl]-4-[2-(3-methoxy-phenyl)-ethyl]-piperazine |
| 35 | 1-[2-(3-Methoxy-phenyl)-ethyl]-4-[3-(2-methoxy-phenyl)-[1,2,4]thiadiazol-5-yl]-piperazine |
| 36 | 1-[2-(3-Methoxy-phenyl)-ethyl]-4-[3-(4-trifluoromethoxy-phenyl)-[1,2,4]thiadiazol-5-yl]-piperazine |
| 37 | 1-[2-(4-Methoxy-phenyl)-ethyl]-4-[3-(4-trifluoromethoxy-phenyl)-[1,2,4]thiadiazol-5-yl]-piperazine |
| 38 | 1-[3-(4-Chloro-phenyl)-[1,2,4]thiadiazol-5-yl]-4-[2-(3-trifluoromethoxy-phenyl)-ethyl]-piperazine |
| 39 | 1-[3-(4-Chloro-phenyl)-[1,2,4]thiadiazol-5-yl]-4-[3-(2-methoxy-phenyl)-propyl]-piperazine |
| 40 | 1-[2-(4-Methoxy-phenyl)-ethyl]-4-[3-(4-methoxy-phenyl)-[1,2,4]thiadiazol-5-yl]-piperazine |
| 41 | 1-[3-(3-Chloro-phenyl)-[1,2,4]thiadiazol-5-yl]-4-[2-(4-methoxy-phenyl)-ethyl]-piperazine |
| 42 | 1-[2-(4-Methoxy-phenyl)-ethyl]-4-[3-(6-trifluoromethyl-pyridin-3-yl)-[1,2,4]thiadiazol-5-yl]-piperazine |
| 43 | 1-[2-(4-Methoxy-phenyl)-ethyl]-4-(3-pyridin-4-yl-[1,2,4]thiadiazol-5-yl)-piperazine |
| 44 | 1-[2-(4-Methoxy-phenyl)-ethyl]-4-(3-thiophen-2-yl-[1,2,4]thiadiazol-5-yl)-piperazine |
| 45 | 1-[2-(4-Methoxy-phenyl)-ethyl]-4-[3-(2-methoxy-phenyl)-[1,2,4]thiadiazol-5-yl]-piperazine |
| 46 | 1-[3-(3,5-Dichloro-phenyl)-[1,2,4]thiadiazol-5-yl]-4-[2-(4-methoxy-phenyl)-ethyl]-piperazine |

TABLE 2-continued

| Example | Chemical name |
|---|---|
| 47 | 1-[3-(4-Fluoro-phenyl)-[1,2,4]thiadiazol-5-yl]-4-[2-(4-methoxy-phenyl)-ethyl]-piperazine |
| 48 | 1-[3-(3-Chloro-phenyl)-[1,2,4]thiadiazol-5-yl]-4-[2-(3-methoxy-phenyl)-ethyl]-piperazine |
| 49 | 1-[2-(3-Methoxy-phenyl)-ethyl]-4-[3-(4-methoxy-phenyl)-[1,2,4]thiadiazol-5-yl]-piperazine |
| 50 | 1-[3-(4-Chloro-phenyl)-[1,2,4]thiadiazol-5-yl]-4-[2-(4-ethoxy-phenyl)-ethyl]-piperazine |
| 51 | 1-[3-(4-Chloro-phenyl)-[1,2,4]thiadiazol-5-yl]-4-[2-(3-isopropoxy-phenyl)-ethyl]-piperazine |
| 52 | 1-[3-(4-Chloro-phenyl)-[1,2,4]thiadiazol-5-yl]-4-[3-(4-methoxy-phenyl)-propyl]-piperazine |
| 53 | 2-{4-[3-(4-Chloro-phenyl)-[1,2,4]thiadiazol-5-yl]-piperazin-1-yl}-1-(4-methoxy-phenyl)-ethanone |
| 54 | 2-{4-[3-(4-Chloro-phenyl)-[1,2,4]thiadiazol-5-yl]-piperazin-1-yl}-1-(4-methoxy-phenyl)-ethanol |
| 55 | 1-[3-(4-Chloro-2-fluoro-phenyl)-[1,2,4]thiadiazol-5-yl]-4-[2-(3-methoxy-phenyl)-ethyl]-piperazine |
| 56 | 1-[3-(4-Chloro-2-fluoro-phenyl)-[1,2,4]thiadiazol-5-yl]-4-[2-(4-methoxy-phenyl)-ethyl]-piperazine |
| 57 | 1-[3-(2-Chloro-phenyl)-[1,2,4]thiadiazol-5-yl]-4-[2-(3-methoxy-phenyl)-ethyl]-piperazine |
| 58 | 1-[3-(2-Chloro-phenyl)-[1,2,4]thiadiazol-5-yl]-4-[2-(4-methoxy-phenyl)-ethyl]-piperazine |
| 59 | 1-[3-(4-Chloro-phenyl)-[1,2,4]thiadiazol-5-yl]-4-[2-(4-methoxy-phenyl)-allyl]-piperazine |
| 60 | 2-{4-[3-(4-Chloro-phenyl)-[1,2,4]thiadiazol-5-yl]-piperazin-1-yl}-1-(3-methoxy-phenyl)-ethanone |
| 61 | 2-{4-[3-(4-Chloro-phenyl)-[1,2,4]thiadiazol-5-yl]-piperazin-1-yl}-1-(3-methoxy-phenyl)-ethanol |
| 62 | 2-{4-[3-(4-Chloro-phenyl)-[1,2,4]thiadiazol-5-yl]-piperazin-1-yl}-1-(3-fluoro-phenyl)-ethanone |
| 63 | 2-{4-[3-(4-Chloro-phenyl)-[1,2,4]thiadiazol-5-yl]-piperazin-1-yl}-1-(3-fluoro-phenyl)-ethanol |
| 64 | 1-[3-(4-Chloro-phenyl)-[1,2,4]thiadiazol-5-yl]-4-[2-fluoro-2-(4-methoxy-phenyl)-ethyl]-piperazine |
| 65 | 1-[3-(4-Chloro-phenyl)-[1,2,4]thiadiazol-5-yl]-4-[2-fluoro-2-(3-methoxy-phenyl)-ethyl]-piperazine |
| 66 | 1-[3-(4-Fluoro-2-methoxy-phenyl)-[1,2,4]thiadiazol-5-yl]-4-[2-(3-methoxy-phenyl)-ethyl]-piperazine |
| 67 | 1-[3-(4-Fluoro-2-methoxy-phenyl)-[1,2,4]thiadiazol-5-yl]-4-[2-(4-methoxy-phenyl)-ethyl]-piperazine |
| 68 | 1-[1-(4-Chloro-phenyl)-cyclopropylmethyl]-4-[3-(4-chloro-phenyl)-[1,2,4]thiadiazol-5-yl]-piperazine |
| 69 | 1-[3-(4-Chloro-phenyl)-[1,2,4]thiadiazol-5-yl]-4-[2-(3-difluoromethoxy-phenyl)-ethyl]-piperazine |
| 70 | 1-[3-(4-Chloro-phenyl)-[1,2,4]thiadiazol-5-yl]-4-[2-(4-difluoromethoxy-phenyl)-ethyl]-piperazine |
| 71 | 1-[3-(4-Chloro-phenyl)-[1,2,4]thiadiazol-5-yl]-4-[2-(4-isopropoxy-phenyl)-ethyl]-piperazine |
| 72 | 1-[3-(4-Chloro-phenyl)-[1,2,4]thiadiazol-5-yl]-4-[2-(4-methoxy-phenyl)-propyl]-piperazine |
| 73 | 1-[3-(4-Chloro-phenyl)-[1,2,4]thiadiazol-5-yl]-4-[2-(4-methoxy-phenyl)-1-methyl-ethyl]-piperazine |
| 75 | 1-[3-(4-Chloro-phenyl)-[1,2,4]thiadiazol-5-yl]-4-[2-(2-methoxy-pyridin-4-yl)-ethyl]-piperazine |
| 76 | 2-(5-{4-[2-(4-Methoxy-phenyl)-ethyl]-piperazin-1-yl}-[1,2,4]thiadiazol-3-yl)-pyrazine |
| 77 | 2-(5-{4-[2-(3-Methoxy-phenyl)-ethyl]-piperazin-1-yl}-[1,2,4]thiadiazol-3-yl)-pyrazine |
| 78 | 4-(5-{4-[2-(4-Methoxy-phenyl)-ethyl]-piperazin-1-yl}-[1,2,4]thiadiazol-3-yl)-benzonitrile |
| 79 | 1-[3-(4-Chloro-phenyl)-[1,2,4]thiadiazol-5-yl]-4-[2-(6-methoxy-pyridin-3-yl)-ethyl]-piperazine |
| 80 | 1-[3-(4-Chloro-phenyl)-[1,2,4]thiadiazol-5-yl]-4-[2-(3-fluoro-4-methoxy-phenyl)-ethyl]-piperazine |
| 81 | 3-(5-{4-[2-(4-Methoxy-phenyl)-ethyl]-piperazin-1-yl}-[1,2,4]thiadiazol-3-yl)-benzonitrile |
| 82 | 1-[3-(3-Chloro-phenyl)-[1,2,4]thiadiazol-5-yl]-4-phenethyl-piperazine |
| 83 | 1-[3-(3-Fluoro-phenyl)-[1,2,4]thiadiazol-5-yl]-4-phenethyl-piperazine |
| 84 | 1-[3-(3-Fluoro-phenyl)-[1,2,4]thiadiazol-5-yl]-4-[2-(4-methoxy-phenyl)-ethyl]-piperazine |
| 85 | 1-[3-(3-Chloro-phenyl)-[1,2,4]thiadiazol-5-yl]-4-[2-(4-fluoro-phenyl)-ethyl]-piperazine |
| 86 | 1-[2-(4-Fluoro-phenyl)-ethyl]-4-[3-(3-fluoro-phenyl)-[1,2,4]thiadiazol-5-yl]-piperazine |
| 87 | 1-[2-(4-Chloro-phenyl)-ethyl]-4-[3-(3-chloro-phenyl)-[1,2,4]thiadiazol-5-yl]-piperazine |

TABLE 2-continued

| Example | Chemical name |
|---|---|
| 88 | 1-[2-(4-Chloro-phenyl)-ethyl]-4-[3-(3-fluoro-phenyl)-[1,2,4]thiadiazol-5-yl]-piperazine |
| 89 | 1-[3-(3-Chloro-phenyl)-[1,2,4]thiadiazol-5-yl]-4-[2-(2-methoxy-pyridin-4-yl)-ethyl]-piperazine |
| 90 | 1-[3-(3-Fluoro-phenyl)-[1,2,4]thiadiazol-5-yl]-4-[2-(2-methoxy-pyridin-4-yl)-ethyl]-piperazine |
| 91 | 1-[3-(5-Chloro-pyridin-3-yl)-[1,2,4]thiadiazol-5-yl]-4-[2-(4-methoxy-phenyl)-ethyl]-piperazine |
| 92 | 1-[3-(3-Chloro-phenyl)-[1,2,4]thiadiazol-5-yl]-4-(2-methyl-benzyl)-piperazine |
| 93 | 1-[3-(3-Chloro-phenyl)-[1,2,4]thiadiazol-5-yl]-4-[2-(6-methoxy-pyridin-3-yl)-ethyl]-piperazine |
| 94 | 1-[3-(6-Methyl-pyridin-3-yl)-[1,2,4]thiadiazol-5-yl]-4-phenethyl-piperazine |
| 95 | 1-[2-(4-Methoxy-phenyl)-ethyl]-4-[3-(6-methyl-pyridin-3-yl)-[1,2,4]thiadiazol-5-yl]-piperazine |
| 96 | 1-[2-(4-Fluoro-phenyl)-ethyl]-4-[3-(6-methyl-pyridin-3-yl)-[1,2,4]thiadiazol-5-yl]-piperazine |
| 97 | 1-[2-(2-Methoxy-pyridin-4-yl)-ethyl]-4-[3-(6-methyl-pyridin-3-yl)-[1,2,4]thiadiazol-5-yl]-piperazine |
| 98 | 1-[2-(4-Chloro-phenyl)-ethyl]-4-[3-(6-methyl-pyridin-3-yl)-[1,2,4]thiadiazol-5-yl]-piperazine |
| 99 | 1-[3-(3-Fluoro-phenyl)-[1,2,4]thiadiazol-5-yl]-4-(2-methyl-benzyl)-piperazine |
| 100 | 1-[3-(3-Fluoro-phenyl)-[1,2,4]thiadiazol-5-yl]-4-[2-(6-methoxy-pyridin-3-yl)-ethyl]-piperazine |
| 101 | 1-[3-(3,4-Difluoro-phenyl)-[1,2,4]thiadiazol-5-yl]-4-phenethyl-piperazine |
| 102 | 1-[3-(3,4-Difluoro-phenyl)-[1,2,4]thiadiazol-5-yl]-4-[2-(4-methoxy-phenyl)-ethyl]-piperazine |
| 103 | 1-[3-(3,4-Difluoro-phenyl)-[1,2,4]thiadiazol-5-yl]-4-[2-(4-fluoro-phenyl)-ethyl]-piperazine |
| 104 | 1-[2-(4-Chloro-phenyl)-ethyl]-4-[3-(3,4-difluoro-phenyl)-[1,2,4]thiadiazol-5-yl]-piperazine |
| 105 | 1-[3-(3,4-Difluoro-phenyl)-[1,2,4]thiadiazol-5-yl]-4-[2-(6-methoxy-pyridin-3-yl)-ethyl]-piperazine |
| 106 | 1-[3-(3,4-Difluoro-phenyl)-[1,2,4]thiadiazol-5-yl]-4-[2-(2-methoxy-pyridin-4-yl)-ethyl]-piperazine |
| 107 | 1-[3-(3,4-Difluoro-phenyl)-[1,2,4]thiadiazol-5-yl]-4-(2-methyl-benzyl)-piperazine |
| 108 | 4-[5-(4-Phenethyl-piperazin-1-yl)-[1,2,4]thiadiazol-3-yl]-benzonitrile |
| 109 | 3-[5-(4-Phenethyl-piperazin-1-yl)-[1,2,4]thiadiazol-3-yl]-benzonitrile |
| 110 | 4-(5-{4-[2-(4-Fluoro-phenyl)-ethyl]-piperazin-1-yl}-[1,2,4]thiadiazol-3-yl)-benzonitrile |
| 111 | 3-(5-{4-[2-(4-Fluoro-phenyl)-ethyl]-piperazin-1-yl}-[1,2,4]thiadiazol-3-yl)-benzonitrile |
| 112 | 4-(5-{4-[2-(4-Chloro-phenyl)-ethyl]-piperazin-1-yl}-[1,2,4]thiadiazol-3-yl)-benzonitrile |
| 113 | 3-(5-{4-[2-(4-Chloro-phenyl)-ethyl]-piperazin-1-yl}-[1,2,4]thiadiazol-3-yl)-benzonitrile |
| 114 | 4-(5-{4-[2-(6-Methoxy-pyridin-3-yl)-ethyl]-piperazin-1-yl}-[1,2,4]thiadiazol-3-yl)-benzonitrile |
| 115 | 3-(5-{4-[2-(6-Methoxy-pyridin-3-yl)-ethyl]-piperazin-1-yl}-[1,2,4]thiadiazol-3-yl)-benzonitrile |
| 116 | 4-(5-{4-[2-(2-Methoxy-pyridin-4-yl)-ethyl]-piperazin-1-yl}-[1,2,4]thiadiazol-3-yl)-benzonitrile |
| 117 | 3-(5-{4-[2-(2-Methoxy-pyridin-4-yl)-ethyl]-piperazin-1-yl}-[1,2,4]thiadiazol-3-yl)-benzonitrile |
| 118 | 4-{5-[4-(2-Methyl-benzyl)-piperazin-1-yl]-[1,2,4]thiadiazol-3-yl}-benzonitrile |
| 119 | 3-{5-[4-(2-Methyl-benzyl)-piperazin-1-yl]-[1,2,4]thiadiazol-3-yl}-benzonitrile |
| 120 | 1-[3-(4-Chloro-pyridin-2-yl)-[1,2,4]thiadiazol-5-yl]-4-phenethyl-piperazine |
| 121 | 1-[3-(5-Chloro-pyridin-2-yl)-[1,2,4]thiadiazol-5-yl]-4-phenethyl-piperazine |
| 122 | 1-[3-(4-Chloro-pyridin-2-yl)-[1,2,4]thiadiazol-5-yl]-4-[2-(4-fluoro-phenyl)-ethyl]-piperazine |
| 123 | 1-[2-(4-Chloro-phenyl)-ethyl]-4-[3-(4-chloro-pyridin-2-yl)-[1,2,4]thiadiazol-5-yl]-piperazine |
| 124 | 1-[2-(4-Chloro-phenyl)-ethyl]-4-[3-(5-chloro-pyridin-2-yl)-[1,2,4]thiadiazol-5-yl]-piperazine |
| 125 | 1-[3-(4-Chloro-pyridin-2-yl)-[1,2,4]thiadiazol-5-yl]-4-[2-(4-methoxy-phenyl)-ethyl]-piperazine |
| 126 | 1-[3-(5-Chloro-pyridin-2-yl)-[1,2,4]thiadiazol-5-yl]-4-[2-(4-methoxy-phenyl)-ethyl]-piperazine |
| 127 | 1-[3-(4-Chloro-pyridin-2-yl)-[1,2,4]thiadiazol-5-yl]-4-[2-(2-methoxy-pyridin-4-yl)-ethyl]-piperazine |

TABLE 2-continued

| Example | Chemical name |
|---|---|
| 128 | 1-[3-(4-Chloro-pyridin-2-yl)-[1,2,4]thiadiazol-5-yl]-4-(2-methyl-benzyl)-piperazine |
| 129 | 1-[3-(5-Chloro-pyridin-2-yl)-[1,2,4]thiadiazol-5-yl]-4-(2-methyl-benzyl)-piperazine |
| 130 | 1-[3-(5-Chloro-pyridin-3-yl)-[1,2,4]thiadiazol-5-yl]-4-phenethyl-piperazine |
| 131 | 1-[3-(5-Chloro-pyridin-3-yl)-[1,2,4]thiadiazol-5-yl]-4-[2-(4-fluoro-phenyl)-ethyl]-piperazine |
| 132 | 1-[2-(4-Chloro-phenyl)-ethyl]-4-[3-(5-chloro-pyridin-3-yl)-[1,2,4]thiadiazol-5-yl]-piperazine |
| 133 | 1-[3-(5-Chloro-pyridin-3-yl)-[1,2,4]thiadiazol-5-yl]-4-[2-(2-methoxy-pyridin-4-yl)-ethyl]-piperazine |
| 134 | 1-[3-(4-Chloro-phenyl)-[1,2,4]thiadiazol-5-yl]-4-[2-(3,4-difluoro-phenyl)-ethyl]-piperazine |
| 135 | 1-[3-(3-Chloro-phenyl)-[1,2,4]thiadiazol-5-yl]-4-[2-(3,4-difluoro-phenyl)-ethyl]-piperazine |
| 136 | 1-[2-(3,4-Difluoro-phenyl)-ethyl]-4-[3-(3,4-difluoro-phenyl)-[1,2,4]thiadiazol-5-yl]-piperazine |
| 137 | 3-(5-(4-[2-(3,4-Difluoro-phenyl)-ethyl]-piperazin-1-yl}-[1,2,4]thiadiazol-3-yl)-benzonitrile |
| 138 | 4-(5-(4-[2-(3,4-Difluoro-phenyl)-ethyl]-piperazin-1-yl}-[1,2,4]thiadiazol-3-yl)-benzonitrile |
| 139 | 1-[3-(5-Chloro-pyridin-2-yl)-[1,2,4]thiadiazol-5-yl]-4-[2-(3,4-difluoro-phenyl)-ethyl]-piperazine |
| 140 | 1-[3-(4-Chloro-phenyl)-[1,2,4]thiadiazol-5-yl]-4-[2-(3-trifluoromethyl-phenyl)-ethyl]-piperazine |
| 141 | 1-[3-(3-Fluoro-phenyl)-[1,2,4]thiadiazol-5-yl]-4-[2-(3-trifluoromethyl-phenyl)-ethyl]-piperazine |
| 142 | 1-[3-(3-Chloro-phenyl)-[1,2,4]thiadiazol-5-yl]-4-[2-(3-trifluoromethyl-phenyl)-ethyl]-piperazine |
| 143 | 4-(5-{4-[2-(3-Trifluoromethyl-phenyl)-ethyl]-piperazin-1-yl}-[1,2,4]thiadiazol-3-yl)-benzonitrile |
| 144 | 1-[3-(4-Chloro-phenyl)-[1,2,4]thiadiazol-5-yl]-4-[2-(4-trifluoromethyl-phenyl)-ethyl]-piperazine |
| 145 | 1-[3-(3-Chloro-phenyl)-[1,2,4]thiadiazol-5-yl]-4-[2-(4-trifluoromethyl-phenyl)-ethyl]-piperazine |
| 146 | 1-[3-(3,4-Difluoro-phenyl)-[1,2,4]thiadiazol-5-yl]-4-[2-(4-trifluoromethyl-phenyl)-ethyl]-piperazine |
| 147 | 4-(5-(4-[2-(4-Trifluoromethyl-phenyl)-ethyl]-piperazin-1-yl}-[1,2,4]thiadiazol-3-yl)-benzonitrile |
| 148 | 1-[2-(3,4-Difluoro-phenyl)-ethyl]-4-[3-(6-methyl-pyridin-3-yl)-[1,2,4]thiadiazol-5-yl]-piperazine |
| 149 | 1-[3-(5-Chloro-pyridin-3-yl)-[1,2,4]thiadiazol-5-yl]-4-[2-(3-trifluoromethyl-phenyl)-ethyl]-piperazine |
| 150 | 1-(2-Methyl-benzyl)-4-[3-(6-methyl-pyridin-3-yl)-[1,2,4]thiadiazol-5-yl]-piperazine |
| 151 | 1-[3-(5-Chloro-pyridin-3-yl)-[1,2,4]thiadiazol-5-yl]-4-(2-methyl-benzyl)-piperazine |
| 152 | 1-[3-(5-Chloro-pyridin-3-yl)-[1,2,4]thiadiazol-5-yl]-4-[2-(4-trifluoromethyl-phenyl)-ethyl]-piperazine |
| 153 | 1-(2-Cyclohexyl-ethyl)-4-[3-(3,4-difluoro-phenyl)-[1,2,4]thiadiazol-5-yl]-piperazine |
| 154 | 1-(2-Cyclohexyl-ethyl)-4-[3-(3-fluoro-phenyl)-[1,2,4]thiadiazol-5-yl]-piperazine |
| 155 | 5-(4-(3-phenylpropyl)piperazin-1-yl)-3-(p-tolyl)-1,2,4-thiadiazole |
| 156 | 5-(4-(3,4-difluorophenethyl)piperazin-1-yl)-3-(3-fluorophenyl)-1,2,4-thiadiazole |
| 157 | 3-(4-chloropyridin-2-yl)-5-(4-(3,4-difluorophenethyl)piperazin-1-yl)-1,2,4-thiadiazole |
| 158 | 3-(3,4-difluorophenyl)-5-(4-(3-(trifluoromethyl)phenethyl)piperazin-1-yl)-1,2,4-thiadiazole |
| 159 | 3-(4-chloropyridin-2-yl)-5-(4-(3-(trifluoromethyl)phenethyl)piperazin-1-yl)-1,2,4-thiadiazole |
| 160 | 3-(5-chloropyridin-3-yl)-5-(4-(3,4-difluorophenethyl)piperazin-1-yl)-1,2,4-thiadiazole |
| 161 | 3-(4-chlorophenyl)-5-(4-(2-cyclohexylethyl)piperazin-1-yl)-1,2,4-thiadiazole |
| 162 | 3-(3-chlorophenyl)-5-(4-(2-cyclohexylethyl)piperazin-1-yl)-1,2,4-thiadiazole |
| 163 | 3-(5-chloropyridin-3-yl)-5-(4-(2-(piperidin-1-yl)ethyl)piperazin-1-yl)-1,2,4-thiadiazole |
| 164 | 3-(3,4-difluorophenyl)-5-(4-(2-(tetrahydro-2H-pyran-4-yl)ethyl)piperazin-1-yl)-1,2,4-thiadiazole |
| 165 | 3-(3-chlorophenyl)-5-(4-(2-(tetrahydro-2H-pyran-4-yl)ethyl)piperazin-1-yl)-1,2,4-thiadiazole |
| 166 | 3-(5-chloropyridin-3-yl)-5-(4-(2-(tetrahydro-2H-pyran-4-yl)ethyl)piperazin-1-yl)-1,2,4-thiadiazole |

TABLE 2-continued

| Example | Chemical name |
|---|---|
| 167 | 3-(4-chlorophenyl)-5-(4-(2-(tetrahydro-2H-pyran-4-yl)ethyl)piperazin-1-yl)-1,2,4-thiadiazole |
| 168 | 3-(2-chloropyridin-4-yl)-5-(4-(2-(2-methoxypyridin-4-yl)ethyl)piperazin-1-yl)-1,2,4-thiadiazole |
| 169 | 5-(4-(4-chlorophenethyl)piperazin-1-yl)-3-(2-chloropyridin-4-yl)-1,2,4-thiadiazole |
| 170 | 3-(2-chloropyridin-4-yl)-5-(4-phenethylpiperazin-1-yl)-1,2,4-thiadiazole |
| 171 | 3-(2-methylpyridin-4-yl)-5-(4-phenethylpiperazin-1-yl)-1,2,4-thiadiazole |
| 172 | 5-(4-(2-(2-methoxypyridin-4-yl)ethyl)piperazin-1-yl)-3-(2-methylpyridin-4-yl)-1,2,4-thiadiazole |
| 173 | 3-(6-methylpyridazin-4-yl)-5-(4-phenethylpiperazin-1-yl)-1,2,4-thiadiazole |
| 174 | 5-(4-(4-fluorophenethyl)piperazin-1-yl)-3-(6-methylpyridazin-4-yl)-1,2,4-thiadiazole |
| 175 | 5-(4-(3,4-difluorophenethyl)piperazin-1-yl)-3-(6-methylpyridazin-4-yl)-1,2,4-thiadiazole |
| 176 | 5-(4-(2-(2-methoxypyridin-4-yl)ethyl)piperazin-1-yl)-3-(6-methylpyridazin-4-yl)-1,2,4-thiadiazole |
| 177 | 5-(4-(4-methoxyphenethyl)piperazin-1-yl)-3-(6-methylpyridazin-4-yl)-1,2,4-thiadiazole |
| 178 | 3-(2-methylpyrimidin-5-yl)-5-(4-phenethylpiperazin-1-yl)-1,2,4-thiadiazole |
| 179 | 5-(4-(4-methoxyphenethyl)piperazin-1-yl)-3-(2-methylpyrimidin-5-yl)-1,2,4-thiadiazole |
| 180 | 5-(4-(4-chlorophenethyl)piperazin-1-yl)-3-(2-methylpyrimidin-5-yl)-1,2,4-thiadiazole |
| 181 | 5-(4-(4-fluorophenethyl)piperazin-1-yl)-3-(2-methylpyrimidin-5-yl)-1,2,4-thiadiazole |
| 182 | 5-(4-(3,4-difluorophenethyl)piperazin-1-yl)-3-(2-methylpyrimidin-5-yl)-1,2,4-thiadiazole |
| 183 | 5-(4-(2-(2-methoxypyridin-4-yl)ethyl)piperazin-1-yl)-3-(2-methylpyrimidin-5-yl)-1,2,4-thiadiazole |

EXPERIMENTAL PART

Example 2

1-Benzo[1,3]dioxol-5-ylmethyl-4-(3-p-tolyl-[1,2,4]thiadiazol-5-yl)-piperazine

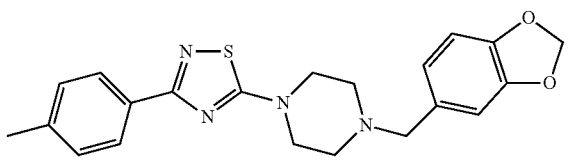 [SMILES: Cc1ccc(-c2nsc(N3CCN(Cc4ccc5c(c4)OCO5)CC3)n2)cc1]

a) 5-Chloro-3-p-tolyl-1,2,4-thiadiazole

A mixture of 4-methylbenzimidamide hydrochloride (1.55 g, 9.08 mmol) and Et$_3$N (4.6 g, 6.33 ml, 45.4 mmol) in DCM (30 mL) was cooled with a NaCl/ice-bath to −10° C. Perchloromethyl mercaptan (1.86 g, 1.09 ml, 9.99 mmol) in DCM (10 mL) was added during 40 min. The resulting yellow suspension was stirred for 20 min at 0° C. and 2 h at RT. Water (40 mL) and aq. 2N NaOH (10 mL) was added. The organic layer was separated and extracted with brine (50 mL). The aqueous layers were extracted with DCM (2×40 mL). The combined organic layers were dried over Na$_2$SO$_4$, filtered off and concentrated in vacuo. The residue was purified by silica chromatography (Flash 50 g Si-cartridge using AcOEt: Heptane 1:19 to 1:9.) to yield 5-chloro-3-p-tolyl-1,2,4-thiadiazole (1.63 g, 7.74 mmol, 85% yield) as light yellow solid.

b) 1-(benzo[d][1,3]dioxol-5-ylmethyl)piperazine

In a 5 mL microwave vial, 5-chloro-3-p-tolyl-1,2,4-thiadiazole (75.0 μmol), 1-(benzo[d][1,3]dioxol-5-ylmethyl)piperazine (300 μmol) and DIPEA (750 μmol) in 0.6 mL N-Methyl-2-pyrrolidinone was heated in the microwave at 165° C. for 12 min. The resulting reaction mixture solution was purified by preparative HPLC on reversed phase eluting with a gradient formed from MeCN, water and NEt$_3$ to yield after evaporation of the product containing fractions of the title compound as light brown solid. MS (m/e): 395.2 (MH$^+$).

Example 3

1-(2,4-Dichloro-benzyl)-4-(3-p-tolyl-[1,2,4]thiadiazol-5-yl)-piperazine

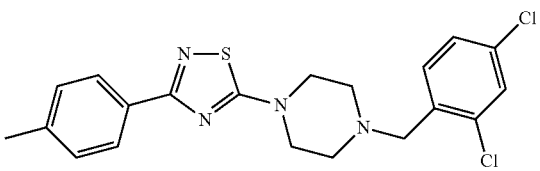 [SMILES: Cc1ccc(-c2nsc(N3CCN(Cc4ccc(Cl)cc4Cl)CC3)n2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-p-tolyl-1,2,4-thiadiazole and 1-(2,4-dichlorobenzyl)piperazine as light brown solid. MS (m/e): 419.2 (MH⁺).

Example 4

1-Phenethyl-4-(3-p-tolyl-[1,2,4]thiadiazol-5-yl)-piperazine

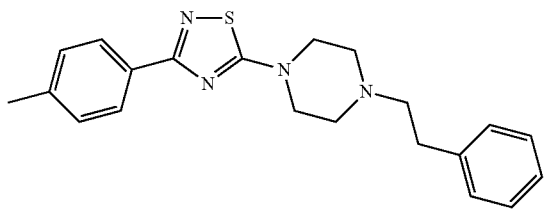 [SMILES: Cc1ccc(-c2nsc(N3CCN(CCc4ccccc4)CC3)n2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-p-tolyl-1,2,4-thiadiazole and 1-phenethylpiperazine as light brown solid. MS (m/e): 365.3 (MH⁺).

Example 5

1-[2-(3,4-Dichloro-phenyl)-ethyl]-4-(3-p-tolyl-[1,2,4]thiadiazol-5-yl)-piperazine

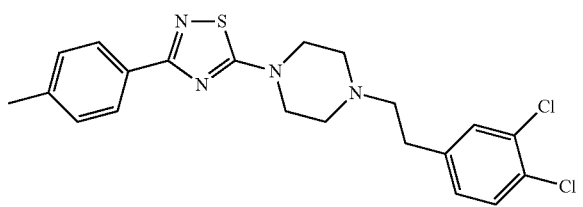 [SMILES: Cc1ccc(-c2nsc(N3CCN(CCc4ccc(Cl)c(Cl)c4)CC3)n2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-p-tolyl-1,2,4-thiadiazole and 1-(3,4-dichlorophenethyl)piperazine as brown solid. MS (m/e): 433.3 (MH⁺).

Example 6

1-(2-Methyl-benzyl)-4-(3-p-tolyl-[1,2,4]thiadiazol-5-yl)-piperazine

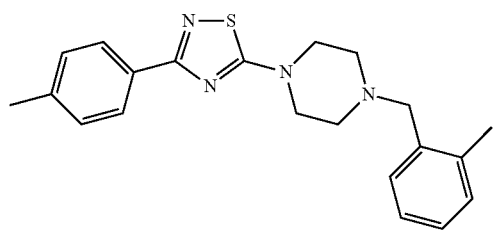

a) 1-(3-p-Tolyl-[1,2,4]thiadiazol-5-yl)-piperazine

A mixture of 5-chloro-3-p-tolyl-1,2,4-thiadiazole (900 mg, 4.27 mmol) and piperazine (1.84 g, 21.4 mmol) in 25 mL EtOH were heated to reflux and stirred for 1 h at this temperature. The resulting yellow solution was cooled to room temperature and concentrated in vacuo. The residue was purified by flash column chromatography on silica eluting with a gradient formed from DCM, MeOH and NEt₃ to yield after evaporation of the product containing fractions 1.1 g (99%) of the title compound as light yellow solid. MS (m/e): 261.3 (MH⁺).

b) 1-(2-Methyl-benzyl)-4-(3-p-tolyl-[1,2,4]thiadiazol-5-yl)-piperazine

A mixture of 5-(piperazin-1-yl)-3-p-tolyl-1,2,4-thiadiazole (17.3 mg, 66.4 μmol), 1-(chloromethyl)-2-methylbenzene (14.0 mg, 99.7 μmol) and DIPEA (42.9 mg, 58.0 μl) in 0.8 mL N-Methyl-2-pyrrolidinone was heated in the microwave oven 165° C. for 12.5 min. The resulting reaction mixture solution was purified by preparative HPLC on reversed phase eluting with a gradient formed from MeCN, water and NEt₃ to yield after evaporation of the product containing fractions 17.5 mg (72%) of the title compound as yellow viscous oil. MS (m/e): 365.3 (MH⁺).

Example 12

1-[3-(4-Chloro-phenyl)-[1,2,4]thiadiazol-5-yl]-4-(2-methyl-benzyl)-piperazine

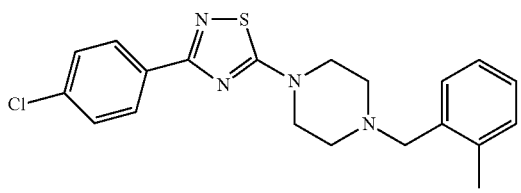 [SMILES: Cc1ccccc1CN1CCN(c2nc(-c3ccc(Cl)cc3)ns2)CC1]

a) 1-[3-(4-Chloro-phenyl)-[1,2,4]thiadiazol-5-yl]-piperazine

In analogy to the procedure described for the synthesis of 1-(3-p-Tolyl-[1,2,4]thiadiazol-5-yl)-piperazine (example 6, step a) the title compound was prepared from 5-chloro-3-(4-chlorophenyl)-1,2,4-thiadiazole and piperazine as light yellow solid. MS (m/e): 281.2 (MH⁺).

b) 1-[3-(4-Chloro-phenyl)-[1,2,4]thiadiazol-5-yl]-4-(2-methyl-benzyl)-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(chloromethyl)-2-methylbenzene as off-white foam. MS (m/e): 385.2 (MH⁺).

Example 13

1-[3-(3-Methoxy-phenyl)-[1,2,4]thiadiazol-5-yl]-4-(2-methyl-benzyl)-piperazine

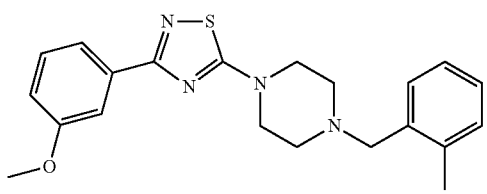 [SMILES: COc1cccc(-c2nsc(N3CCN(Cc4ccccc4C)CC3)n2)c1]

a) 1-[3-(3-Methoxy-phenyl)-[1,2,4]thiadiazol-5-yl]-piperazine

In analogy to the procedure described for the synthesis of 1-(3-p-Tolyl-[1,2,4]thiadiazol-5-yl)-piperazine (example 6, step a) the title compound was prepared from 5-chloro-3-(3-methoxyphenyl)-1,2,4-thiadiazole and piperazine as yellow solid. MS (m/e): 277.2 (MH$^+$).

b) 1-[3-(3-Methoxy-phenyl)-[1,2,4]thiadiazol-5-yl]-4-(2-methyl-benzyl)-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Methoxy-phenyl)-[1,2,4]thiadiazol-5-yl]-piperazine and 1-(chloromethyl)-2-methylbenzene as light yellow viscous oil. MS (m/e): 381.4 (MH$^+$).

Example 14

1-[3-(4-Chloro-phenyl)-[1,2,4]thiadiazol-5-yl]-4-[2-(3-methoxy-phenyl)-ethyl]-piperazine

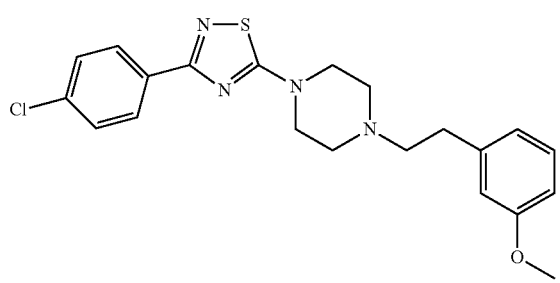 [SMILES: COc1cccc(CCN2CCN(c3nc(-c4ccc(Cl)cc4)ns3)CC2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-3-methoxybenzene as light yellow foam. MS (m/e): 415.2 (MH$^+$).

Example 15

1-[2-(3-Methoxy-phenyl)-ethyl]-4-[3-(3-methoxy-phenyl)-[1,2,4]thiadiazol-5-yl]-piperazine

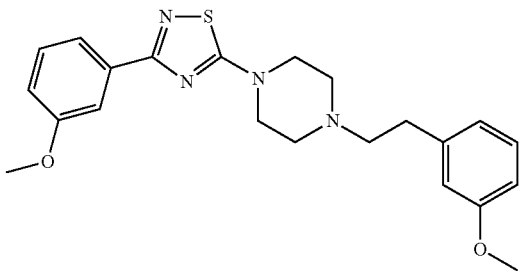

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Methoxy-phenyl)-[1,2,4]thiadiazol-5-yl]-piperazine and 1-(2-bromo ethyl)-3-methoxybenzene as light brown viscous oil. MS (m/e): 411.3 (MH$^+$).

Example 16

1-[2-(3-Methoxy-phenyl)-ethyl]-4-(3-p-tolyl-[1,2,4]thiadiazol-5-yl)-piperazine

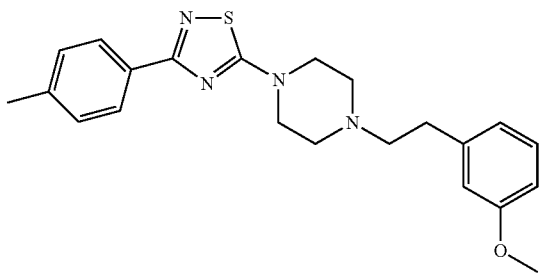

In analogy to the procedure described for the synthesis of 1-(2-Methyl-benzyl)-4-(3-p-tolyl-[1,2,4]thiadiazol-5-yl)-piperazine (example 6) the title compound was prepared from 5-(piperazin-1-yl)-3-(p-tolyl)-1,2,4-thiadiazole and 1-(2-bromoethyl)-3-methoxybenzene as light yellow foam. MS (m/e): 395.2 (MH$^+$).

Example 17

1-[3-(4-Chloro-phenyl)-[1,2,4]thiadiazol-5-yl]-4-[2-(4-methoxy-phenyl)-ethyl]-piperazine

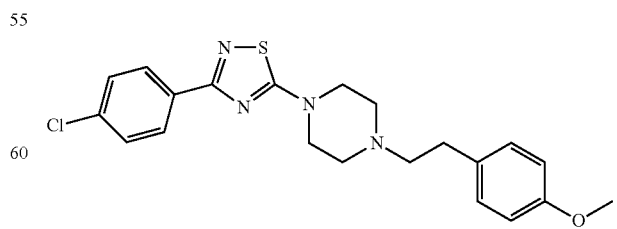

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-methoxybenzene as light yellow foam. MS (m/e): 415.2 (MH⁺).

Example 18

1-[2-(4-Methoxy-phenyl)-ethyl]-4-[3-(3-methoxy-phenyl)[1,2,4]thiadiazol-5-yl]-piperazine

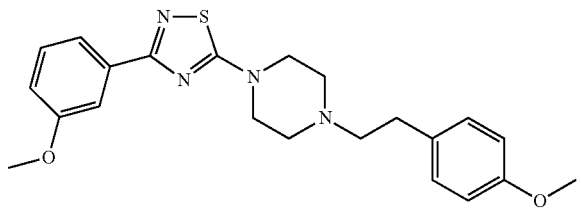

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Methoxy-phenyl)-[1,2,4]thiadiazol-5-yl]-piperazine and 1-(2-bromoethyl)-4-methoxybenzene as light yellow foam. MS (m/e): 411.3 (MH⁺).

Example 19

1-[2-(4-Methoxy-phenyl)-ethyl]-4-(3-p-tolyl-[1,2,4]thiadiazol-5-yl)-piperazine

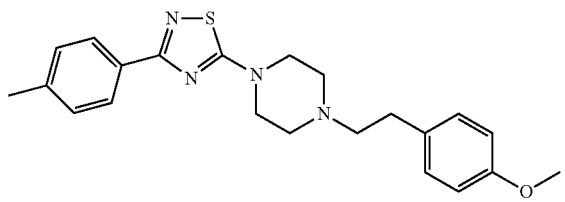

In analogy to the procedure described for the synthesis of 1-(2-Methyl-benzyl)-4-(3-p-tolyl-[1,2,4]thiadiazol-5-yl)-piperazine (example 6) the title compound was prepared from 5-(piperazin-1-yl)-3-(p-tolyl)-1,2,4-thiadiazole and 1-(2-bromoethyl)-4-methoxybenzene as off-white foam. MS (m/e): 395.2 (MH⁺).

Example 20

1-[2-(3-Methoxy-phenyl)-ethyl]-4-(3-pyridin-4-yl-[1,2,4]thiadiazol-5-yl)-piperazine

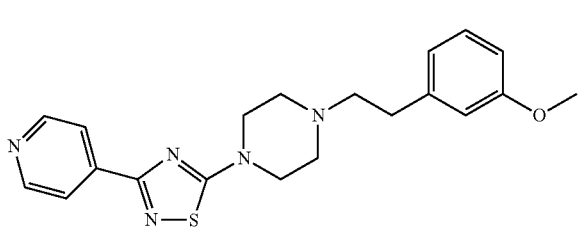 [SMILES: COc1cccc(CCN2CCN(c3nc(-c4ccncc4)ns3)CC2)c1]

a) 4-(5-Chloro-[1,2,4]thiadiazol-3-yl)-pyridine

A mixture of isonicotinimidamide hydrochloride (1.0 g, 6.35 mmol) and NEt₃ (3.21 g, 4.42 mL, 31.7 mmol) in 50 mL DCM was cooled to −5 and −10° C. Perchloromethyl mercaptan (1.3 g, 763 µl, 6.98 mmol) in 10 mL DCM was added drop wise over 1 h. The mixture was warmed to 0° C. over 30 min and stirred for 2 h. Water (50 mL) and 2M NaOH (10 mL) was added. The suspension was filtrated. The organic layer was extracted with DCM and washed with brine (50 mL) and the aqueous layer was extracted with DCM (50 mL). The organic layers were combined, dried over Na₂SO₄ and filtered off. The crude product was concentrated under vacuum and the residue dissolved in DCM, taken up on Isolute® and purified by column chromatography on silica eluting with a gradient formed from heptane and EtOAc to yield after evaporation of the product containing fraction 0.43 g (34%) of the title compound as a brown solid. MS (m/e): 198.1 (MH⁺).

b) 1-[2-(3-Methoxy-phenyl)-ethyl]-4-(3-pyridin-4-yl-[1,2,4]thiadiazol-5-yl)-piperazine A mixture of 5-chloro-3-(pyridin-4-yl)-1,2,4-thiadiazole (42 mg, 213 µmol), 1-(3-methoxyphenethyl)piperazine dihydrochloride (62.3 mg, 213 µmol) and DIPEA (137 mg, 186 µl, 1.06 mmol) in 10 mL EtOH was stirred for 2.5 h at RT the mixture was filtered, washed with EtOH and dried in vacuo at 50° C. for 2 hours to yield 12.6 mg (15%) of the title compounds as orange solid. MS (m/e): 382.2 (MH⁺).

Example 21

1-[3-(4-Chloro-phenyl)-[1,2,4]thiadiazol-5-yl]-4-[2-(3-fluoro-phenyl)-ethyl]-piperazine

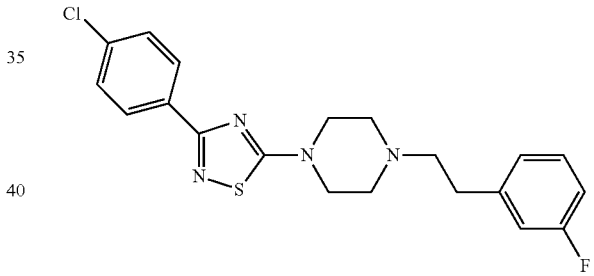

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-3-fluorobenzene as off-white solid. MS (m/e): 403.3 (MH⁺).

Example 22

1-[2-(3-Chloro-phenyl)-ethyl]-4-[3-(4-chloro-phenyl)-[1,2,4]thiadiazol-5-yl]-piperazine

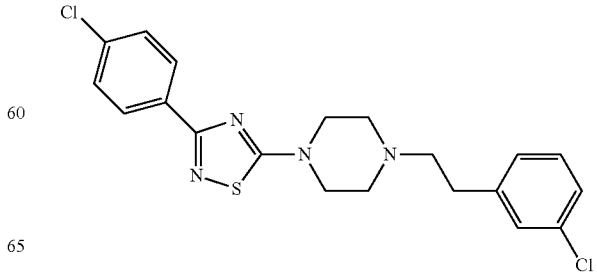

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-3-chlorobenzene as light yellow solid. MS (m/e): 419.2 (MH$^+$).

Example 23

1-[3-(4-Chloro-phenyl)-[1,2,4]thiadiazol-5-yl]-4-(2-m-tolyl-ethyl)-piperazine

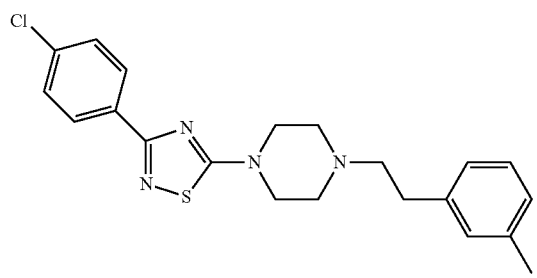 [SMILES: Cc1cccc(CCN2CCN(c3nc(-c4ccc(Cl)cc4)ns3)CC2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-3-methylbenzene as light yellow solid. MS (m/e): 399.2 (MH$^+$).

Example 24

1-[3-(4-Chloro-phenyl)-[1,2,4]thiadiazol-5-yl]-4-[2-(4-fluoro-phenyl)-ethyl]-piperazine

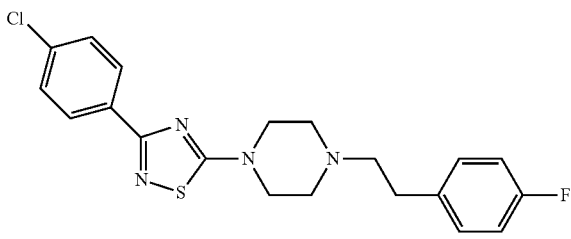 [SMILES: Fc1ccc(CCN2CCN(c3nc(-c4ccc(Cl)cc4)ns3)CC2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-fluorobenzene as light yellow solid. MS (m/e): 403.3 (MH$^+$).

Example 25

1-[2-(4-Chloro-phenyl)-ethyl]-4-[3-(4-chloro-phenyl)-[1,2,4]thiadiazol-5-yl]-piperazine

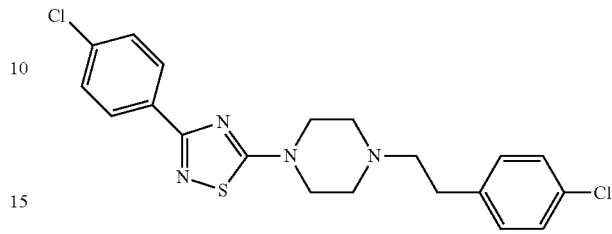

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-chlorobenzene as light yellow solid. MS (m/e): 419.1 (MH$^+$).

Example 26

1-[3-(4-Chloro-phenyl)-[1,2,4]thiadiazol-5-yl]-4-(2-p-tolyl-ethyl)-piperazine

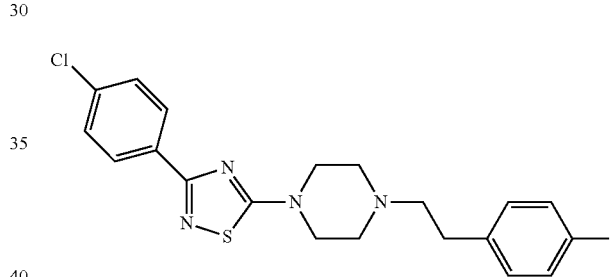

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-methylbenzene as light yellow solid. MS (m/e): 399.1 (MH$^+$).

Example 27

1-[3-(4-Chloro-phenyl)-[1,2,4]thiadiazol-5-yl]-4-[2-(2-methoxy-phenyl)-ethyl]-piperazine

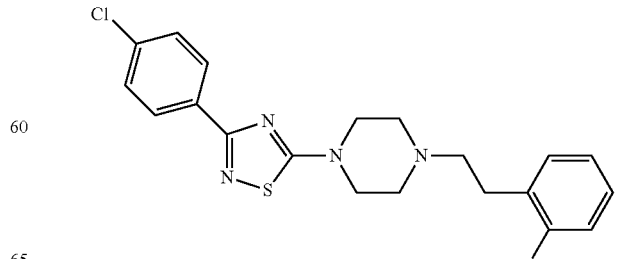

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-2-methoxybenzene as light yellow solid. MS (m/e): 415.2 (MH+).

Example 28

1-[3-(4-Chloro-phenyl)-[1,2,4]thiadiazol-5-yl]-4-[2-(2-fluoro-phenyl)-ethyl]-piperazine

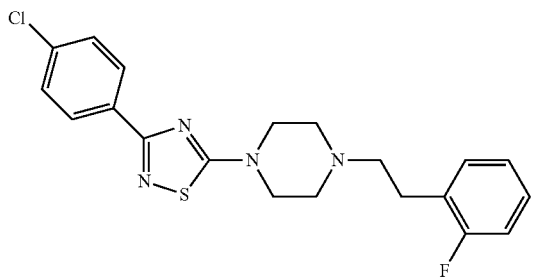 [SMILES: Fc1ccccc1CCN1CCN(c2nc(-c3ccc(Cl)cc3)ns2)CC1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-2-fluorobenzene as light yellow solid. MS (m/e): 403.2 (MH+).

Example 29

1-[2-(2-Chloro-phenyl)-ethyl]-4-[3-(4-chloro-phenyl)-[1,2,4]thiadiazol-5-yl]-piperazine

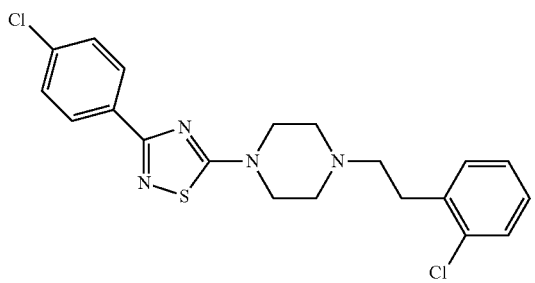 [SMILES: Clc1ccc(-c2nsc(N3CCN(CCc4ccccc4Cl)CC3)n2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-2-chlorobenzene as light yellow solid. MS (m/e): 419.1 (MH+).

Example 30

1-[2-(3-Methoxy-phenyl)-ethyl]-4-[3-(6-trifluoromethyl-pyridin-3-yl)-[1,2,4]thiadiazol-5-yl]-piperazine

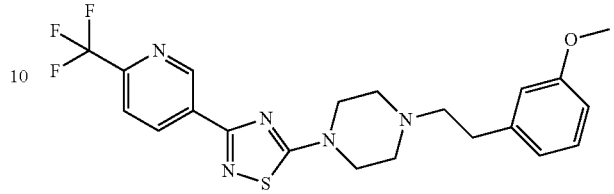

a) 5-(5-Chloro[1,2,4]thiadiazol-3-yl)-2-trifluoromethyl-pyridine

In analogy to the procedure described for the synthesis of 4-(5-Chloro-[1,2,4]thiadiazol-3-yl)-pyridine (example 20, step a) the title compound was prepared from 6-(trifluoromethyl) nicotinimidamide hydrochloride and perchloromethyl mecaptan as light brown solid. MS (m/e): 266.0 (MH+).

b) 1-[2-(3-Methoxy-phenyl)-ethyl]-4-[3-(6-trifluoromethyl-pyridin-3-yl)-[1,2,4]thiadiazol-5-yl]-piperazine In analogy to the procedure described for the synthesis of 1-[2-(3-Methoxy-phenyl)-ethyl]-4-(3-pyridin-4-yl-[1,2,4]thiadiazol-5-yl)-piperazine (Example 20, step b) the title compound was prepared from 5-(5-Chloro-[1,2,4]thiadiazol-3-yl)-2-trifluoromethyl-pyridine and 1-(3-methoxyphenethyl)piperazine dihydrochloride as white solid. MS (m/e): 350.3 (MH+).

Example 31

1-[3-(3,5-Dichloro-phenyl)-[1,2,4]thiadiazol-5-yl]-4-[2-(3-methoxy-phenyl)-ethyl]-piperazine

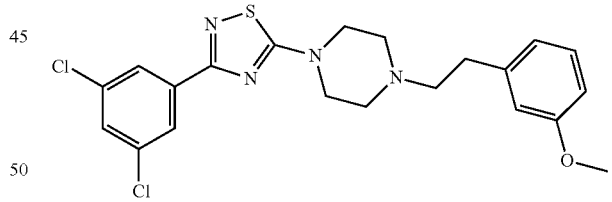

a) 5-Chloro-3-(3,5-dichloro-phenyl)-[1,2,4]thiadiazole

In analogy to the procedure described for the synthesis of 4-(5-Chloro-[1,2,4]thiadiazol-3-yl)-pyridine (example 20, step a) the title compound was prepared from 3,5-dichlorobenzimidamide hydrochloride and perchloromethyl mecaptan as off-white solid. MS (m/e): 265.9 (MH+).

b) 1-[3-(3,5-Dichloro-phenyl)-[1,2,4]thiadiazol-5-yl]-4-[2-(3-methoxy-phenyl)-ethyl]-piperazine In analogy to the procedure described for the synthesis of 1-[2-(3-Methoxy-phenyl)-ethyl]-4-(3-pyridin-4-yl-[1,2,4]

thiadiazol-5-yl)-piperazine (Example 20, step b) the title compound was prepared from 5-Chloro-3-(3,5-dichloro-phenyl)-[1,2,4]thiadiazole and 1-(3-methoxyphenethyl)piperazine dihydrochloride as off-white solid. MS (m/e): 449.1 (MH⁺).

Example 32

1-[3-(4-Chloro-phenyl)-[1,2,4]thiadiazol-5-yl]-4-[3-(3-methoxy-phenyl)-propyl]-piperazine

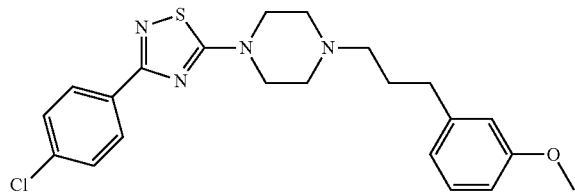 [SMILES: COc1cccc(CCCN2CCN(c3nc(-c4ccc(Cl)cc4)ns3)CC2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(3-bromopropyl)-3-methoxybenzene as light yellow solid. MS (m/e): 429.2 (MH⁺).

Example 33

1-[2-(3-Methoxy-phenyl)-ethyl]-4-(3-thiophen-2-yl-[1,2,4]thiadiazol-5-yl)-piperazine

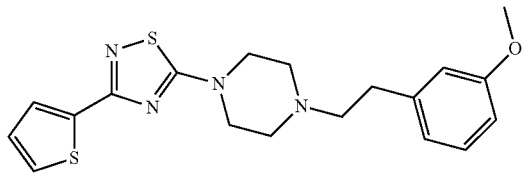 [SMILES: COc1cccc(CCN2CCN(c3nc(-c4cccs4)ns3)CC2)c1]

a) 5-Chloro-3-thiophen-2-yl-[1,2,4]thiadiazole

In analogy to the procedure described for the synthesis of 4-(5-Chloro-[1,2,4]thiadiazol-3-yl)-pyridine (example 20, step a) the title compound was prepared from thiophene-2-carboximidamide hydrochloride and perchloromethyl mecaptan as yellow oil. MS (m/e): 202 (MH⁺).

b) 1-[2-(3-Methoxy-phenyl)-ethyl]-4-(3-thiophen-2-yl-[1,2,4]thiadiazol-5-yl)-piperazine In analogy to the procedure described for the synthesis of 1-[2-(3-Methoxy-phenyl)-ethyl]-4-(3-pyridin-4-yl-[1,2,4]thiadiazol-5-yl)-piperazine (Example 20, step b) the title compound was prepared from 5-Chloro-3-thiophen-2-yl-[1,2,4]thiadiazole and 1-(3-methoxyphenethyl)piperazine dihydrochloride as yellow oil. MS (m/e): 387.2 (MH⁺).

Example 34

1-[3-(4-Fluoro-phenyl)-[1,2,4]thiadiazol-5-yl]-4-[2-(3-methoxy-phenyl)-ethyl]-piperazine

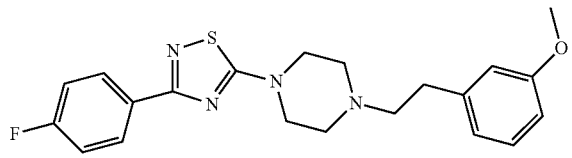 [SMILES: COc1cccc(CCN2CCN(c3nc(-c4ccc(F)cc4)ns3)CC2)c1]

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 5-chloro-3-(4-fluorophenyl)-1,2,4-thiadiazole and 1-(3-methoxyphenethyl)piperazine dihydrochloride as off-white solid. MS (m/e): 399.2 (MH⁺).

Example 35

1-[2-(3-Methoxy-phenyl)-ethyl]-4-[3-(2-methoxy-phenyl)-[1,2,4]thiadiazol-5-yl]-piperazine

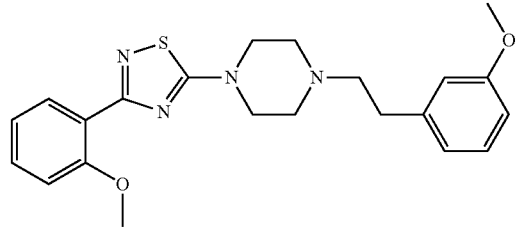 [SMILES: COc1cccc(CCN2CCN(c3nc(-c4ccccc4OC)ns3)CC2)c1]

a) 5-Chloro-3-(2-methoxy-phenyl)-[1,2,4]thiadiazole

In analogy to the procedure described for the synthesis of 4-(5-Chloro-[1,2,4]thiadiazol-3-yl)-pyridine (example 20, step a) the title compound was prepared from 2-methoxybenzimidamide hydrochloride and perchloromethyl mecaptan as yellow oil. MS (m/e): 227.1 (MH⁺).

b) 1-[2-(3-Methoxy-phenyl)-ethyl]-4-[3-(2-methoxy-phenyl)-[1,2,4]thiadiazol-5-yl]-piperazine In analogy to the procedure described for the synthesis of 1-[2-(3-Methoxy-phenyl)-ethyl]-4-(3-pyridin-4-yl-[1,2,4]thiadiazol-5-yl)-piperazine (Example 20, step b) the title compound was prepared from 5-Chloro-3-(2-methoxy-phenyl)-[1,2,4]thiadiazole and 1-(3-methoxyphenethyl)piperazine dihydrochloride as yellow oil. MS (m/e): 411.3 (MH⁺).

Example 36

1-[2-(3-Methoxy-phenyl)-ethyl]-4-[3-(4-trifluoromethoxy-phenyl)-[1,2,4]thiadiazol-5-yl]-piperazine

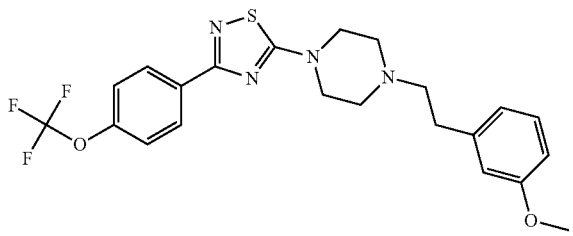 [SMILES: COc1cccc(CCN2CCN(c3nc(-c4ccc(OC(F)(F)F)cc4)ns3)CC2)c1]

a) 5-Chloro-3-(4-trifluoromethoxy-phenyl)-[1,2,4]thiadiazole

In analogy to the procedure described for the synthesis of 4-(5-Chloro-[1,2,4]thiadiazol-3-yl)-pyridine (example 20, step a) the title compound was prepared from 4-(trifluoromethoxy)benzimidamide hydrochloride and perchloromethyl mecaptan as light brown solid. MS (m/e): 280.0 (MH$^+$).

b) 1-[2-(3-Methoxy-phenyl)-ethyl]-4-[3-(4-trifluoromethoxy-phenyl)-[1,2,4]thiadiazol-5-yl]-piperazine In analogy to the procedure described for the synthesis of 1-[2-(3-Methoxy-phenyl)-ethyl]-4-(3-pyridin-4-yl-[1,2,4]thiadiazol-5-yl)-piperazine (Example 20, step b) the title compound was prepared from 5-Chloro-3-(4-trifluoromethoxy-phenyl)-[1,2,4]thiadiazole and 1-(3-methoxyphenethyl)piperazine dihydrochloride as light yellow solid. MS (m/e): 465.3 (MH$^+$).

Example 37

1-[2-(4-Methoxy-phenyl)-ethyl]-4-[3-(4-trifluoromethoxy-phenyl)-[1,2,4]thiadiazol-5-yl]-piperazine

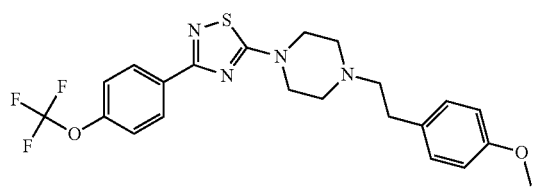 [SMILES: COc1ccc(CCN2CCN(c3nc(-c4ccc(OC(F)(F)F)cc4)ns3)CC2)cc1]

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 5-Chloro-3-(4-trifluoromethoxy-phenyl)-[1,2,4]thiadiazole and 1-(4-methoxyphenethyl)piperazine dihydrochloride as off-white solid. MS (m/e): 465.3 (MH$^+$).

Example 38

1-[3-(4-Chloro-phenyl)-[1,2,4]thiadiazol-5-yl]-4-[2-(3-trifluoromethoxy-phenyl)-ethyl]-piperazine

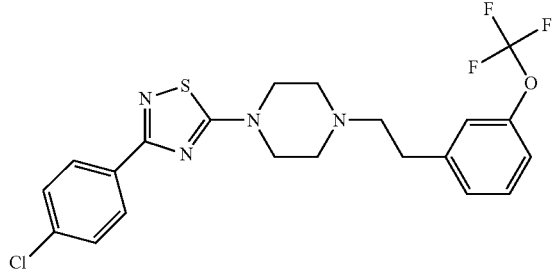 [SMILES: FC(F)(F)Oc1cccc(CCN2CCN(c3nc(-c4ccc(Cl)cc4)ns3)CC2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromo ethyl)-3-(trifluoromethoxy)benzene as off-white solid. MS (m/e): 469.2 (MH$^+$).

Example 39

1-[3-(4-Chloro-phenyl)-[1,2,4]thiadiazol-5-yl]-4-[3-(2-methoxy-phenyl)-propyl]-piperazine

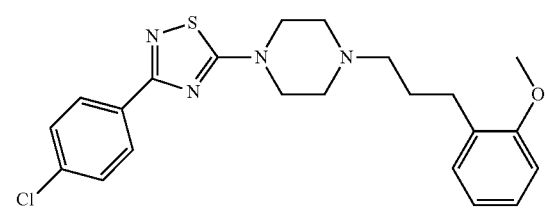 [SMILES: COc1ccccc1CCCN1CCN(c2nc(-c3ccc(Cl)cc3)ns2)CC1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(3-bromopropyl)-2-methoxybenzene as off-white solid. MS (m/e): 429.2 (MH$^+$).

Example 40

1-[2-(4-Methoxy-phenyl)-ethyl]-4-[3-(4-methoxyphenyl)-[1,2,4]thiadiazol-5-yl]-piperazine

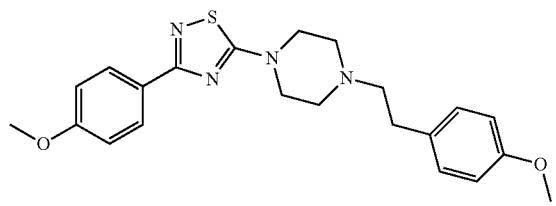

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(4-methoxyphenyl)-1,2,4-thiadiazole and 1-(4-methoxyphenethyl) piperazine dihydrochloride as off-white solid. MS (m/e): 411.2 (MH⁺).

Example 41

1-[3-(3-Chloro-phenyl)-[1,2,4]thiadiazol-5-yl]-4-[2-(4-methoxy-phenyl)-ethyl]-piperazine

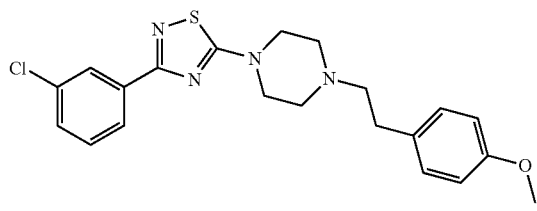 [SMILES: COc1ccc(CCN2CCN(c3nc(-c4cccc(Cl)c4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-chlorophenyl)-1,2,4-thiadiazole and 1-(4-methoxyphenethyl) piperazine dihydrochloride as off-white solid. MS (m/e): 415.3 (MH⁺).

Example 42

1-[2-(4-Methoxy-phenyl)-ethyl]-4-[3-(6-trifluoromethyl-pyridin-3-yl)-[1,2,4]thiadiazol-5-yl]-piperazine

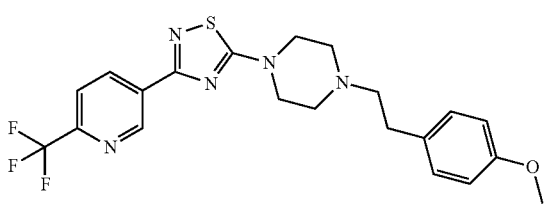 [SMILES: COc1ccc(CCN2CCN(c3nc(-c4ccc(C(F)(F)F)nc4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-(5-Chloro-[1,2,4]thiadiazol-3-yl)-2-trifluoromethyl-pyridine and 1-(4-methoxyphenethyl) piperazine dihydrochloride as off-white solid. MS (m/e): 450.2 (MH⁺).

Example 43

1-[2-(4-Methoxy-phenyl)-ethyl]-4-(3-pyridin-4-yl-[1,2,4]thiadiazol-5-yl)-piperazine

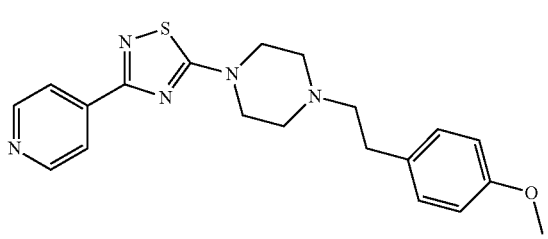 [SMILES: COc1ccc(CCN2CCN(c3nc(-c4ccncc4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-(5-Chloro-[1,2,4]thiadiazol-3-yl)-pyridine and 1-(4-methoxyphenethyl) piperazine dihydrochloride as off-white solid. MS (m/e): 382.3 (MH⁺).

Example 44

1-[2-(4-Methoxy-phenyl)-ethyl]-4-(3-thiophen-2-yl-[1,2,4]thiadiazol-5-yl)-piperazine

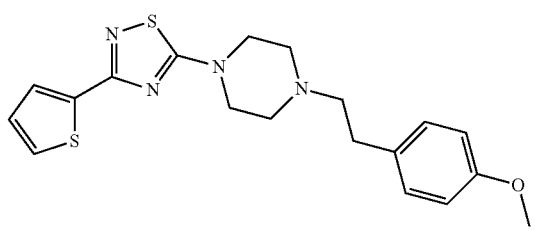 [SMILES: COc1ccc(CCN2CCN(c3nc(-c4cccs4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-thiophen-2-yl-[1,2,4]thiadiazole and 1-(4-methoxyphenethyl) piperazine dihydrochloride as off-white solid. MS (m/e): 387.2 (MH⁺).

Example 45

1-[2-(4-Methoxy-phenyl)-ethyl]-4-[3-(2-methoxy-phenyl)[1,2,4]thiadiazol-5-yl]-piperazine

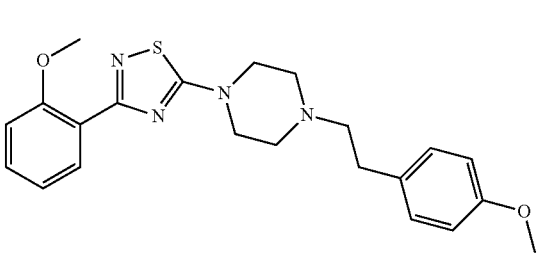 [SMILES: COc1ccc(CCN2CCN(c3nc(-c4ccccc4OC)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(2-methoxy-phenyl)-[1,2,4]thiadiazole and 1-(4-methoxyphenethyl) piperazine dihydrochloride as yellow oil. MS (m/e): 411.2 (MH⁺).

Example 46

1-[3-(3,5-Dichloro-phenyl)-[1,2,4]thiadiazol-5-yl]-4-[2-(4-methoxy-phenyl)-ethyl]-piperazine

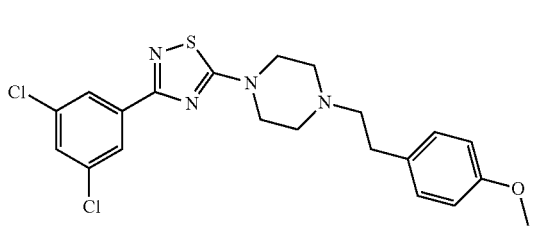 [SMILES: COc1ccc(CCN2CCN(c3nc(-c4cc(Cl)cc(Cl)c4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(3,5-dichloro-phenyl)-[1,2,4]thiadiazole and 1-(4-methoxyphenethyl) piperazine dihydrochloride as off-white solid. MS (m/e): 449.2 (MH$^+$).

Example 47

1-[3-(4-Fluoro-phenyl)-[1,2,4]thiadiazol-5-yl]-4-[2-(4-methoxy-phenyl)-ethyl]-piperazine

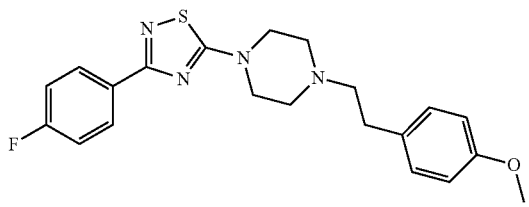 [SMILES: COc1ccc(CCN2CCN(c3nc(-c4ccc(F)cc4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(4-fluorophenyl)-1,2,4-thiadiazole and 1-(4-methoxyphenethyl) piperazine dihydrochloride as off-white solid. MS (m/e): 399.2 (MH$^+$).

Example 48

1-[3-(3-Chloro-phenyl)-[1,2,4]thiadiazol-5-yl]-4-[2-(3-methoxy-phenyl)-ethyl]-piperazine

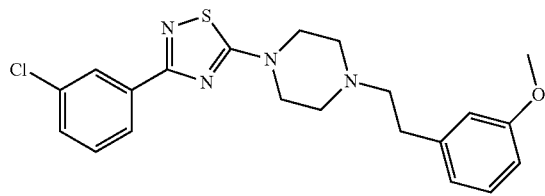 [SMILES: COc1cccc(CCN2CCN(c3nc(-c4cccc(Cl)c4)ns3)CC2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-chlorophenyl)-1,2,4-thiadiazole and 1-(3-methoxyphenethyl) piperazine dihydrochloride as off-white solid. MS (m/e): 415.3 (MH$^+$).

Example 49

1-[2-(3-Methoxy-phenyl)-ethyl]-4-[3-(4-methoxy-phenyl)-[1,2,4]thiadiazol-5-yl]-piperazine

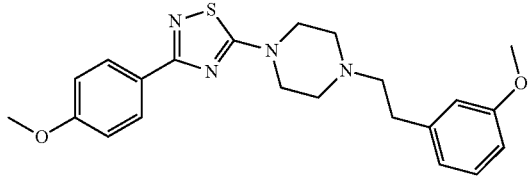 [SMILES: COc1ccc(-c2nsc(N3CCN(CCc4cccc(OC)c4)CC3)n2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(4-methoxyphenyl)-1,2,4-thiadiazole and 1-(3-methoxyphenethyl) piperazine dihydrochloride as white solid. MS (m/e): 411.3 (MH$^+$).

Example 50

1-[3-(4-Chloro-phenyl)-[1,2,4]thiadiazol-5-yl]-4-[2-(4-ethoxy-phenyl)-ethyl]-piperazine

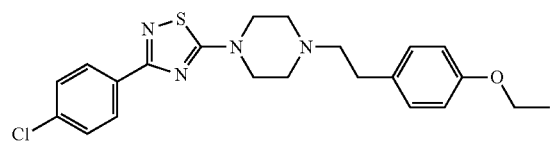 [SMILES: CCOc1ccc(CCN2CCN(c3nc(-c4ccc(Cl)cc4)ns3)CC2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-ethoxybenzene as off-white solid. MS (m/e): 429.3 (MH$^+$).

Example 51

1-[3-(4-Chloro-phenyl)-[1,2,4]thiadiazol-5-yl]-4-[2-(3-isopropoxy-phenyl)-ethyl]-piperazine

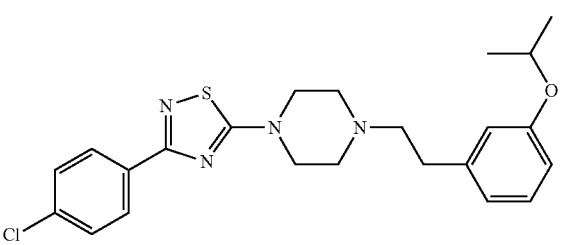 [SMILES: CC(C)Oc1cccc(CCN2CCN(c3nc(-c4ccc(Cl)cc4)ns3)CC2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromo ethyl)-3-isopropoxybenzene as light yellow solid. MS (m/e): 443.2 (MH$^+$).

Example 52

1-[3-(4-Chloro-phenyl)-[1,2,4]thiadiazol-5-yl]-4-[3-(4-methoxy-phenyl)-propyl]-piperazine

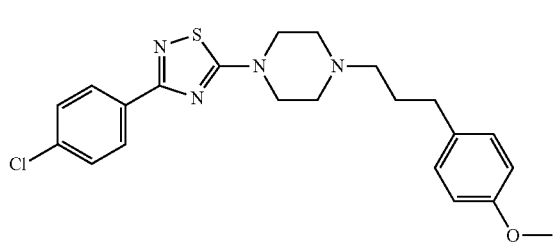 [SMILES: COc1ccc(CCCN2CCN(c3nc(-c4ccc(Cl)cc4)ns3)CC2)cc1]

In analogy to the procedure described for the synthesis of 1-(2-Methyl-benzyl)-4-(3-p-tolyl-[1,2,4]thiadiazol-5-yl)- piperazine (example 6) the title compound was prepared from 1-[3-(4-Chloro-phenyl)-[1,2,4]thiadiazol-5-yl]-piperazine and 1-(3-bromopropyl)-4-methoxybenzene as off-white solid. MS (m/e): 429.3 (MH⁺).

Example 53

2-{4-[3-(4-Chloro-phenyl)-[1,2,4]thiadiazol-5-yl]-piperazin-1-yl}-1-(4-methoxy-phenyl)-ethanone

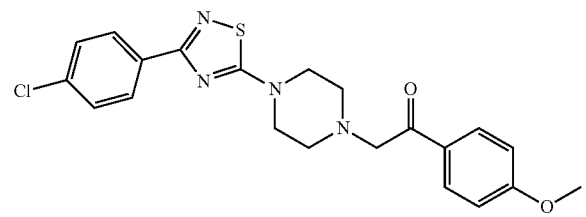 [SMILES: COc1ccc(C(=O)CN2CCN(c3nc(-c4ccc(Cl)cc4)ns3)CC2)cc1]

A mixture of 3-(4-chlorophenyl)-5-(piperazin-1-yl)-1,2,4-thiadiazole (539 mg, 1.92 mmol), 2-bromo-4'-methoxyacetophenone (440 mg, 1.92 mmol) and DIPEA (744 mg, 1.01 ml, 5.76 mmol) in 10 mL EtOH was stirred for 2 h at RT. Another portion 2-bromo-4'-methoxyacetophenone (220 mg, 960 µmol) was added and stirring continued for 2 h. The reaction was filtered off and washed with MeOH (4×5 mL) and Et₂O (2×5 mL). The filter cake was dried in vacuo at 50° C. to yield 526 mg (64%) of the title compound as white solid. MS (m/e): 429.2 (MH⁺).

Example 54

2-{4-[3-(4-Chloro-phenyl)-[1,2,4]thiadiazol-5-yl]-piperazin-1-yl}-1-(4-methoxy-phenyl)-ethanol

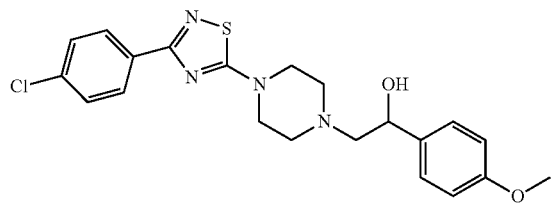 [SMILES: COc1ccc(C(O)CN2CCN(c3nc(-c4ccc(Cl)cc4)ns3)CC2)cc1]

A mixture of 2-(4-(3-(4-chlorophenyl)-1,2,4-thiadiazol-5-yl)piperazin-1-yl)-1-(4-methoxyphenyl)ethanone (75 mg, 175 µmol) and NaBH4 (10 mg, 264 µmol) in THF (5 mL) and MeOH (1 mL) was stirred at RT. Water (5 mL) and 10% aq.Na₂CO₃ (5 mL) was added and stirred for 10 min. The mixture was extracted with EtOAc; the organic layers were washed with brine (20 mL), dried over Na₂SO₄, filtered off and concentrated in vacuo.

The residue was purified by column chromatography on silica eluting with EtOAc to yield after evaporation of the product containing fraction 70 mg (93%) of the title compound as white solid. MS (m/e): 431.2 (MH⁺).

Example 55

1-[3-(4-Chloro-2-fluoro-phenyl)-[1,2,4]thiadiazol-5-yl]-4-[2-(3-methoxy-phenyl)-ethyl]-piperazine

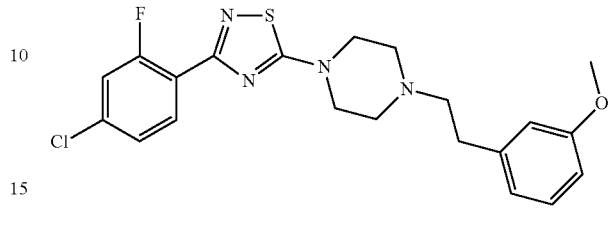

a) 5-Chloro-3-(4-chloro-2-fluoro-phenyl)-[1,2,4]thiadiazole

In analogy to the procedure described for the synthesis of 4-(5-Chloro-[1,2,4]thiadiazol-3-yl)-pyridine (example 20, step a) the title compound was prepared from 4-chloro-2-fluorobenzimidamide hydrochloride and perchloromethyl mecaptan as yellow solid. MS (m/e): 248.0 (MH⁺).

b) 1-[3-(4-Chloro-2-fluoro-phenyl)-[1,2,4]thiadiazol-5-yl]-4-[2-(3-methoxy-phenyl)-ethyl]-piperazine In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(4-chloro-2-fluoro-phenyl)-[1,2,4]thiadiazole and 1-(3-methoxyphenethyl) piperazine dihydrochloride as yellow oil. MS (m/e): 433.2 (MH⁺).

Example 56

1-[3-(4-Chloro-2-fluoro-phenyl)-[1,2,4]thiadiazol-5-yl]-4-[2-(4-methoxy-phenyl)-ethyl]-piperazine

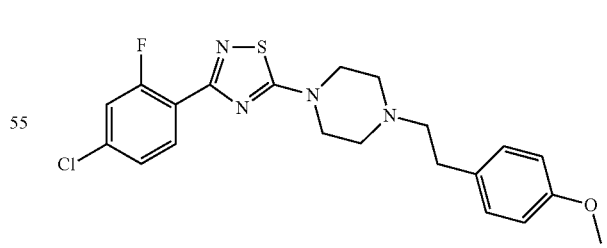

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(4-chloro-2-fluoro-phenyl)-[1,2,4]thiadiazole and 1-(4-methoxyphenethyl) piperazine dihydrochloride as light yellow oil. MS (m/e): 433.2 (MH⁺).

Example 57

1-[3-(2-Chloro-phenyl)-[1,2,4]thiadiazol-5-yl]-4-[2-(3-methoxy-phenyl)-ethyl]-piperazine

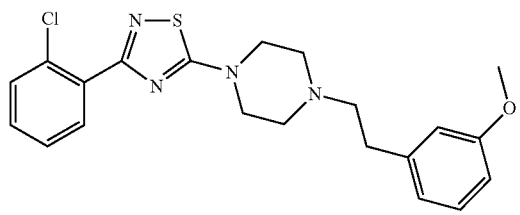 [SMILES: COc1cccc(CCN2CCN(c3nc(-c4ccccc4Cl)ns3)CC2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(2-chloro-phenyl)-[1,2,4]thiadiazole and 1-(3-methoxyphenethyl) piperazine dihydrochloride as yellow oil. MS (m/e): 415.3 (MH$^+$).

Example 58

1-[3-(2-Chloro-phenyl)-[1,2,4]thiadiazol-5-yl]-4-[2-(4-methoxy-phenyl)-ethyl]-piperazine

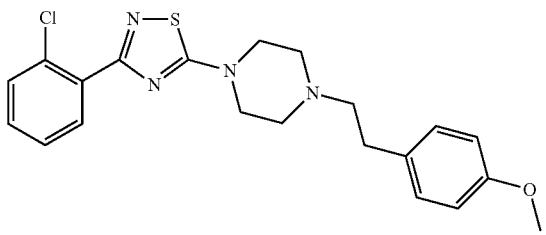 [SMILES: COc1ccc(CCN2CCN(c3nc(-c4ccccc4Cl)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(2-chloro-phenyl)-[1,2,4]thiadiazole and 1-(4-methoxyphenethyl) piperazine dihydrochloride as light yellow solid. MS (m/e): 415.3 (MH$^+$).

Example 59

1-[3-(4-Chloro-phenyl)-[1,2,4]thiadiazol-5-yl]-4-[2-(4-methoxy-phenyl)-allyl]-piperazine

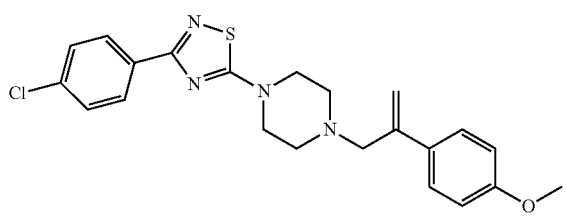 [SMILES: C=C(CN1CCN(c2nc(-c3ccc(Cl)cc3)ns2)CC1)c1ccc(OC)cc1]

A mixture of methyltriphenylphosphonium bromide/sodium amide (57.7 mg, 146 μmol) was combined with THF (5 mL) to give a yellow suspension and stirred for 1 h at RT. 2-(4-(3-(4-chlorophenyl)-1,2,4-thiadiazol-5-yl)piperazin-1-yl)-1-(4-methoxyphenyl)ethanone (50 mg, 117 μmol) dissolved in THF (3 mL) was added drop-wise via syringe over 5 min. The resulting orange suspension was stirred over night at RT. Water (10 mL) and EtOAc (10 mL) was added and stirred for 10 min. The aqueous layer was separated and extracted with EtOAc (1×10 mL). The organic layers were washed with brine (1×10 mL), dried over Na$_2$SO$_4$, filtered off and concentrated in vacuo. The residue was purified by column chromatography on silica eluting with a gradient formed from heptane and EtOAc to yield, after evaporation of the product containing fraction, 33 mg (66%) of the title compound as off-white solid. MS (m/e): 427.2 (MH$^+$).

Example 60

2-{4-[3-(4-Chloro-phenyl)-[1,2,4]thiadiazol-5-yl]-piperazin-1-yl}-1-(3-methoxy-phenyl)-ethanone

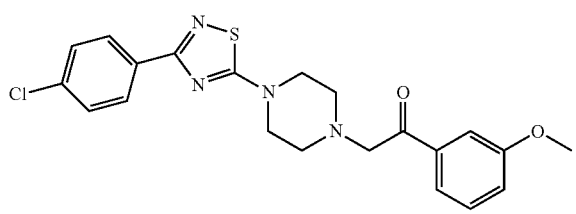

In analogy to the procedure described for the synthesis of 2-{4-[3-(4-Chloro-phenyl)-[1,2,4]thiadiazol-5-yl]-piperazin-1-yl}-1-(4-methoxy-phenyl)-ethanone (example 53) the title compound was prepared from 3-(4-chlorophenyl)-5-(piperazin-1-yl)-1,2,4-thiadiazole and 2-bromo-3'-methoxy-acetophenone as off-white solid. MS (m/e): 429.2 (MH$^+$).

Example 61

2-{4-[3-(4-Chloro-phenyl)-[1,2,4]thiadiazol-5-yl]-piperazin-1-yl}-1-(3-methoxy-phenyl)-ethanol

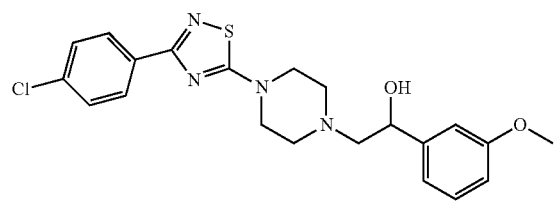 [SMILES: COc1cccc(C(O)CN2CCN(c3nc(-c4ccc(Cl)cc4)ns3)CC2)c1]

In analogy to the procedure described for the synthesis of 2-{4-[3-(4-Chloro-phenyl)-[1,2,4]thiadiazol-5-yl]-piperazin-1-yl}-1-(4-methoxy-phenyl)-ethanol (Example 54) the title compounds was prepared from 2-{4-[3-(4-Chloro-phenyl)-[1,2,4]thiadiazol-5-yl]-piperazin-1-yl}-1-(3-methoxy-phenyl)-ethanone through reduction as white solid. MS (m/e): 431.3 (MH$^+$).

Example 62

2-{4-[3-(4-Chloro-phenyl)-[1,2,4]thiadiazol-5-yl]-piperazin-1-yl}-1-(3-fluoro-phenyl)-ethanone

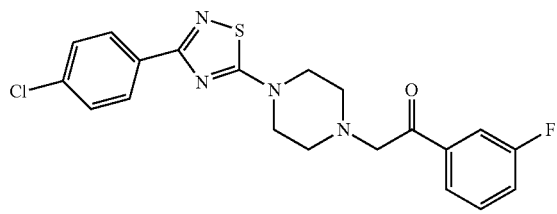 [SMILES: O=C(CN1CCN(c2nc(-c3ccc(Cl)cc3)ns2)CC1)c1cccc(F)c1]

In analogy to the procedure described for the synthesis of 2-{4-[3-(4-Chloro-phenyl)-[1,2,4]thiadiazol-5-yl]-piperazin-1-yl}-1-(4-methoxy-phenyl)-ethanone (example 53) the title compound was prepared from 3-(4-chlorophenyl)-5-(piperazin-1-yl)-1,2,4-thiadiazole and 2-bromo-3'-fluoroacetophenone as white solid. MS (m/e): 417.1 (MH$^+$).

Example 63

2-{4-[3-(4-Chloro-phenyl)-[1,2,4]thiadiazol-5-yl]-piperazin-1-yl}-1-(3-fluoro-phenyl)-ethanol

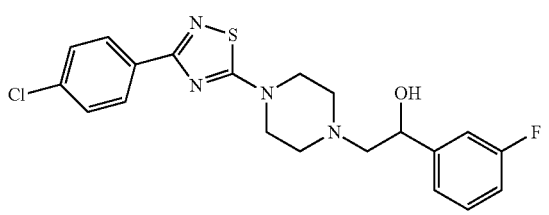 [SMILES: OC(CN1CCN(c2nc(-c3ccc(Cl)cc3)ns2)CC1)c1cccc(F)c1]

In analogy to the procedure described for the synthesis of 2-{4-[3-(4-Chloro-phenyl)-[1,2,4]thiadiazol-5-yl]-piperazin-1-yl}-1-(4-methoxy-phenyl)-ethanol (Example 54) the title compound was prepared from 2-{4-[3-(4-Chloro-phenyl)-[1,2,4]thiadiazol-5-yl]-piperazin-1-yl}-1-(3-fluoro-phenyl)-ethanone through reduction as white solid. MS (m/e): 431.3 (MH$^+$).

Example 64

1-[3-(4-Chloro-phenyl)-[1,2,4]thiadiazol-5-yl]-4-[2-fluoro-2-(4-methoxy-phenyl)-ethyl]-piperazine

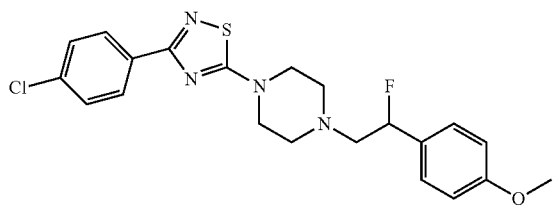 [SMILES: COc1ccc(C(F)CN2CCN(c3nc(-c4ccc(Cl)cc4)ns3)CC2)cc1]

A mixture of 2-(4-(3-(4-chlorophenyl)-1,2,4-thiadiazol-5-yl)piperazin-1-yl)-1-(4-methoxyphenyl)ethanol (30 mg, 69.6 µmol) and DAST (22.4 mg, 18.4 µl, 139 µmol) in 2 mL DCM at 0-5° C. was warmed to RT and stirred for 2 h. 10% aq. Na$_2$CO$_3$-solution was added and stirred for 10 min. The organic layer was separated and concentrated in vacuo. The residue was purified by column chromatography on silica eluting with a gradient formed from heptane and EtOAc to yield, after evaporation of the product containing fraction, 24 mg (80%) of the title compound as light yellow solid. MS (m/e): 433.3 (MH$^+$).

Example 65

1-[3-(4-Chloro-phenyl)-[1,2,4]thiadiazol-5-yl]-4-[2-fluoro-2-(3-methoxy-phenyl)-ethyl]-piperazine

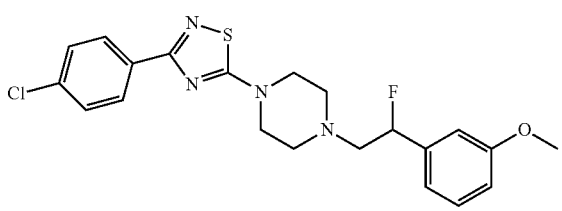 [SMILES: COc1cccc(C(F)CN2CCN(c3nc(-c4ccc(Cl)cc4)ns3)CC2)c1]

In analogy to the procedure described for the synthesis of 1-[3-(4-Chloro-phenyl)-[1,2,4]thiadiazol-5-yl]-4-[2-fluoro-2-(4-methoxy-phenyl)-ethyl]-piperazine (Example 64) the title compound was prepared from 2-{4-[3-(4-Chloro-phenyl)-[1,2,4]thiadiazol-5-yl]-piperazin-1-yl}-1-(3-methoxy-phenyl)-ethanol and DAST as light yellow solid. MS (m/e): 433.3 (MH$^+$).

Example 66

1-[3-(4-Fluoro-2-methoxy-phenyl)-[1,2,4]thiadiazol-5-yl]-4-[2-(3-methoxy-phenyl)-ethyl]-piperazine

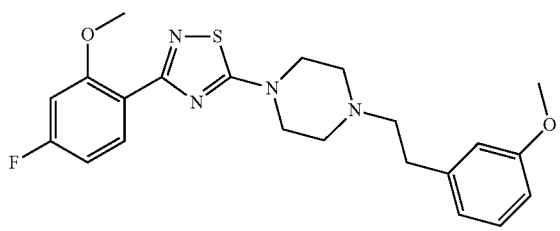 [SMILES: COc1cccc(CCN2CCN(c3nc(-c4ccc(F)cc4OC)ns3)CC2)c1]

a) 5-Chloro-3-(4-fluoro-2-methoxy-phenyl)-[1,2,4]thiadiazole

In analogy to the procedure described for the synthesis of 4-(5-Chloro-[1,2,4]thiadiazol-3-yl)-pyridine (example 20, step a) the title compound was prepared from 4-fluoro-2-methoxybenzimidamide hydrochloride and perchloromethyl mecaptan as yellow oil. MS (m/e): 245.0 (MH$^+$).

b) 1-[3-(4-Fluoro-2-methoxy-phenyl)-[1,2,4]thiadiazol-5-yl]-4-[2-(3-methoxy-phenyl)-ethyl]-piperazine In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(4-fluoro-2-methoxy-phenyl)-[1,2,4]thiadiazole and 1-(3-methoxyphenethyl) piperazine dihydrochloride as yellow oil. MS (m/e): 429.4 (MH$^+$).

Example 67

1-[3-(4-Fluoro-2-methoxy-phenyl)-[1,2,4]thiadiazol-5-yl]-4-[2-(4-methoxy-phenyl)-ethyl]-piperazine

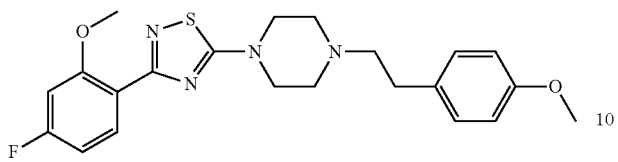

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-3-(4-fluoro-2-methoxy-phenyl)-[1,2,4]thiadiazole and 1-(4-methoxyphenethyl) piperazine dihydrochloride as yellow oil. MS (m/e): 429.3 (MH$^+$).

Example 68

1-[1-(4-Chloro-phenyl)-cyclopropylmethyl]-4-[3-(4-chloro-phenyl)-[1,2,4]thiadiazol-5-yl]-piperazine

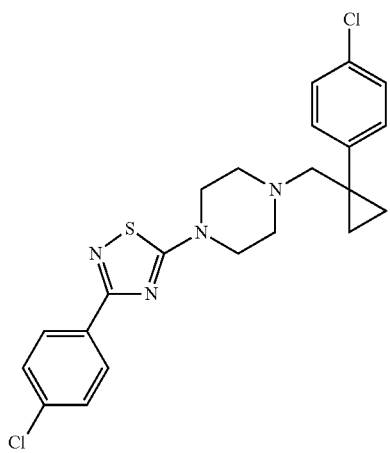 [SMILES: Clc1ccc(-c2nsc(N3CCN(CC4(c5ccc(Cl)cc5)CC4)CC3)n2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(1-(bromomethyl)cyclopropyl)-4-chlorobenzene as white solid. MS (m/e): 455.1 (MH$^+$).

Example 69

1-[3-(4-Chloro-phenyl)-[1,2,4]thiadiazol-5-yl]-4-[2-(3-difluoromethoxy-phenyl)-ethyl]-piperazine

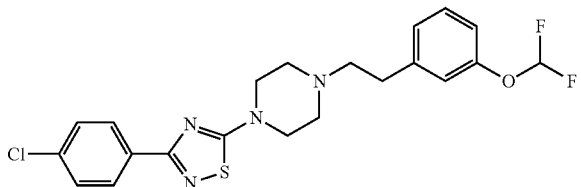

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-3-(difluoromethoxy)benzene as yellow solid. MS (m/e): 451.1 (MH$^+$).

Example 70

1-[3-(4-Chloro-phenyl)-[1,2,4]thiadiazol-5-yl]-4-[2-(4-difluoromethoxy-phenyl)-ethyl]-piperazine

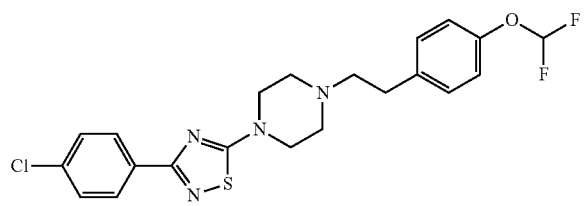 [SMILES: FC(F)Oc1ccc(CCN2CCN(c3nc(-c4ccc(Cl)cc4)ns3)CC2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-(difluoromethoxy)benzene as off-white solid. MS (m/e): 451.0 (MH$^+$).

Example 71

1-[3-(4-Chloro-phenyl)-[1,2,4]thiadiazol-5-yl]-4-[2-(4-isopropoxy-phenyl)-ethyl]-piperazine

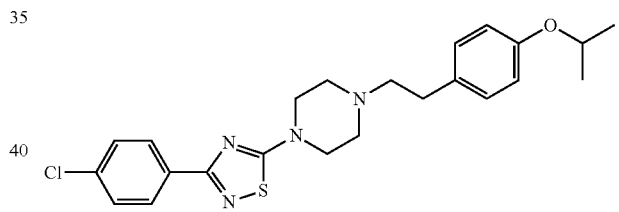

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromo ethyl)-4-isopropoxybenzene as off-white solid. MS (m/e): 433.3 (MH$^+$).

Example 72

1-[3-(4-Chloro-phenyl)-[1,2,4]thiadiazol-5-yl]-4-[2-(4-methoxy-phenyl)-propyl]-piperazine

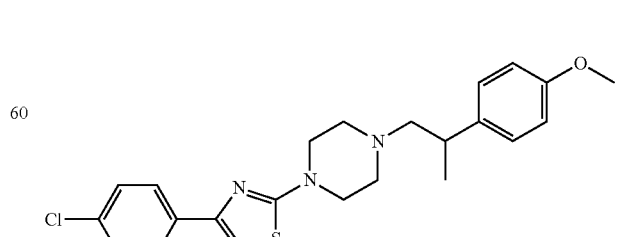

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(1-bromopropan-2-yl)-4-methoxybenzene as off-white solid. MS (m/e): 429.2 (MH⁺).

Example 73

1-[3-(4-Chloro-phenyl)-[1,2,4]thiadiazol-5-yl]-4-[2-(4-methoxy-phenyl)-1-methyl-ethyl]-piperazine

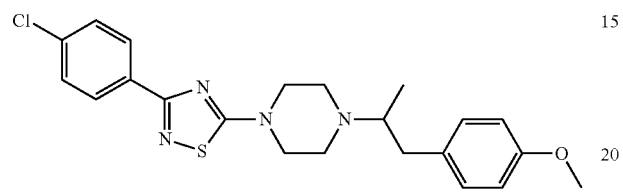

A mixture of 3-(4-chlorophenyl)-5-(piperazin-1-yl)-1,2,4-thiadiazole (100 mg, 356 μmol), 4-methoxyphenylacetophenone (64.3 mg, 392 μmol) and titanium IV propoxide (152 mg, 158 μl, 534 μmol) in 2 mL THF was stirred for 3 h at RT. NaBH₄ (40.4 mg, 1.07 mmol) was added in three portions. MeOH (0.2 mL) was added and stirred over the weekend at RT. Water (5 mL), EtOAc (10 mL) and aq. 2N NaOH (3 mL) was added, stirred for 10 min and filtered over a dicalit-plug. The aqueous layer was separated and extracted once with EtOAc (20 mL). The organic layers were washed with brine (1×20 mL), dried over Na₂SO₄, filtered off and concentrated in vacuo. The residue was purified by column chromatography on silica eluting with a gradient formed from heptane and EtOAc and again with preparative HPLC to yield, after evaporation of the product containing fraction, 39 mg (25%) of the title compound as off-white solid. MS (m/e): 429.2 (MH⁺).

Example 75

1-[3-(4-Chloro-phenyl)-[1,2,4]thiadiazol-5-yl]-4-[2-(2-methoxy-pyridin-4-yl)-ethyl]-piperazine

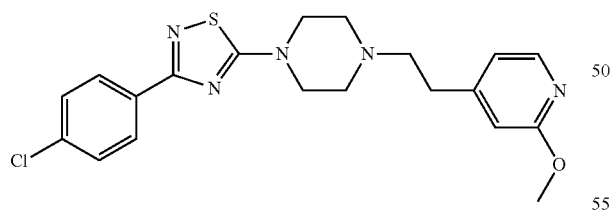

a) 4-(2-Bromo-ethyl)-2-methoxy-pyridine

A mixture of 2-(2-methoxypyridin-4-yl)ethanol (commercially available) (700 mg, 4.57 mmol,), CBr₄ (2.27 g, 6.85 mmol) and triphenylphosphine (1.8 g, 6.85 mmol) in 75 mL toluene was stirred at RT for 64 h. The mixture was filtered over a silica-plug and washed with toluene. The filtrate concentrated under vacuum to yield the crude product. The residue was purified by column chromatography on silica eluting with a gradient formed from heptane and EtOAc to yield, after evaporation of the product containing fraction, 624 mg (63%) of the title compound as colourless liquid. MS (m/e): 216.2 (MH⁺).

b) 1-[3-(4-Chloro-phenyl)-[1,2,4]thiadiazol-5-yl]-4-[2-(2-methoxy-pyridin-4-yl)-ethyl]-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 4-(2-Bromo-ethyl)-2-methoxy-pyridine as off-white solid. MS (m/e): 416.2 (MH⁺).

Example 76

2-(5-{4-[2-(4-Methoxy-phenyl)-ethyl]-piperazin-1-yl}-[1,2,4]thiadiazol-3-yl)-pyrazine

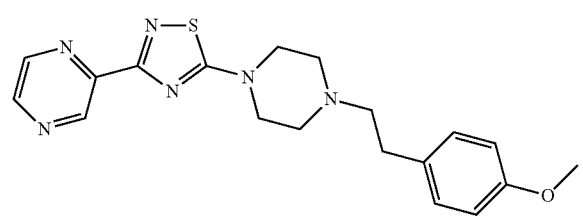 [SMILES: COc1ccc(CCN2CCN(c3nc(-c4cnccn4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(pyrazin-2-yl)-1,2,4-thiadiazole and 1-(4-methoxyphenethyl) piperazine dihydrochloride as off-white solid. MS (m/e): 383.2 (MH⁺).

Example 77

2-(5-{4-[2-(3-Methoxy-phenyl)-ethyl]-piperazin-1-yl}-[1,2,4]thiadiazol-3-yl)-pyrazine

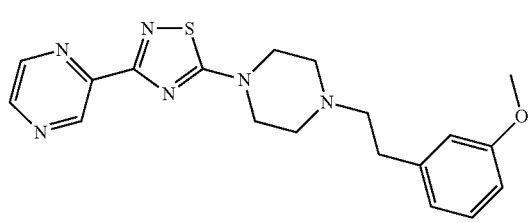 [SMILES: COc1cccc(CCN2CCN(c3nc(-c4cnccn4)ns3)CC2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(pyrazin-2-yl)-1,2,4-thiadiazole and 1-(3-methoxyphenethyl) piperazine dihydrochloride as purple viscous oil. MS (m/e): 383.2 (MH⁺).

Example 78

4-(5-{4-[2-(4-Methoxy-phenyl)-ethyl]-piperazin-1-yl}-[1,2,4]thiadiazol-3-yl)-benzonitrile

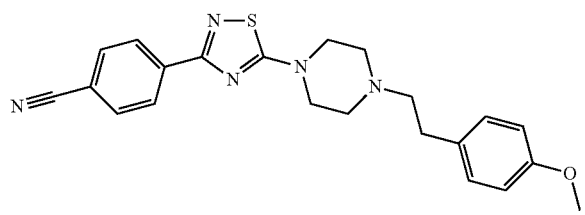 [SMILES: COc1ccc(CCN2CCN(c3nc(-c4ccc(C#N)cc4)ns3)CC2)cc1]

a) 1-(3-Chloro-[1,2,4]thiadiazol-5-yl)-4-[2-(4-methoxy-phenyl)-ethyl]-piperazine A mixture of 1-(4-methoxyphenethyl)piperazine dihydrochloride (1.04 g, 3.55 mmol), 3,5-dichloro-1,2,4-thiadiazole (500 mg, 3.23 mmol) and DIPEA (1.33 g, 1.8 ml, 10.3 mmol) in 23 mL EtOH was stirred for 1 h at RT. The reaction solution was concentrated in vacuo and the crude product was purified by column chromatography on silica eluting with a gradient formed from heptane and EtOAc to yield, after evaporation of the product containing fraction, 1.06 g (97%) of the title compound as white solid. MS (m/e): 339.2 (MH$^+$).

b) 4-(5-{4-[2-(4-Methoxy-phenyl)-ethyl]-piperazin-1-yl}-[1,2,4]thiadiazol-3-yl)-benzonitrile A 5 ml micro wave vial was charged with 3-chloro-5-(4-(4-methoxyphenethyl)piperazin-1-yl)-1,2,4-thiadiazole (50 mg, 148 µmol) in 3 mL DME. 4-Cyanophenylboronic acid (26.0 mg, 177 µmol), Na$_2$CO$_3$ (18.8 mg, 177 µmol), tetrakis(triphenylphosphine) palladium (0) (3.41 mg, 2.95 µmol) and water (1.5 mL) was added. The vial was capped and the mixture was heated in oil bath at 110° C. over night. 2 mL EtOAc were added and the aqueous part was separated. The organic layer was dried over Na$_2$SO$_4$, filtered off and concentrated in vacuo. The crude product was dissolved in MeCN (3 mL)/DIPEA (100 µL) and purified by preparative HPLC on reversed phase eluting with a gradient formed from MeCN, water and NEt$_3$ to yield, after evaporation of the product containing fractions, 13.6 mg (23%) of the title compound as white solid. MS (m/e): 406.3 (MH$^+$).

Example 79

1-[3-(4-Chloro-phenyl)-[1,2,4]thiadiazol-5-yl]-4-[2-(6-methoxy-pyridin-3-yl)-ethyl]-piperazine

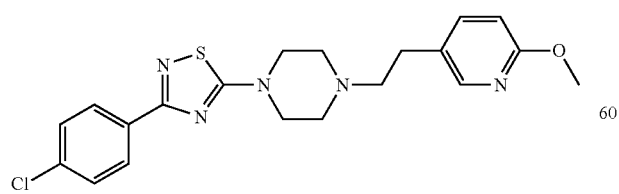

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 5-(2-bromoethyl)-2-methoxypyridine as white solid. MS (m/e): 416.3 (MH$^+$).

Example 80

1-[3-(4-Chloro-phenyl)-[1,2,4]thiadiazol-5-yl]-4-[2-(3-fluoro-4-methoxy-phenyl)-ethyl]-piperazine

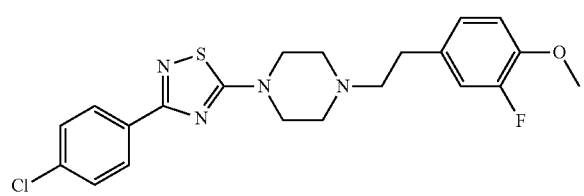 [SMILES: COc1ccc(CCN2CCN(c3nc(-c4ccc(Cl)cc4)ns3)CC2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 4-(2-bromo ethyl)-2-fluoro-1-methoxybenzene as white solid. MS (m/e): 433.2 (MH$^+$).

Example 81

3-(5-{4-[2-(4-Methoxy-phenyl)-ethyl]-piperazin-1-yl}-[1,2,4]thiadiazol-3-yl)-benzonitrile

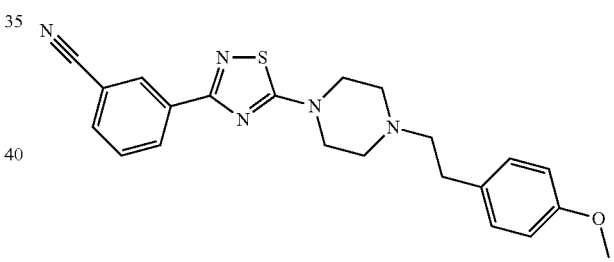

a) 1-(3-Bromo-[1,2,4]thiadiazol-5-yl)-4-[2-(4-methoxy-phenyl)-ethyl]-piperazine In analogy to the procedure described for the synthesis of 1-(3-Chloro-[1,2,4]thiadiazol-5-yl)-4-[2-(4-methoxy-phenyl)-ethyl]-piperazine (example 78, step a) the title compound was prepared from 3-bromo-5-chloro-1,2,4-thiadiazole and 1-(4-methoxyphenethyl)piperazine dihydrochloride as off-white solid. MS (m/e): 383.2 (MH$^+$).

b) 3-(5-{4-[2-(4-Methoxy-phenyl)-ethyl]-piperazin-1-yl}-[1,2,4]thiadiazol-3-yl)-benzonitrile In analogy to the procedure described for the synthesis of 4-(5-{4-[2-(4-Methoxy-phenyl)-ethyl]-piperazin-1-yl}-[1,2,4]thiadiazol-3-yl)-benzonitrile (example 78, step b) the title compound was prepared from 1-(3-Bromo-[1,2,4]thiadiazol-5-yl)-4-[2-(4-methoxy-phenyl)-ethyl]-piperazine and 3-cyanophenylboronic acid under palladium catalysis as light yellow solid. MS (m/e): 406.3 (MH$^+$).

Example 82

1-[3-(3-Chloro-phenyl)-[1,2,4]thiadiazol-5-yl]-4-phenethyl-piperazine

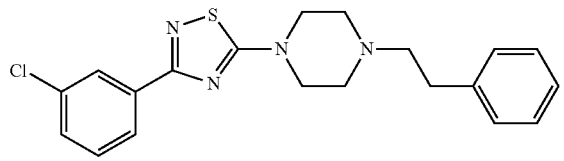 [SMILES: Clc1cccc(-c2nsc(N3CCN(CCc4ccccc4)CC3)n2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-chlorophenyl)-1,2,4-thiadiazole and 1-phenethylpiperazine dihydrochloride as off-white solid. MS (m/e): 385.1 (MH$^+$).

Example 83

1-[3-(3-Fluoro-phenyl)-[1,2,4]thiadiazol-5-yl]-4-phenethyl-piperazine

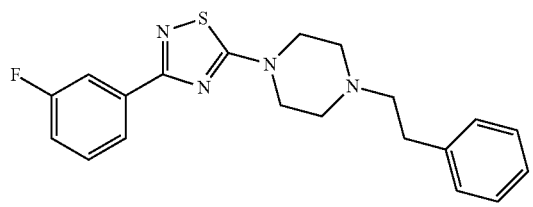 [SMILES: Fc1cccc(-c2nsc(N3CCN(CCc4ccccc4)CC3)n2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-fluorphenyl)-1,2,4-thiadiazole and 1-phenethylpiperazine dihydrochloride as off-white solid. MS (m/e): 369.1 (MH$^+$).

Example 84

1-[3-(3-Fluoro-phenyl)-[1,2,4]thiadiazol-5-yl]-4-[2-(4-methoxy-phenyl)-ethyl]-piperazine

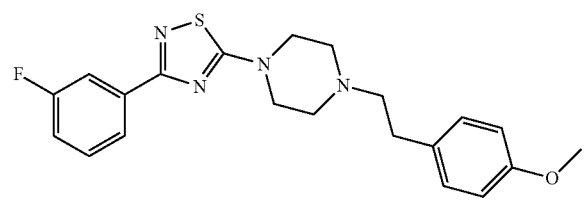 [SMILES: COc1ccc(CCN2CCN(c3nc(-c4cccc(F)c4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-fluorphenyl)-1,2,4-thiadiazole and 1-(4-methoxyphenethyl)piperazine dihydrochloride as off-white solid. MS (m/e): 399.2 (MH$^+$).

Example 85

1-[3-(3-Chloro-phenyl)-[1,2,4]thiadiazol-5-yl]-4-[2-(4-fluoro-phenyl)-ethyl]-piperazine

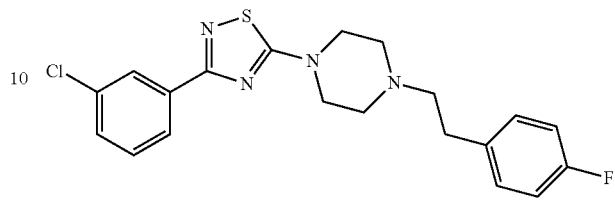

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-chlorophenyl)-1,2,4-thiadiazole and 1-(4-fluorophenethyl)piperazine dihydrochloride as off-white solid. MS (m/e): 40.3.3 (MH$^+$).

Example 86

1-[2-(4-Fluoro-phenyl)-ethyl]-4-[3-(3-fluoro-phenyl)-[1,2,4]thiadiazol-5-yl]-piperazine

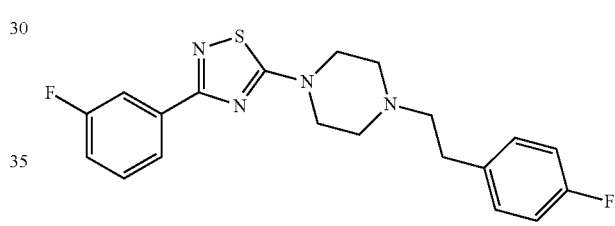

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-fluorphenyl)-1,2,4-thiadiazole and 1-(4-fluorophenethyl)piperazine dihydrochloride as off-white solid. MS (m/e): 387.2 (MH$^+$).

Example 87

1-[2-(4-Chloro-phenyl)-ethyl]-4-[3-(3-chloro-phenyl)-[1,2,4]thiadiazol-5-yl]-piperazine

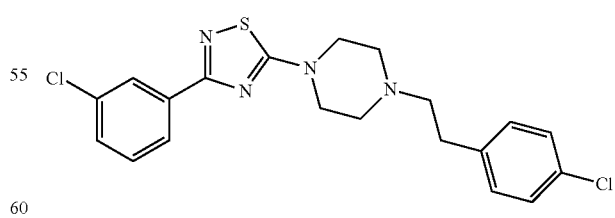

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-chlorophenyl)-1,2,4-thiadiazole and 1-(4-chlorophenethyl)piperazine dihydrochloride as off-white solid. MS (m/e): 419.1 (MH$^+$).

Example 88

1-[2-(4-Chloro-phenyl)-ethyl]-4-[3-(3-fluoro-phenyl)-[1,2,4]thiadiazol-5-yl]-piperazine

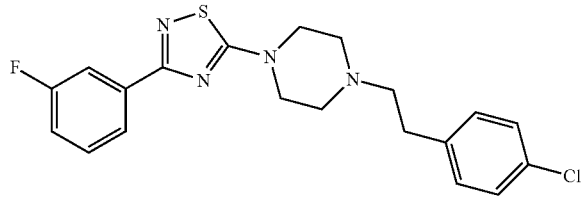 [SMILES: Fc1cccc(-c2nsc(N3CCN(CCc4ccc(Cl)cc4)CC3)n2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-fluorphenyl)-1,2,4-thiadiazole and 1-(4-chlorophenethyl)piperazine dihydrochloride as off-white solid. MS (m/e): 403.3 (MH+).

Example 89

1-[3-(3-Chloro-phenyl)-[1,2,4]thiadiazol-5-yl]-4-[2-(2-methoxy-pyridin-4-yl)-ethyl]-piperazine

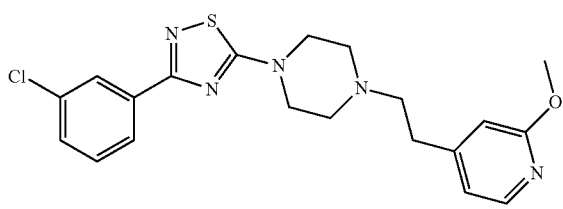

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-chlorophenyl)-1,2,4-thiadiazole and 1-(2-(2-methoxypyridin-4-yl)ethyl)piperazine trihydrochloride as off-white solid. MS (m/e): 416.2 (MH+).

Example 90

1-[3-(3-Fluoro-phenyl)-[1,2,4]thiadiazol-5-yl]-4-[2-(2-methoxy-pyridin-4-yl)-ethyl]-piperazine

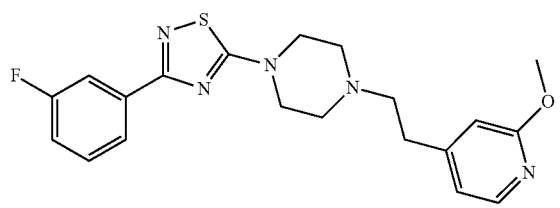 [SMILES: COc1cc(CCN2CCN(c3nc(-c4cccc(F)c4)ns3)CC2)ccn1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(3-fluorphenyl)-1,2,4-thiadiazole and 1-(2-(2-methoxypyridin-4-yl)ethyl)piperazine trihydrochloride as off-white solid. MS (m/e): 400.1 (MH+).

Example 91

1-[3-(5-Chloro-pyridin-3-yl)-[1,2,4]thiadiazol-5-yl]-4-[2-(4-methoxy-phenyl)-ethyl]-piperazine

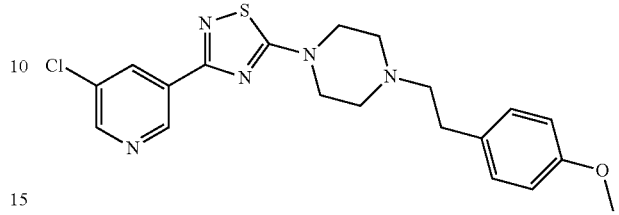

a) 3-Chloro-5-(5-chloro-[1,2,4]thiadiazol-3-yl)-pyridine

In analogy to the procedure described for the synthesis of 4-(5-Chloro-[1,2,4]thiadiazol-3-yl)-pyridine (example 20, step a) the title compound was prepared from 5-chloronicotinimidamide hydrochloride and perchloromethyl mecaptan as light yellow solid. MS (m/e): 232.0 (MH+).

b) 1-[3-(5-Chloro-pyridin-3-yl)-[1,2,4]thiadiazol-5-yl]-4-[2-(4-methoxy-phenyl)-ethyl]-piperazine In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 3-Chloro-5-(5-chloro-[1,2,4]thiadiazol-3-yl)-pyridine and 1-(4-methoxyphenethyl)piperazine dihydrochloride (heating not mandatory) as white solid. MS (m/e): 416.3 (MH+).

Example 92

1-[3-(3-Chloro-phenyl)-[1,2,4]thiadiazol-5-yl]-4-(2-methyl-benzyl)-piperazine

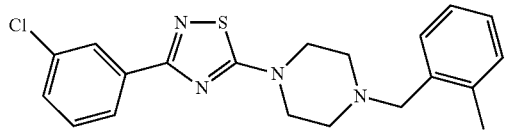 [SMILES: Cc1ccccc1CN1CCN(c2nc(-c3cccc(Cl)c3)ns2)CC1]

a) 4-(3-Bromo-[1,2,4]thiadiazol-5-yl)-piperazine-1-carboxylic acid tert-butyl ester In analogy to the procedure described for the synthesis of 1-(3-Bromo-[1,2,4]thiadiazol-5-yl)-4-[2-(4-methoxy-phenyl)-ethyl]-piperazine (example 81, step a) the title compound was prepared from 3-bromo-5-chloro-1,2,4-thiadiazole and tert-butyl piperazine-1-carboxylate as white solid. MS (m/e): 351.2 (MH+).

b) 1-[3-(3-Chloro-phenyl)-[1,2,4]thiadiazol-5-yl]-piperazine dihydrochloride A mixture of tert-butyl 4-(3-bromo-1,2,4-thiadiazol-5-yl)piperazine-1-carboxylate (1 g, 2.86 mmol), 3-chlorophenylboronic acid (537 mg, 3.44 mmol), Na₂CO₃ (364 mg, 3.44 mmol) and tetrakis(triphenylphosphine) palladium (0) (66.2 mg, 57.3 μmol) in 36 mL DME/12 mL water was heated to 100° C. over night. The mixture was extracted with EtOAc (80 mL)/water (80 mL). The organic layer was dried over Na₂SO₄, filtered off and concentrated in vacuo to give amber oil which was dissolved in 25 mL dioxane, 7.16 mL 4N HCl/dioxane was added and stirred over night at RO. Et₂O was added and the mixture was filtered and washed with Et₂O. The filter cake was dried in vacuo at 50° C. to yield 926 mg (90%) of the intermediate compound as light yellow solid. MS (m/e): 281.0 (MH⁺).

c) 1-[3-(3-Chloro-phenyl)-[1,2,4]thiadiazol-5-yl]-4-(2-methyl-benzyl)-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Chloro-phenyl)-[1,2,4]thiadiazol-5-yl]-piperazine dihydrochloride and 2-methylbenzyl chloride as colorless viscous oil. MS (m/e): 385.1 (MH⁺).

Example 93

1-[3-(3-Chloro-phenyl)-[1,2,4]thiadiazol-5-yl]-4-[2-(6-methoxy-pyridin-3-yl)-ethyl]-piperazine

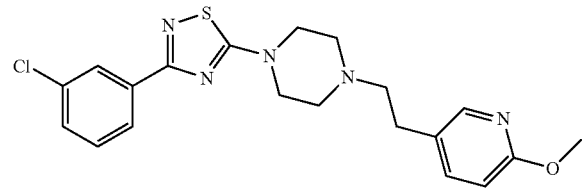 [SMILES: COc1ccc(CCN2CCN(c3nc(-c4cccc(Cl)c4)ns3)CC2)cn1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Chloro-phenyl)-[1,2,4]thiadiazol-5-yl]-piperazine dihydrochloride and 5-(2-bromoethyl)-2-methoxypyridine as off-white solid. MS (m/e): 416.2 (MH⁺).

Example 94

1-[3-(6-Methyl-pyridin-3-yl)-[1,2,4]thiadiazol-5-yl]-4-phenethyl-piperazine

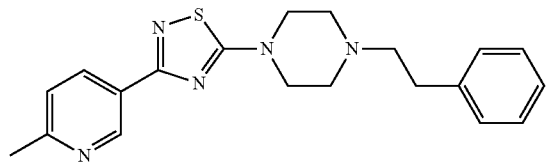 [SMILES: Cc1ccc(-c2nsc(N3CCN(CCc4ccccc4)CC3)n2)cn1]

a) 5-(5-Chloro-[1,2,4]thiadiazol-3-yl)-2-methyl-pyridine

In analogy to the procedure described for the synthesis of 4-(5-Chloro-[1,2,4]thiadiazol-3-yl)-pyridine (example 20, step a) the title compound was prepared from 6-methylnicotinimidamide hydrochloride and perchloromethyl mecaptan as light brown solid. MS (m/e): 212.0 (MH⁺).

b) 1-[3-(6-Methyl-pyridin-3-yl)-[1,2,4]thiadiazol-5-yl]-4-phenethyl-piperazine

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-(5-Chloro-[1,2,4]thiadiazol-3-yl)-2-methyl-pyridine and 1-phenethylpiperazine dihydrochloride as off-white solid. MS (m/e): 366.2 (MH⁺).

Example 95

1-[2-(4-Methoxy-phenyl)-ethyl]-4-[3-(6-methyl-pyridin-3-yl)-[1,2,4]thiadiazol-5-yl]-piperazine

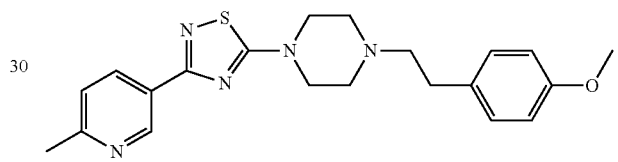

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-(5-Chloro-[1,2,4]thiadiazol-3-yl)-2-methyl-pyridine and 1-(4-methoxyphenethyl)piperazine dihydrochloride as off-white solid. MS (m/e): 396.2 (MH⁺).

Example 96

1-[2-(4-Fluoro-phenyl)-ethyl]-4-[3-(6-methyl-pyridin-3-yl)-[1,2,4]thiadiazol-5-yl]-piperazine

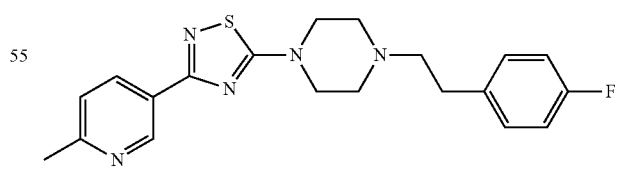

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-(5-Chloro-[1,2,4]thiadiazol-3-yl)-2-methyl-pyridine and 1-(4-fluorophenethyl)piperazine dihydrochloride as off-white solid. MS (m/e): 384.2 (MH⁺).

Example 97

1-[2-(2-Methoxy-pyridin-4-yl)-ethyl]-4-[3-(6-methyl-pyridin-3-yl)-[1,2,4]thiadiazol-5-yl]-piperazine

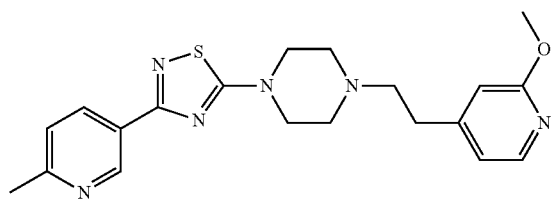 [SMILES: COc1cc(CCN2CCN(c3nc(-c4ccc(C)nc4)ns3)CC2)ccn1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-(5-Chloro-[1,2,4]thiadiazol-3-yl)-2-methylpyridine and 1-(2-(2-methoxypyridin-4-yl)ethyl)piperazine trihydrochloride as off-white solid. MS (m/e): 397.2 (MH+).

Example 98

1-[2-(4-Chloro-phenyl)-ethyl]-4-[3-(6-methyl-pyridin-3-yl)-[1,2,4]thiadiazol-5-yl]-piperazine

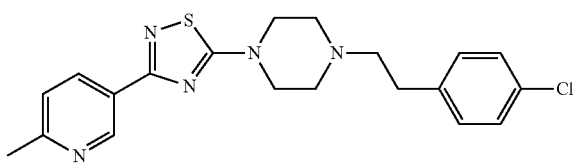 [SMILES: Cc1ccc(-c2nsc(N3CCN(CCc4ccc(Cl)cc4)CC3)n2)cn1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-(5-Chloro-[1,2,4]thiadiazol-3-yl)-2-methylpyridine and 1-(4-chlorophenethyl)piperazine dihydrochloride as off-white solid. MS (m/e): 400.1 (MH+).

Example 99

1-[3-(3-Fluoro-phenyl)-[1,2,4]thiadiazol-5-yl]-4-(2-methyl-benzyl)-piperazine

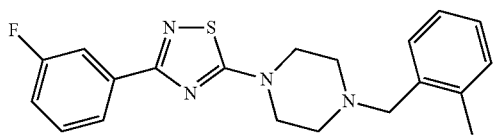 [SMILES: Cc1ccccc1CN1CCN(c2nc(-c3cccc(F)c3)ns2)CC1]

a) 1-[3-(3-Fluoro-phenyl)-[1,2,4]thiadiazol-5-yl]-piperazine dihydrochloride

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 5-chloro-3-(3-fluorophenyl)-1,2,4-thiadiazole and 1-BOC-piperazine with subsequent removal of the protecting group under acidic conditions as white solid. MS (m/e): 265.2 (MH+).

b) 1-[3-(3-Fluoro-phenyl)-[1,2,4]thiadiazol-5-yl]-4-(2-methyl-benzyl)-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Fluoro-phenyl)-[1,2,4]thiadiazol-5-yl]-piperazine dihydrochloride and 2-methylbenzyl chloride as colorless viscous oil. MS (m/e): 369.1 (MH+).

Example 100

1-[3-(3-Fluoro-phenyl)-[1,2,4]thiadiazol-5-yl]-4-[2-(6-methoxy-pyridin-3-yl)-ethyl]-piperazine

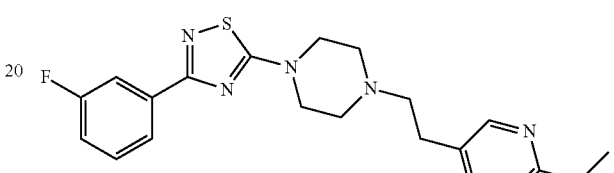

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Fluoro-phenyl)-[1,2,4]thiadiazol-5-yl]-piperazine dihydrochloride and 5-(2-bromoethyl)-2-methoxypyridine as light brown solid. MS (m/e): 400.1 (MH+).

Example 101

1-[3-(3,4-Difluoro-phenyl)-[1,2,4]thiadiazol-5-yl]-4-phenethyl-piperazine

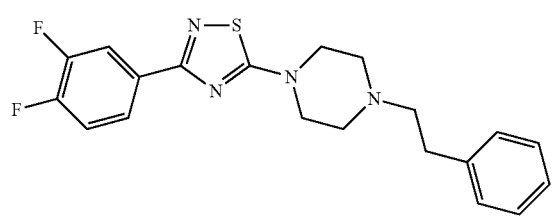 [SMILES: Fc1ccc(-c2nsc(N3CCN(CCc4ccccc4)CC3)n2)cc1F]

a) 1-[3-(3,4-Difluoro-phenyl)-[1,2,4]thiadiazol-5-yl]-piperazine dihydrochloride In analogy to the procedure described for the synthesis of tert-butyl 4-(3-bromo-1,2,4-thiadiazol-5-yl)piperazine-1-carboxylate (example 92, step a) the title compound was prepared from 1-[3-(3-Chloro-phenyl)-[1,2,4]thiadiazol-5-yl]-piperazine dihydrochloride and 3,4-difluorophenylboronic acid with subsequent removal of the protecting group under acidic conditions as light yellow solid. MS (m/e): 283.1 (MH+).

b) 1-[3-(3,4-Difluoro-phenyl)-[1,2,4]thiadiazol-5-yl]-4-phenethyl-piperazine

In analogy to the procedure described for the synthesis of 1-(2-Methyl-benzyl)-4-(3-p-tolyl-[1,2,4]thiadiazol-5-yl)- piperazine (example 6) the title compound was prepared from 1-[3-(3,4-Difluoro-phenyl)-[1,2,4]thiadiazol-5-yl]-piperazine dihydrochloride and (2-bromoethyl)benzene as off-white solid. MS (m/e): 387.2 (MH⁺).

Example 102

1-[3-(3,4-Difluoro-phenyl)-[1,2,4]thiadiazol-5-yl]-4-[2-(4-methoxy-phenyl)-ethyl]-piperazine

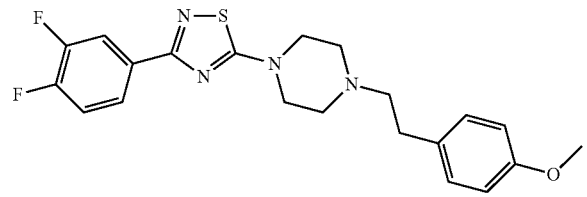 [SMILES: COc1ccc(CCN2CCN(c3nc(-c4ccc(F)c(F)c4)ns3)CC2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydrochloride and 1-(2-bromoethyl)-4-methoxybenzene as off-white solid. MS (m/e): 417.3 (MH⁺).

Example 103

1-[3-(3,4-Difluoro-phenyl)-[1,2,4]thiadiazol-5-yl]-4-[2-(4-fluoro-phenyl)-ethyl]-piperazine

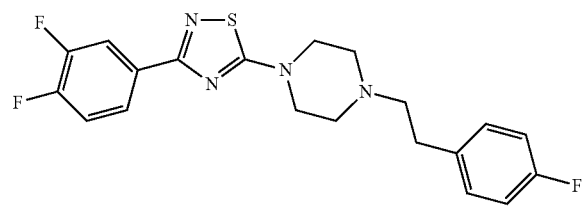 [SMILES: Fc1ccc(CCN2CCN(c3nc(-c4ccc(F)c(F)c4)ns3)CC2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydrochloride and 1-(2-bromoethyl)-4-fluorobenzene as off-white solid. MS (m/e): 405.3 (MH⁺).

Example 104

1-[2-(4-Chloro-phenyl)-ethyl]-4-[3-(3,4-difluoro-phenyl)-[1,2,4]thiadiazol-5-yl]-piperazine

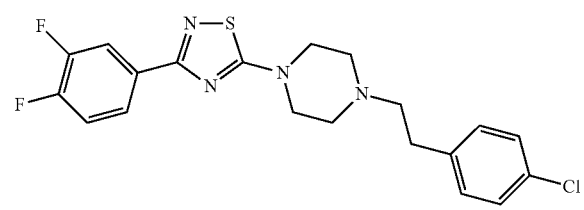 [SMILES: Fc1ccc(-c2nsc(N3CCN(CCc4ccc(Cl)cc4)CC3)n2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydrochloride and 1-(2-bromoethyl)-4-chlorobenzene as off-white solid. MS (m/e): 421.2 (MH⁺).

Example 105

1-[3-(3,4-Difluoro-phenyl)-[1,2,4]thiadiazol-5-yl]-4-[2-(6-methoxy-pyridin-3-yl)-ethyl]-piperazine

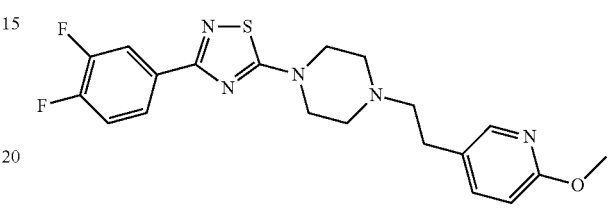

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydrochloride and 5-(2-bromoethyl)-2-methoxypyridine as off-white solid. MS (m/e): 418.3 (MH⁺).

Example 106

1-[3-(3,4-Difluoro-phenyl)-[1,2,4]thiadiazol-5-yl]-4-[2-(2-methoxy-pyridin-4-yl)-ethyl]-piperazine

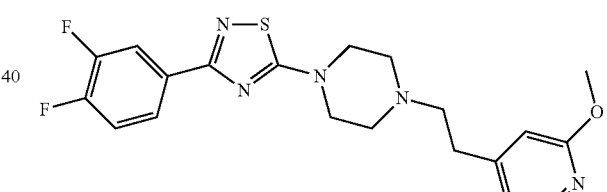

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydrochloride and 4-(2-bromoethyl)-2-methoxypyridine as off-white solid. MS (m/e): 418.2 (MH⁺).

Example 107

1-[3-(3,4-Difluoro-phenyl)-[1,2,4]thiadiazol-5-yl]-4-(2-methyl-benzyl)-piperazine

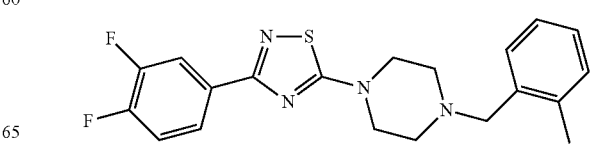

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydrochloride and 1-(chloromethyl)-2-methylbenzene as off-white solid. MS (m/e): 387.2 (MH⁺).

Example 108

4-[5-(4-Phenethyl-piperazin-1-yl)-[1,2,4]thiadiazol-3-yl]-benzonitrile

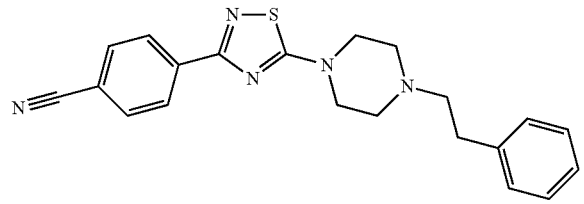 [SMILES: N#Cc1ccc(-c2nsc(N3CCN(CCc4ccccc4)CC3)n2)cc1]

a) 4-(5-Piperazin-1-yl-[1,2,4]thiadiazol-3-yl)-benzonitrile

In analogy to the procedure described for the synthesis of tert-butyl 4-(3-bromo-1,2,4-thiadiazol-5-yl)piperazine-1-carboxylate (example 92, step a) the title compound was prepared from 1-[3-(3-Chloro-phenyl)-[1,2,4]thiadiazol-5-yl]-piperazine dihydrochloride and 4-cyanophenylboronic acid with subsequent removal of the protecting group under acidic conditions as light yellow solid. MS (m/e): 272.1 (MH⁺).

b) 1-[3-(3,4-Difluoro-phenyl)-[1,2,4]thiadiazol-5-yl]-4-phenethyl-piperazine

In analogy to the procedure described for the synthesis of 1-(2-Methyl-benzyl)-4-(3-p-tolyl-[1,2,4]thiadiazol-5-yl)-piperazine (example 6) the title compound was prepared from 1-[4-cyano-phenyl)-[1,2,4]thiadiazol-5-yl]-piperazine dihydrochloride and (2-bromoethyl)benzene as off-white solid. MS (m/e): 376.3 (MH⁺).

Example 109

3-[5-(4-Phenethyl-piperazin-1-yl)-[1,2,4]thiadiazol-3-yl]-benzonitrile

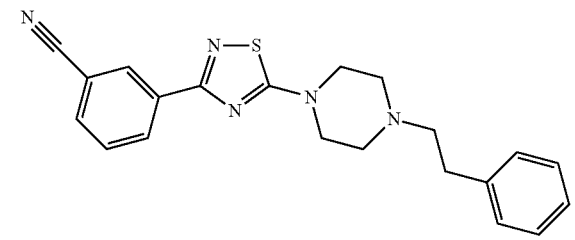 [SMILES: N#Cc1cccc(-c2nsc(N3CCN(CCc4ccccc4)CC3)n2)c1]

a) 3-(5-Piperazin-1-yl-[1,2,4]thiadiazol-3-yl)-benzonitrile

In analogy to the procedure described for the synthesis of tert-butyl 4-(3-bromo-1,2,4-thiadiazol-5-yl)piperazine-1-carboxylate (example 92, step a) the title compound was prepared from 1-[3-(3-Chloro-phenyl)-[1,2,4]thiadiazol-5-yl]-piperazine dihydrochloride and 3-cyanophenylboronic acid with subsequent removal of the protecting group under acidic conditions as light yellow solid. MS (m/e): 272.1 (MH⁺).

b) 1-[3-(3,4-Difluoro-phenyl)-[1,2,4]thiadiazol-5-yl]-4-phenethyl-piperazine

In analogy to the procedure described for the synthesis of 1-(2-Methyl-benzyl)-4-(3-p-tolyl-[1,2,4]thiadiazol-5-yl)-piperazine (example 6) the title compound was prepared from 1-[(3-cyano-phenyl)-[1,2,4]thiadiazol-5-yl]-piperazine dihydrochloride and (2-bromoethyl)benzene as light brown solid. MS (m/e): 376.3 (MH⁺).

Example 110

4-(5-{4-[2-(4-Fluoro-phenyl)-ethyl]piperazin-1-yl}-[1,2,4]thiadiazol-3-yl)-benzonitrile

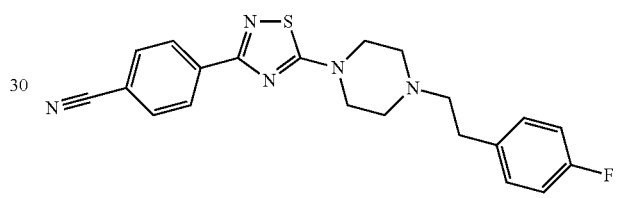

In analogy to the procedure described for the synthesis of 1-(2-Methyl-benzyl)-4-(3-p-tolyl-[1,2,4]thiadiazol-5-yl)-piperazine (example 6) the title compound was prepared from 1-[4-cyano-phenyl)-[1,2,4]thiadiazol-5-yl]-piperazine dihydrochloride and 1-(2-bromoethyl)-4-fluorobenzene as off-white solid. MS (m/e): 394.1 (MH⁺).

Example 111

3-(5-{4-[2-(4-Fluoro-phenyl)-ethyl]piperazin-1-yl}-[1,2,4]thiadiazol-3-yl)-benzonitrile

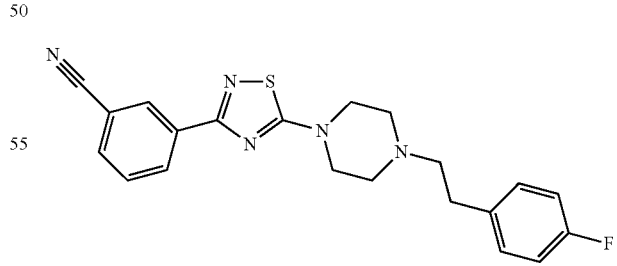

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-cyano-phenyl)-[1,2,4]thiadiazol-5-yl]-piperazine dihydrochloride and 1-(2-bromoethyl)-4-fluorobenzene as light brown solid. MS (m/e): 394.1 (MH⁺).

Example 112

4-(5-{4-[2-(4-Chloro-phenyl)-ethyl]piperazin-1-yl}-[1,2,4]thiadiazol-3-yl)-benzonitrile

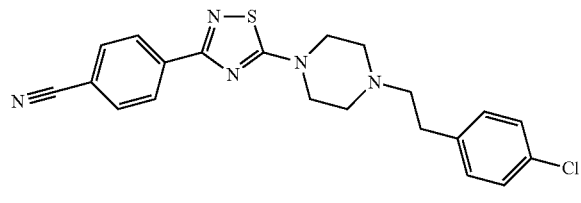 [SMILES: N#Cc1ccc(-c2nsc(N3CCN(CCc4ccc(Cl)cc4)CC3)n2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[4-cyano-phenyl)-[1,2,4]thiadiazol-5-yl]-piperazine dihydrochloride and 1-(2-bromoethyl)-4-chlorobenzene as off-white solid. MS (m/e): 410.2 (MH+).

Example 113

3-(5-{4-[2-(4-Chloro-phenyl)-ethyl]piperazin-1-yl}-[1,2,4]thiadiazol-3-yl)-benzonitrile

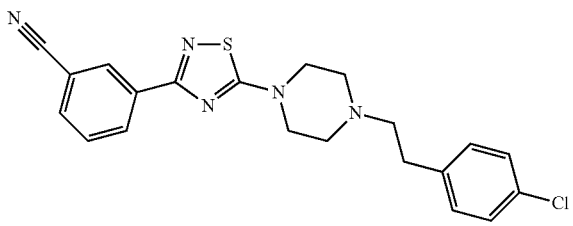 [SMILES: N#Cc1cccc(-c2nsc(N3CCN(CCc4ccc(Cl)cc4)CC3)n2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-cyano-phenyl)-[1,2,4]thiadiazol-5-yl]-piperazine dihydrochloride and 1-(2-bromoethyl)-4-chlorobenzene as light brown solid. MS (m/e): 410.2 (MH+).

Example 114

4-(5-{4-[2-(6-Methoxy-pyridin-3-yl)-ethyl]-piperazin-1-yl}-[1,2,4]thiadiazol-3-yl)-benzonitrile

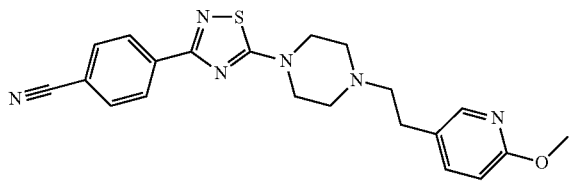 [SMILES: COc1ccc(CCN2CCN(c3nc(-c4ccc(C#N)cc4)ns3)CC2)cn1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[4-cyano-phenyl)-[1,2,4]thiadiazol-5-yl]-piperazine dihydrochloride and 5-(2-bromoethyl)-2-methoxypyridine as off-white solid. MS (m/e): 407.3 (MH+).

Example 115

3-(5-{4-[2-(6-Methoxy-pyridin-3-yl)-ethyl]-piperazin-1-yl}-[1,2,4]thiadiazol-3-yl)-benzonitrile

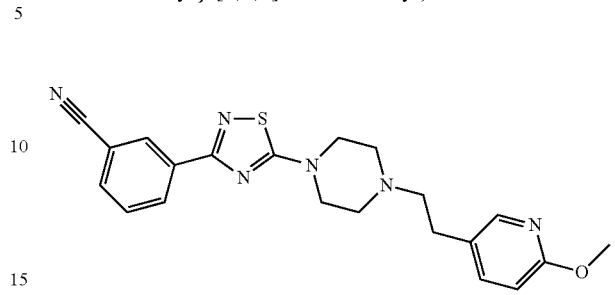

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-cyano-phenyl)-[1,2,4]thiadiazol-5-yl]-piperazine dihydrochloride and 5-(2-bromoethyl)-2-methoxypyridine as light brown solid. MS (m/e): 407.4 (MH+).

Example 116

4-(5-{4-[2-(2-Methoxy-pyridin-4-yl)-ethyl]-piperazin-1-yl}-[1,2,4]thiadiazol-3-yl)-benzonitrile

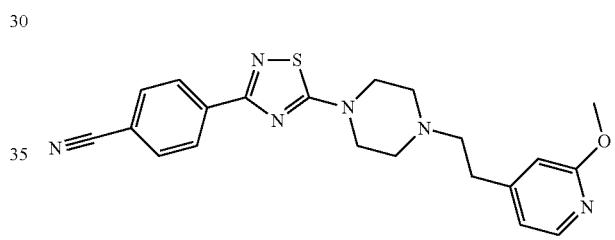

In analogy to the procedure described for the synthesis of 1-(2-Methyl-benzyl)-4-(3-p-tolyl-[1,2,4]thiadiazol-5-yl)-piperazine (example 6) the title compound was prepared from 1-[4-cyano-phenyl)-[1,2,4]thiadiazol-5-yl]-piperazine dihydrochloride and 4-(2-bromoethyl)-2-methoxypyridine as off-white solid. MS (m/e): 407.3 (MH+).

Example 117

3-(5-{4-[2-(2-Methoxy-pyridin-4-yl)-ethyl]-piperazin-1-yl}-[1,2,4]thiadiazol-3-yl)-benzonitrile

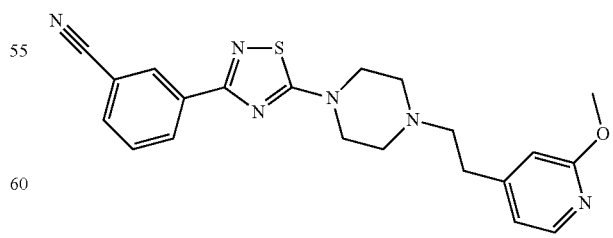

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-cyano-phenyl)-[1,2,4]thiadiazol-5-yl]-piperazine dihydrochloride and 4-(2-bromoethyl)-2-methoxypyridine as light brown solid. MS (m/e): 407.4 (MH⁺).

Example 118

4-{5-[4-(2-Methyl-benzyl)-piperazin-1-yl]-[1,2,4]thiadiazol-3-yl}-benzonitrile

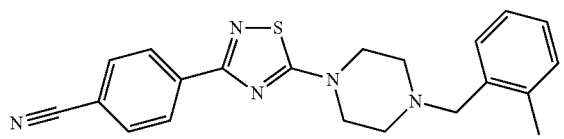 [SMILES: Cc1ccccc1CN1CCN(c2nc(-c3ccc(C#N)cc3)ns2)CC1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[4-cyano-phenyl)-[1,2,4]thiadiazol-5-yl]-piperazine dihydrochloride and 1-(chloromethyl)-2-methylbenzene as off-white solid. MS (m/e): 376.3 (MH⁺).

Example 119

3-{5-[4-(2-Methyl-benzyl)-piperazin-1-yl]-[1,2,4]thiadiazol-3-yl}-benzonitrile

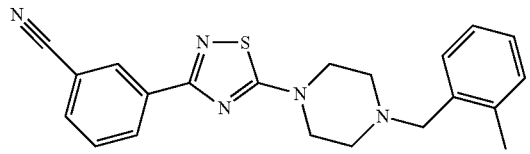 [SMILES: Cc1ccccc1CN1CCN(c2nc(-c3cccc(C#N)c3)ns2)CC1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-cyano-phenyl)-[1,2,4]thiadiazol-5-yl]-piperazine dihydrochloride and 1-(chloromethyl)-2-methylbenzene as light brown solid. MS (m/e): 376.3 (MH⁺).

Example 120

1-[3-(4-Chloro-pyridin-2-yl)-[1,2,4]thiadiazol-5-yl]-4-phenethyl-piperazine

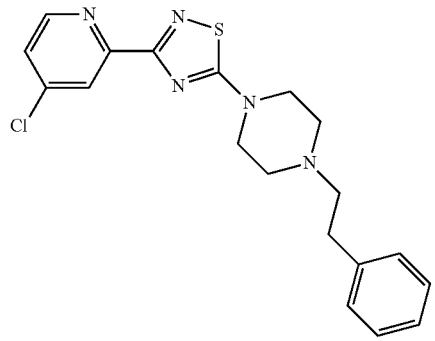 [SMILES: Clc1ccnc(-c2nsc(N3CCN(CCc4ccccc4)CC3)n2)c1]

a) 4-Chloro-2-(5-chloro-[1,2,4]thiadiazol-3-yl)-pyridine

In analogy to the procedure described fort the synthesis of 4-(5-Chloro-[1,2,4]thiadiazol-3-yl)-pyridine (example 20, step a) the title compound was prepared from 4-chloropicolinimidamide hydrochloride and perchloromethyl mecaptan as brown solid. MS (m/e): 232.0 (MH⁺).

b) 1-[3-(4-Chloro-pyridin-2-yl)-[1,2,4]thiadiazol-5-yl]-4-phenethyl-piperazine

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 1-phenethylpiperazine dihydrochloride. MS (m/e): 386.2 (MH⁺).

Example 121

1-[3-(5-Chloro-pyridin-2-yl)-[1,2,4]thiadiazol-5-yl]-4-phenethyl-piperazine

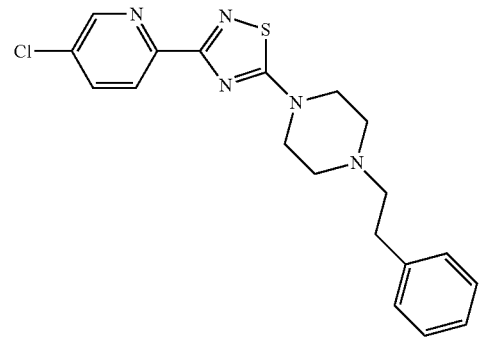 [SMILES: Clc1ccc(-c2nsc(N3CCN(CCc4ccccc4)CC3)n2)nc1]

a) 5-Chloro-2-(5-chloro-[1,2,4]thiadiazol-3-yl)-pyridine

In analogy to the procedure described for the synthesis of 4-(5-Chloro-[1,2,4]thiadiazol-3-yl)-pyridine (example 20, step a) the title compound was prepared from 5-chloropicolinimidamide hydrochloride and perchloromethyl mecaptan as brown solid. MS (m/e): 232.0 (MH⁺).

b) 1-[3-(5-Chloro-pyridin-2-yl)-[1,2,4]thiadiazol-5-yl]-4-phenethyl-piperazine

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-2-(5-chloro-[1,2,4]thiadiazol-3-yl)-pyridine and 1-phenethylpiperazine dihydrochloride. MS (m/e): 386.2 (MH⁺).

Example 122

1-[3-(4-Chloro-pyridin-2-yl)-[1,2,4]thiadiazol-5-yl]-4-[2-(4-fluoro-phenyl)-ethyl]-piperazine

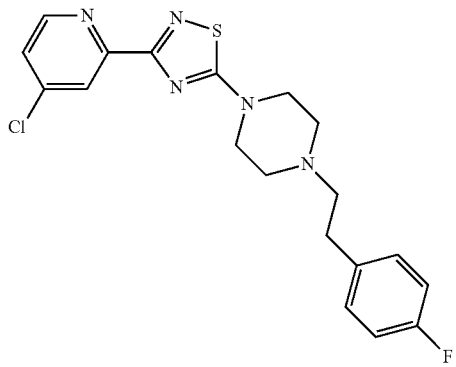 [SMILES: Fc1ccc(CCN2CCN(c3nc(-c4cc(Cl)ccn4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 1-(4-fluorophenethyl)piperazine dihydrochloride. MS (m/e): 404.3 (MH$^+$).

Example 123

1-[2-(4-Chloro-phenyl)-ethyl]-4-[3-(4-chloro-pyridin-2-yl)-[1,2,4]thiadiazol-5-yl]-piperazine

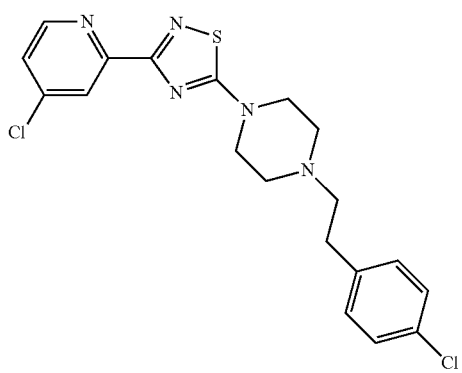 [SMILES: Clc1ccc(CCN2CCN(c3nc(-c4cc(Cl)ccn4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 1-(4-chlorophenethyl)piperazine dihydrochloride. MS (m/e): 420.1 (MH$^+$).

Example 124

1-[2-(4-Chloro-phenyl)-ethyl]-4-[3-(5-chloro-pyridin-2-yl)-[1,2,4]thiadiazol-5-yl]-piperazine

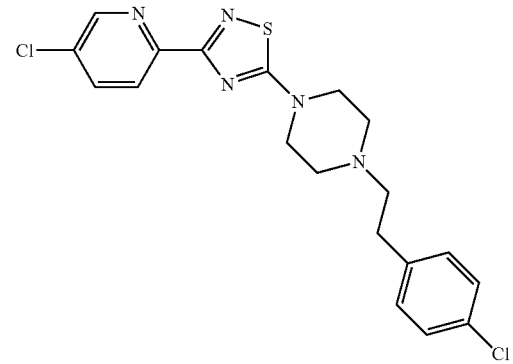 [SMILES: Clc1ccc(CCN2CCN(c3nc(-c4ccc(Cl)cn4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-2-(5-chloro-[1,2,4]thiadiazol-3-yl)-pyridine and 1-(4-chlorophenethyl)piperazine dihydrochloride. MS (m/e): 420.1 (MH$^+$).

Example 125

1-[3-(4-Chloro-pyridin-2-yl)-[1,2,4]thiadiazol-5-yl]-4-[2-(4-methoxy-phenyl)-ethyl]-piperazine

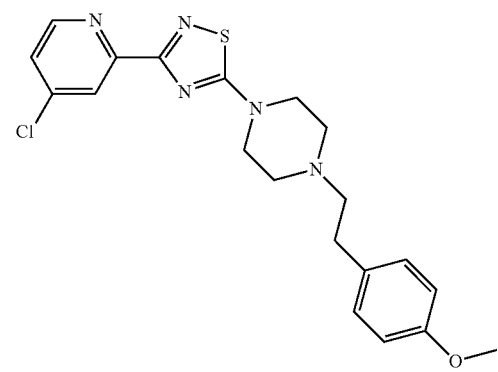 [SMILES: COc1ccc(CCN2CCN(c3nc(-c4cc(Cl)ccn4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 1-(4-methoxyphenethyl)piperazine dihydrochloride. MS (m/e): 416.3 (MH$^+$).

Example 126

1-[3-(5-Chloro-pyridin-2-yl)-[1,2,4]thiadiazol-5-yl]-4-[2-(4-methoxy-phenyl)-ethyl]-piperazine

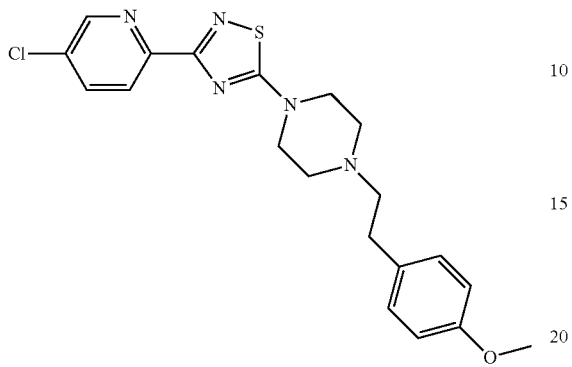

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-Chloro-2-(5-chloro-[1,2,4]thiadiazol-3-yl)-pyridine and 1-(4-methoxyphenethyl)piperazine dihydrochloride. MS (m/e): 416.3 (MH$^+$).

Example 127

1-[3-(4-Chloro-pyridin-2-yl)-[1,2,4]thiadiazol-5-yl]-4-[2-(2-methoxy-pyridin-4-yl)-ethyl]-piperazine

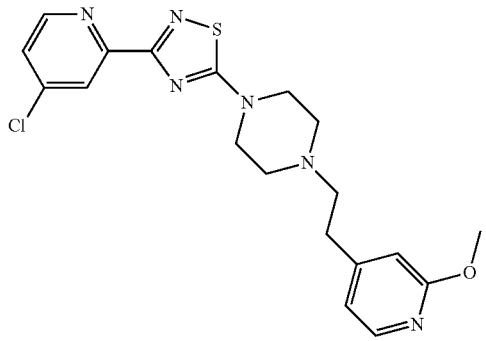 [SMILES: COc1cc(CCN2CCN(c3nc(-c4cc(Cl)ccn4)ns3)CC2)ccn1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 1-(2-(2-methoxypyridin-4-yl)ethyl)piperazine trihydrochloride. MS (m/e): 417.3 (MH$^+$).

Example 128

1-[3-(4-Chloro-pyridin-2-yl)-[1,2,4]thiadiazol-5-yl]-4-(2-methyl-benzyl)-piperazine

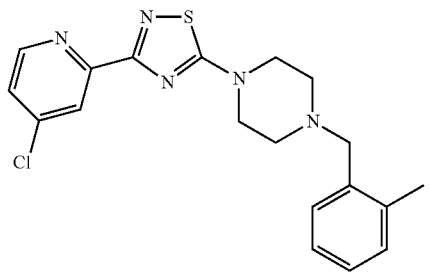 [SMILES: Cc1ccccc1CN1CCN(c2nc(-c3cc(Cl)ccn3)ns2)CC1]

a) 1-[3-(4-Chloro-pyridin-2-yl)-[1,2,4]thiadiazol-5-yl]-piperazine

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 4-Chloro-2-(5-chloro-[1,2,4]thiadiazol-3-yl)-pyridine and 1-BOC-piperazine with subsequent removal of the protecting group under acidic conditions as white solid. MS (m/e): 265.2 (MH$^+$).

b) 1-[3-(4-Chloro-pyridin-2-yl)-[1,2,4]thiadiazol-5-yl]-4-(2-methyl-benzyl)-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-pyridin-2-yl)-[1,2,4]thiadiazol-5-yl]-piperazine and 1-(chloromethyl)-2-methylbenzene. MS (m/e): 386.2 (MH$^+$).

Example 129

1-[3-(5-Chloro-pyridin-2-yl)-[1,2,4]thiadiazol-5-yl]-4-(2-methyl-benzyl)-piperazine

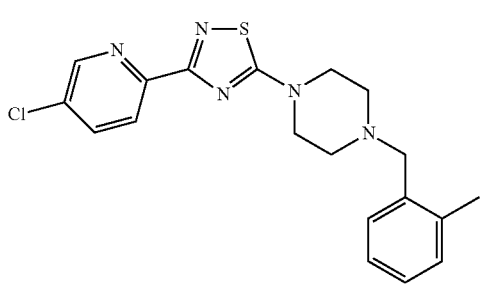 [SMILES: Cc1ccccc1CN1CCN(c2nc(-c3ccc(Cl)cn3)ns2)CC1]

a) 1-[3-(5-Chloro-pyridin-2-yl)-[1,2,4]thiadiazol-5-yl]-piperazine

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 5-Chloro-2-(5-chloro-[1,2,4]thiadiazol- 3-yl)-pyridine and 1-BOC-piperazine with subsequent removal of the protecting group under acidic conditions as light brown solid. MS (m/e): 282.2 (MH+).

b) 1-[3-(5-Chloro-pyridin-2-yl)-[1,2,4]thiadiazol-5-yl]-4-(2-methyl-benzyl)-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(5-Chloro-pyridin-2-yl)-[1,2,4]thiadiazol-5-yl]-piperazine and 1-(chloromethyl)-2-methylbenzene. MS (m/e): 386.2 (MH+).

Example 130

1-[3-(5-Chloro-pyridin-3-yl)-[1,2,4]thiadiazol-5-yl]-4-phenethyl-piperazine

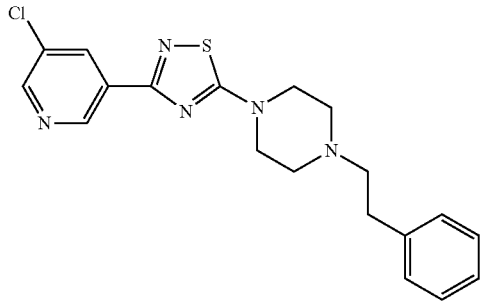 [SMILES: Clc1cncc(-c2nsc(N3CCN(CCc4ccccc4)CC3)n2)c1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 3-Chloro-5-(5-chloro-[1,2,4]thiadiazol-3-yl)-pyridine and 1-phenethylpiperazine dihydrochloride as white solid. MS (m/e): 386.2 (MH+).

Example 131

1-[3-(5-Chloro-pyridin-3-yl)-[1,2,4]thiadiazol-5-yl]-4-[2-(4-fluoro-phenyl)-ethyl]-piperazine

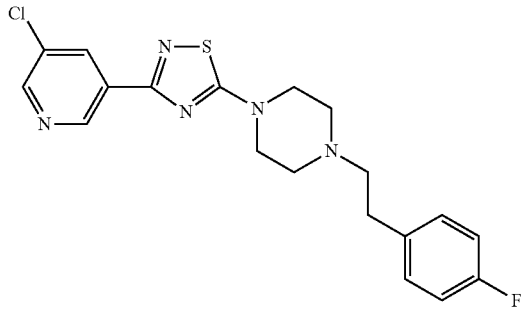 [SMILES: Fc1ccc(CCN2CCN(c3nc(-c4cncc(Cl)c4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 3-Chloro-5-(5-chloro-[1,2,4]thiadiazol-3-yl)-pyridine and 1-(4-fluorophenethyl)piperazine dihydrochloride as white solid. MS (m/e): 404.3 (MH+).

Example 132

1-[2-(4-Chloro-phenyl)-ethyl]-4-[3-(5-chloro-pyridin-3-yl)-[1,2,4]thiadiazol-5-yl]-piperazine

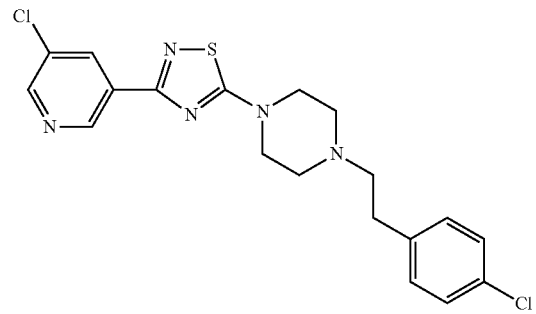 [SMILES: Clc1ccc(CCN2CCN(c3nc(-c4cncc(Cl)c4)ns3)CC2)cc1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 3-Chloro-5-(5-chloro-[1,2,4]thiadiazol-3-yl)-pyridine and 1-(4-chlorophenethyl)piperazine dihydrochloride as white solid. MS (m/e): 420.1 (MH+).

Example 133

1-[3-(5-Chloro-pyridin-3-yl)-[1,2,4]thiadiazol-5-yl]-4-[2-(2-methoxy-pyridin-4-yl)-ethyl]-piperazine

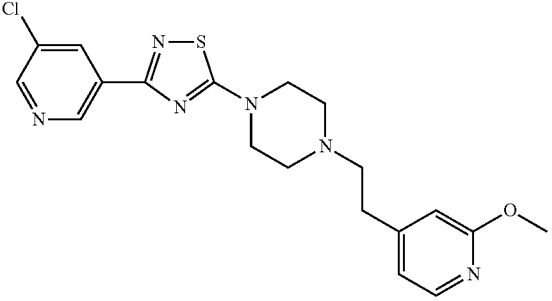 [SMILES: COc1cc(CCN2CCN(c3nc(-c4cncc(Cl)c4)ns3)CC2)ccn1]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 3-Chloro-5-(5-chloro-[1,2,4]thiadiazol-3-yl)-pyridine and 1-(2-(2-methoxypyridin-4-yl)ethyl)piperazine trihydrochloride as viscous colorless oil. MS (m/e): 417.2 (MH+).

Example 134

1-[3-(4-Chloro-phenyl)-[1,2,4]thiadiazol-5-yl]-4-[2-(3,4-difluoro-phenyl)-ethyl]-piperazine

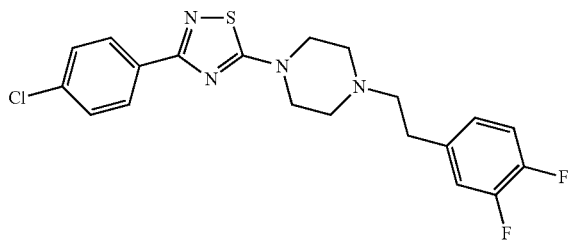 [SMILES: Fc1ccc(CCN2CCN(c3nc(-c4ccc(Cl)cc4)ns3)CC2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 4-(2-bromo ethyl)-1,2-difluorobenzene. MS (m/e): 421.1 (MH$^+$).

Example 135

1-[3-(3-Chloro-phenyl)-[1,2,4]thiadiazol-5-yl]-4-[2-(3,4-difluoro-phenyl)-ethyl]-piperazine

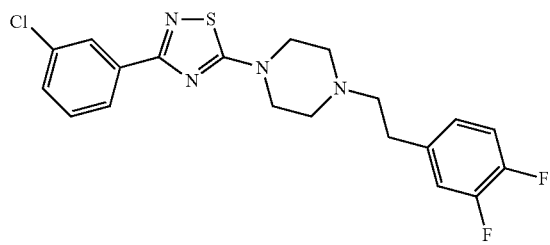 [SMILES: Fc1ccc(CCN2CCN(c3nc(-c4cccc(Cl)c4)ns3)CC2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Chloro-phenyl)-[1,2,4]thiadiazol-5-yl]-piperazine and 4-(2-bromoethyl)-1,2-difluorobenzene. MS (m/e): 421.1 (MH$^+$).

Example 136

1-[2-(3,4-Difluoro-phenyl)-ethyl]-4-[3-(3,4-difluoro-phenyl)-[1,2,4]thiadiazol-5-yl]-piperazine

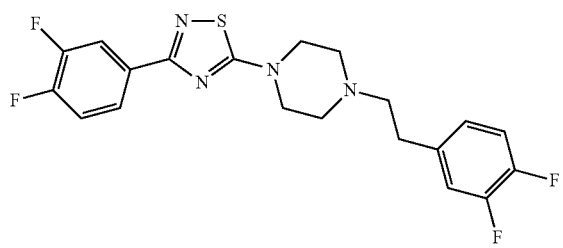 [SMILES: Fc1ccc(CCN2CCN(c3nc(-c4ccc(F)c(F)c4)ns3)CC2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(3,4-difluorophenyl)-5-(piperazin-1-yl)-1,2,4-thiadiazole dihydrochloride and 4-(2-bromoethyl)-1,2-difluorobenzene. MS (m/e): 423.2 (MH$^+$).

Example 137

3-(5-{4-[2-(3,4-Difluoro-phenyl)-ethyl]-piperazin-1-yl}-[1,2,4]thiadiazol-3-yl)-benzonitrile

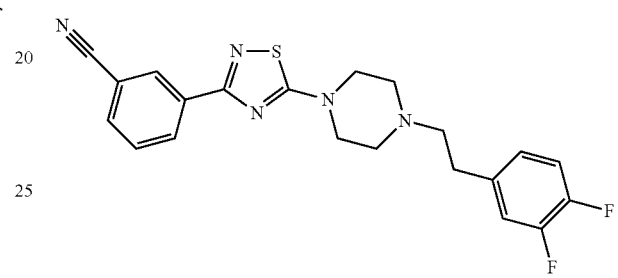

In analogy to the procedure described for the synthesis of 1-(2-Methyl-benzyl)-4-(3-p-tolyl-[1,2,4]thiadiazol-5-yl)-piperazine (example 6) the title compound was prepared from 3-(5-(piperazin-1-yl)-1,2,4-thiadiazol-3-yl)benzonitrile and 4-(2-bromo ethyl)-1,2-difluorobenzene. MS (m/e): 412.2 (MH$^+$).

Example 138

4-(5-{4-[2-(3,4-Difluoro-phenyl)-ethyl]piperazin-1-yl}-[1,2,4]thiadiazol-3-yl)-benzonitrile

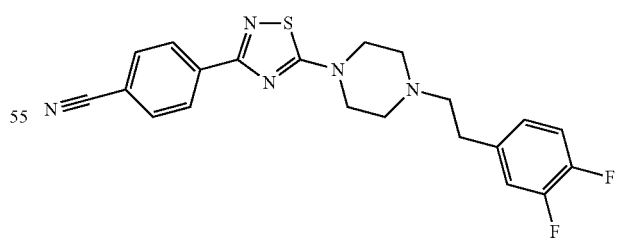

In analogy to the procedure described for the synthesis of 1-(2-Methyl-benzyl)-4-(3-p-tolyl-[1,2,4]thiadiazol-5-yl)-piperazine (example 6) the title compound was prepared from 4-(5-(piperazin-1-yl)-1,2,4-thiadiazol-3-yl)benzonitrile and 4-(2-bromoethyl)-1,2-difluorobenzene. MS (m/e): 412.2 (MH$^+$).

Example 139

1-[3-(5-Chloro-pyridin-2-yl)-[1,2,4]thiadiazol-5-yl]-4-[2-(3,4-difluoro-phenyl)-ethyl]-piperazine

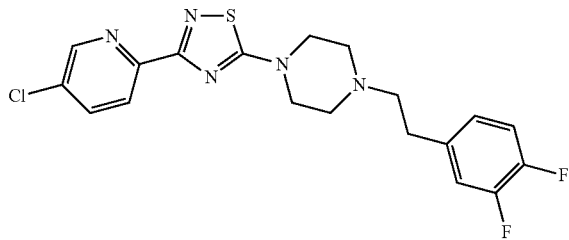 [SMILES: Fc1ccc(CCN2CCN(c3nc(-c4ccc(Cl)cn4)ns3)CC2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(5-chloropyridin-2-yl)-5-(piperazin-1-yl)-1,2,4-thiadiazole and 4-(2-bromoethyl)-1,2-difluorobenzene. MS (m/e): 422.1 (MH$^+$).

Example 140

1-[3-(4-Chloro-phenyl)-[1,2,4]thiadiazol-5-yl]-4-[2-(3-trifluoromethyl-phenyl)-ethyl]-piperazine

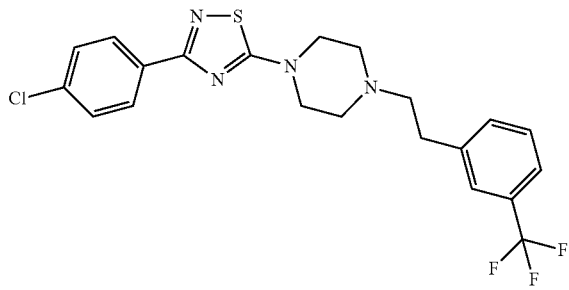 [SMILES: FC(F)(F)c1cccc(CCN2CCN(c3nc(-c4ccc(Cl)cc4)ns3)CC2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-3-(trifluoromethyl)benzene. MS (m/e): 453.1 (MH$^+$).

Example 141

1-[3-(3-Fluoro-phenyl)-[1,2,4]thiadiazol-5-yl]-4-[2-(3-trifluoromethyl-phenyl)-ethyl]-piperazine

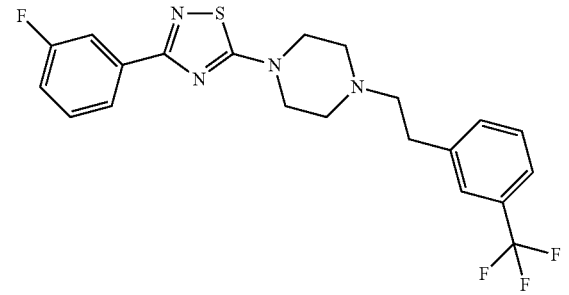 [SMILES: Fc1cccc(-c2nsc(N3CCN(CCc4cccc(C(F)(F)F)c4)CC3)n2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Fluoro-phenyl)-[1,2,4]thiadiazol-5-yl]-piperazine dihydro chloride and 1-(2-bromoethyl)-3-(trifluoromethyl)benzene. MS (m/e): 437.2 (MH$^+$).

Example 142

1-[3-(3-Chloro-phenyl)-[1,2,4]thiadiazol-5-yl]-4-[2-(3-trifluoromethyl-phenyl)-ethyl]-piperazine

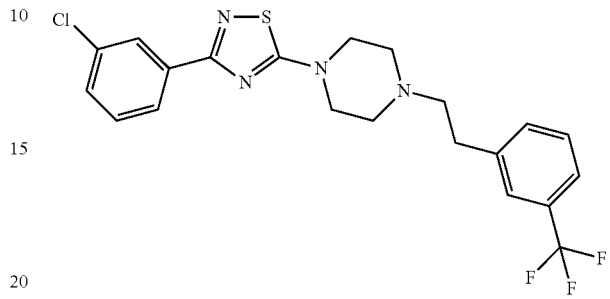

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Chloro-phenyl)-[1,2,4]thiadiazol-5-yl]-piperazine and 1-(2-bromo ethyl)-3-(trifluoromethyl)benzene. MS (m/e): 453.1 (MH$^+$).

Example 143

4-(5-{4-[2-(3-Trifluoromethyl-phenyl)-ethyl]-piperazin-1-yl}-[1,2,4]thiadiazol-3-yl)-benzonitrile

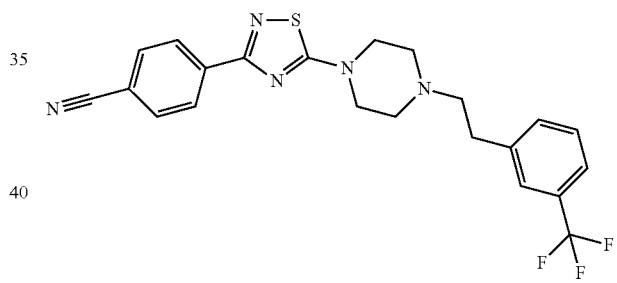

In analogy to the procedure described for the synthesis of 1-(2-Methyl-benzyl)-4-(3-p-tolyl-[1,2,4]thiadiazol-5-yl)-piperazine (example 6) the title compound was prepared from 3-(5-(piperazin-1-yl)-1,2,4-thiadiazol-3-yl)benzonitrile and 1-(2-bromoethyl)-3-(trifluoromethyl)benzene. MS (m/e): 444.3 (MH$^+$).

Example 144

1-[3-(4-Chloro-phenyl)-[1,2,4]thiadiazol-5-yl]-4-[2-(4-trifluoromethyl-phenyl)-ethyl]-piperazine

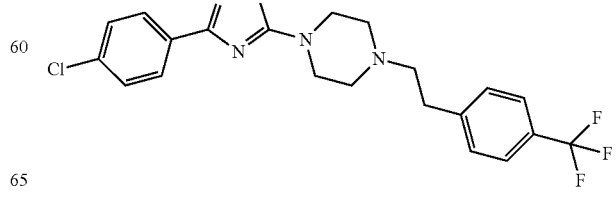

In analogy to the procedure described for the synthesis of 1-(2-Methyl-benzyl)-4-(3-p-tolyl-[1,2,4]thiadiazol-5-yl)-

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(4-Chloro-phenyl)-[1,2,4]thiadiazol-5-yl]-piperazine and 1-(2-bromoethyl)-4-(trifluoromethyl)benzene. MS (m/e): 453.1 (MH⁺).

Example 145

1-[3-(3-Chloro-phenyl)-[1,2,4]thiadiazol-5-yl]-4-[2-(4-trifluoromethyl-phenyl)-ethyl]-piperazine

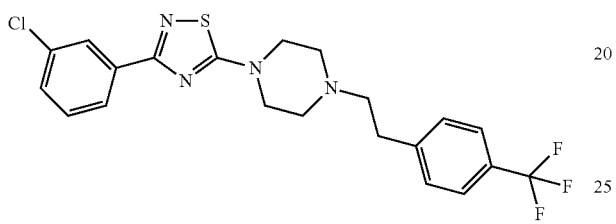

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Chloro-phenyl)-[1,2,4]thiadiazol-5-yl]-piperazine and 1-(2-bromoethyl)-4-(trifluoromethyl)benzene. MS (m/e): 453.1 (MH⁺).

Example 146

1-[3-(3,4-Difluoro-phenyl)-[1,2,4]thiadiazol-5-yl]-4-[2-(4-trifluoromethyl-phenyl)-ethyl]-piperazine

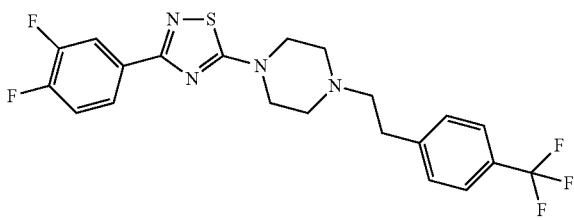 [SMILES: Fc1ccc(-c2nsc(N3CCN(CCc4ccc(C(F)(F)F)cc4)CC3)n2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(3,4-difluorophenyl)-5-(piperazin-1-yl)-1,2,4-thiadiazole dihydrochloride and 1-(2-bromoethyl)-4-(trifluoromethyl)benzene. MS (m/e): 455.2 (MH⁺).

Example 147

4-(5-{4-[2-(4-Trifluoromethyl-phenyl)-ethyl]-piperazin-1-yl}-[1,2,4]thiadiazol-3-yl)-benzonitrile

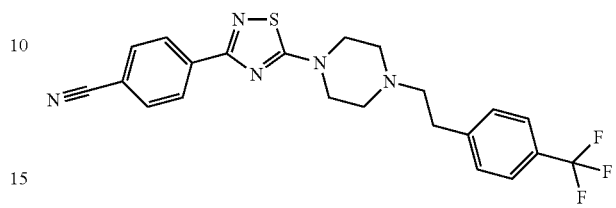

In analogy to the procedure described for the synthesis of 1-(2-Methyl-benzyl)-4-(3-p-tolyl-[1,2,4]thiadiazol-5-yl)-piperazine (example 6) the title compound was prepared from 3-(5-(piperazin-1-yl)-1,2,4-thiadiazol-3-yl)benzonitrile and 1-(2-bromoethyl)-4-(trifluoromethyl)benzene. MS (m/e): 444.3 (MH⁺).

Example 148

1-[2-(3,4-Difluoro-phenyl)-ethyl]-4-[3-(6-methyl-pyridin-3-yl)-[1,2,4]thiadiazol-5-yl]-piperazine

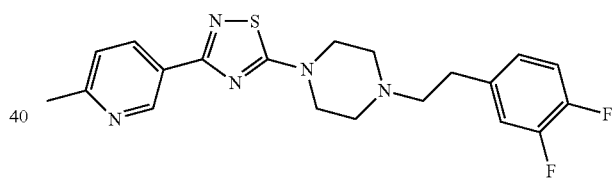

a) 1-[3-(6-Methyl-pyridin-3-yl)-[1,2,4]thiadiazol-5-yl]-piperazine

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 5-(5-Chloro-[1,2,4]thiadiazol-3-yl)-2-methyl-pyridine and 1-BOC-piperazine with subsequent removal of the protecting group under acidic conditions as off-white solid. MS (m/e): 262.1 (MH⁺).

b) 1-[2-(3,4-Difluoro-phenyl)-ethyl]-4-[3-(6-methyl-pyridin-3-yl)-[1,2,4]thiadiazol-5-yl]-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 3-(6-methylpyridin-3-yl)-5-(piperazin-1-yl)-1,2,4-thiadiazole and 4-(2-bromoethyl)-1,2-difluorobenzene. MS (m/e): 402.3 (MH⁺).

Example 149

1-[3-(5-Chloro-pyridin-3-yl)-[1,2,4]thiadiazol-5-yl]-4-[2-(3-trifluoromethyl-phenyl)-ethyl]-piperazine

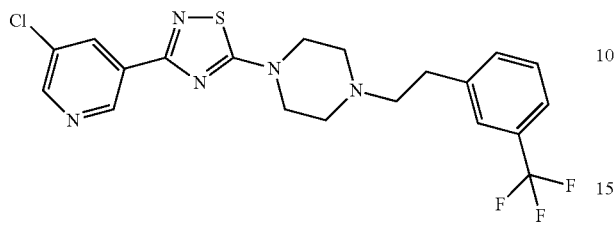

a) 1-[3-(5-Chloro-pyridin-3-yl)-[1,2,4]thiadiazol-5-yl]-piperazine

In analogy to the procedure described for the synthesis of 1-[2-(3-Methoxy-phenyl)-ethyl]-4-(3-pyridin-4-yl-[1,2,4]thiadiazol-5-yl)-piperazine (Example 20) the title compound was prepared from 3-Chloro-5-(5-chloro-[1,2,4]thiadiazol-3-yl)-pyridine and 1-BOC-piperazine with subsequent removal of the protecting group under acidic conditions as white solid. MS (m/e): 282.2 (MH$^+$).

b) 1-[3-(5-Chloro-pyridin-3-yl)-[1,2,4]thiadiazol-5-yl]-4-[2-(3-trifluoromethyl-phenyl)-ethyl]-piperazine In analogy to the procedure described for the synthesis of 1-(2-Methyl-benzyl)-4-(3-p-tolyl-[1,2,4]thiadiazol-5-yl)-piperazine (example 6) the title compound was prepared from 3-(6-methylpyridin-3-yl)-5-(piperazin-1-yl)-1,2,4-thiadiazole and 1-(2-bromoethyl)-3-(trifluoromethyl)benzene. MS (m/e): 454.1 (MH$^+$).

Example 150

1-(2-Methyl-benzyl)-4-[3-(6-methyl-pyridin-3-yl)-[1,2,4]thiadiazol-5-yl]-piperazine

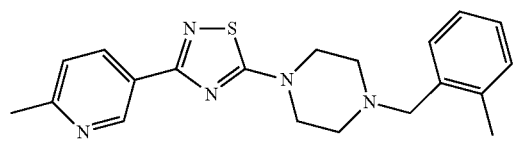 [SMILES: Cc1ccc(-c2nsc(N3CCN(Cc4ccccc4C)CC3)n2)cn1]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(6-methylpyridin-3-yl)-5-(piperazin-1-yl)-1,2,4-thiadiazole and 1-(chloromethyl)-2-methylbenzene. MS (m/e): 366.2 (MH$^+$).

Example 151

1-[3-(5-Chloro-pyridin-3-yl)-[1,2,4]thiadiazol-5-yl]-4-(2-methyl-benzyl)-piperazine

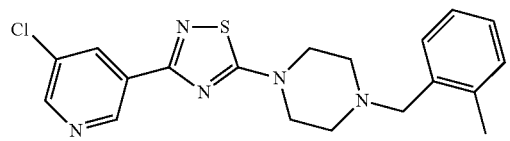 [SMILES: Cc1ccccc1CN1CCN(c2nc(-c3cncc(Cl)c3)ns2)CC1]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(6-methylpyridin-3-yl)-5-(piperazin-1-yl)-1,2,4-thiadiazole and 1-(chloromethyl)-2-methylbenzene. MS (m/e): 386.2 (MH$^+$).

Example 152

1-[3-(5-Chloro-pyridin-3-yl)-[1,2,4]thiadiazol-5-yl]-4-[2-(4-trifluoromethyl-phenyl)-ethyl]-piperazine

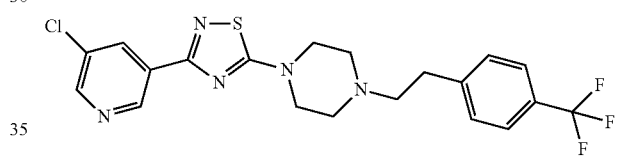

In analogy to the procedure described for the synthesis of 1-(2-Methyl-benzyl)-4-(3-p-tolyl-[1,2,4]thiadiazol-5-yl)-piperazine (example 6) the title compound was prepared from 3-(6-methylpyridin-3-yl)-5-(piperazin-1-yl)-1,2,4-thiadiazole and 1-(2-bromoethyl)-4-(trifluoromethyl)benzene. MS (m/e): 454.1 (MH$^+$).

Examples 153

1-(2-Cyclohexyl-ethyl)-4-[3-(3,4-difluoro-phenyl)-[1,2,4]thiadiazol-5-yl]-piperazine

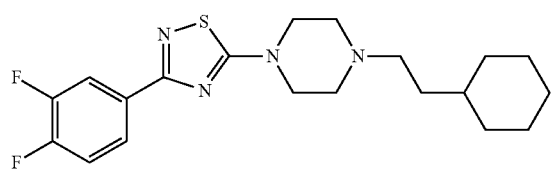 [SMILES: Fc1ccc(-c2nsc(N3CCN(CCC4CCCCC4)CC3)n2)cc1F]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(3,4-difluorophenyl)-5-(piperazin-1-yl)-1,2,4-thiadiazole dihydrochloride and (2-bromoethyl)cyclohexane. MS (m/e): 393.2 (MH$^+$).

Example 154

1-(2-Cyclohexyl-ethyl)-4-[3-(3-fluoro-phenyl)[1,2,4]thiadiazol-5-yl]-piperazine

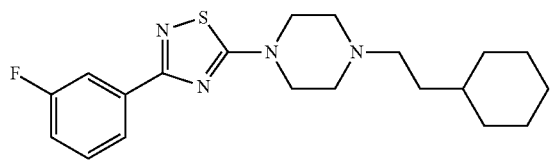 [SMILES: Fc1cccc(-c2nsc(N3CCN(CCC4CCCCC4)CC3)n2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3-Fluoro-phenyl)-[1,2,4]thiadiazol-5-yl]-piperazine dihydrochloride and (2-bromoethyl)cyclohexane. MS (m/e): 375.3 (MH$^+$).

Example 155

5-(4-(3-phenylpropyl)piperazin-1-yl)-3-(p-tolyl)-1,2,4-thiadiazole

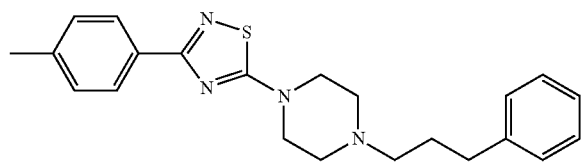 [SMILES: Cc1ccc(-c2nsc(N3CCN(CCCc4ccccc4)CC3)n2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 1-(3-p-Tolyl-[1,2,4]thiadiazol-5-yl)-piperazine and (3-bromopropyl)benzene.

Example 156

5-(4-(3,4-difluorophenethyl)piperazin-1-yl)-3-(3-fluorophenyl)-1,2,4-thiadiazole

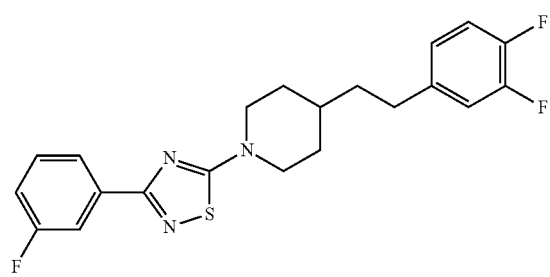 [SMILES: Fc1cccc(-c2nsc(N3CCC(CCc4ccc(F)c(F)c4)CC3)n2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 3-(3-fluorophenyl)-5-(piperazin-1-yl)-1,2,4-thiadiazole and 4-(2-bromoethyl)-1,2-difluorobenzene.

Example 157

3-(4-chloropyridin-2-yl)-5-(4-(3,4-difluorophenethyl)piperazin-1-yl)-1,2,4-thiadiazole

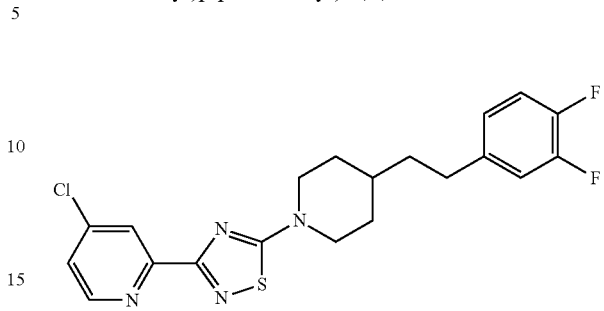

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 4-(2-bromoethyl)-1,2-difluorobenzene.

Example 158

3-(3,4-difluorophenyl)-5-(4-(3-(trifluoromethyl)phenethyl)piperazin-1-yl)-1,2,4-thiadiazole

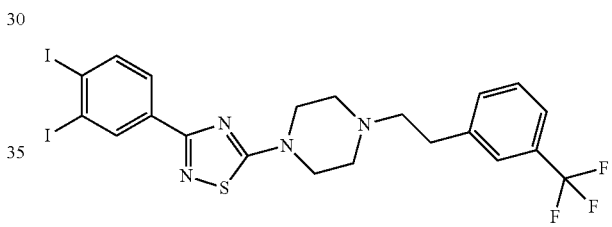

In analogy to the procedure described for the synthesis of 1-(2-Methyl-benzyl)-4-(3-p-tolyl-[1,2,4]thiadiazol-5-yl)-piperazine (example 6) the title compound was prepared from 1-[3-(3,4-Difluoro-phenyl)-[1,2,4]thiadiazol-5-yl]-piperazine dihydro chloride and 1-(2-bromoethyl)-3-(trifluoromethyl)benzene.

Example 159

3-(4-chloropyridin-2-yl)-5-(4-(3-(trifluoromethyl)phenethyl)piperazin-1-yl)-1,2,4-thiadiazole

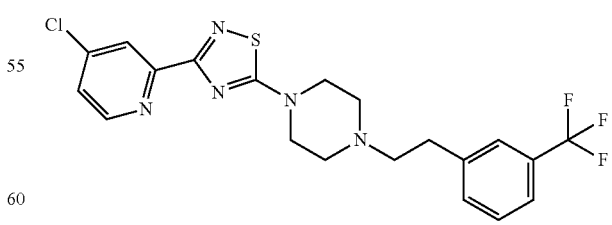

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 4-Chloro-2-(5-chloro-[1,2,4]thiadiazol-3-yl)-pyridine and 1-(2-bromoethyl)-3-(trifluoromethyl)benzene.

Example 160

3-(5-chloropyridin-3-yl)-5-(4-(3,4-difluorophenethyl)piperazin-1-yl)-1,2,4-thiadiazole

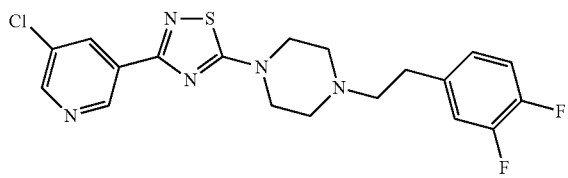 [SMILES: Fc1ccc(CCN2CCN(c3nc(-c4cncc(Cl)c4)ns3)CC2)cc1F]

In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 3-Chloro-5-(5-chloro-[1,2,4]thiadiazol-3-yl)-pyridine and 4-(2-bromoethyl)-1,2-difluorobenzene.

Example 161

3-(4-chlorophenyl)-5-(4-(2-cyclohexylethyl)piperazin-1-yl)-1,2,4-thiadiazole

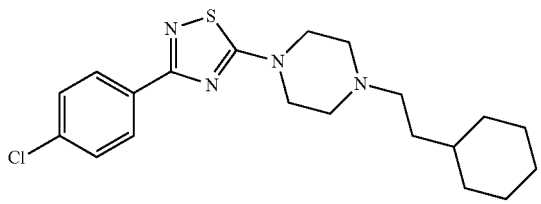 [SMILES: Clc1ccc(-c2nsc(N3CCN(CCC4CCCCC4)CC3)n2)cc1]

In analogy to the procedure described for the synthesis of 1-(2-Methyl-benzyl)-4-(3-p-tolyl-[1,2,4]thiadiazol-5-yl)-piperazine (example 6) the title compound was prepared from 5-chloro-3-(4-chlorophenyl)-1,2,4-thiadiazole and (2-bromoethyl)cyclohexane.

Example 162

3-(3-chlorophenyl)-5-(4-(2-cyclohexylethyl)piperazin-1-yl)-1,2,4-thiadiazole

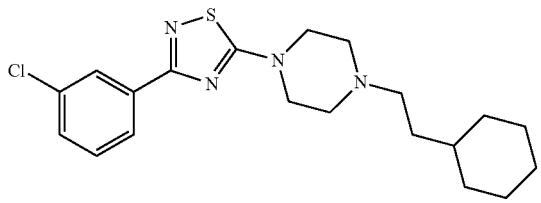 [SMILES: Clc1cccc(-c2nsc(N3CCN(CCC4CCCCC4)CC3)n2)c1]

In analogy to the procedure described for the synthesis of 1-(2-Methyl-benzyl)-4-(3-p-tolyl-[1,2,4]thiadiazol-5-yl)-piperazine (example 6) the title compound was prepared from 5-chloro-3-(3-chlorophenyl)-1,2,4-thiadiazole and (2-bromoethyl)cyclohexane.

Example 168

3-(2-chloropyridin-4-yl)-5-(4-(2-(2-methoxypyridin-4-yl)ethyl)piperazin-1-yl)-1,2,4-thiadiazole

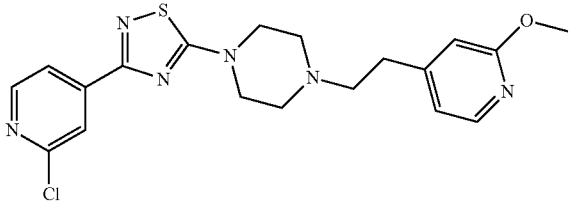 [SMILES: COc1cc(CCN2CCN(c3nc(-c4ccnc(Cl)c4)ns3)CC2)ccn1]

a) 5-chloro-3-(2-chloropyridin-4-yl)-1,2,4-thiadiazole

In analogy to the procedure described for the synthesis of 4-(5-Chloro-[1,2,4]thiadiazol-3-yl)-pyridine (Example 20, step a) the title compound was prepared from 2-chloroisonicotinimidamide.

b) 3-(2-chloropyridin-4-yl)-5-(4-(2-(2-methoxypyridin-4-yl)ethyl)piperazin-1-yl)-1,2,4-thiadiazole In analogy to the procedure described for the synthesis of 1-Benzo[1,3]dioxol-5-ylmethyl-4-(3-p-tolyl-[1,2,4]thiadiazol-5-yl)-piperazine (Example 2) the title compound was prepared from 5-chloro-3-(2-chloropyridin-4-yl)-1,2,4-thiadiazole and 1-(2-(2-methoxypyridin-4-yl)ethyl)piperazine trihydrochloride.

Example 169

5-(4-(4-chlorophenethyl)piperazin-1-yl)-3-(2-chloropyridin-4-yl)-1,2,4-thiadiazole

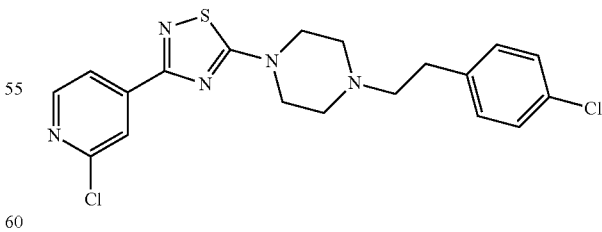

In analogy to the procedure described for the synthesis of 3-(2-chloropyridin-4-yl)-5-(4-(2-(2-methoxypyridin-4-yl)ethyl)piperazin-1-yl)-1,2,4-thiadiazole (Example 168), the tile compound was prepared from 5-chloro-3-(2-chloropyridin-4-yl)-1,2,4-thiadiazole and 1-(2-bromoethyl)-4-chlorobenzene.

Example 170

3-(2-chloropyridin-4-yl)-5-(4-phenethylpiperazin-1-yl)-1,2,4-thiadiazole

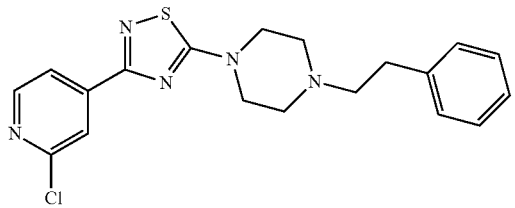 [SMILES: Clc1cc(-c2nsc(N3CCN(CCc4ccccc4)CC3)n2)ccn1]

In analogy to the procedure described for the synthesis of 3-(2-chloropyridin-4-yl)-5-(4-(2-(2-methoxypyridin-4-yl)ethyl)piperazin-1-yl)-1,2,4-thiadiazole (Example 168), the tile compound was prepared from 5-chloro-3-(2-chloropyridin-4-yl)-1,2,4-thiadiazole and (2-bromoethyl)benzene.

Example 171

3-(2-methylpyridin-4-yl)-5-(4-phenethylpiperazin-1-yl)-1,2,4-thiadiazole

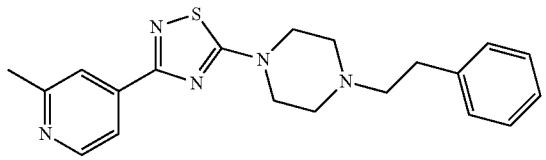 [SMILES: Cc1cc(-c2nsc(N3CCN(CCc4ccccc4)CC3)n2)ccn1]

In analogy to the procedure described for the synthesis of 3-(2-chloropyridin-4-yl)-5-(4-(2-(2-methoxypyridin-4-yl)ethyl)piperazin-1-yl)-1,2,4-thiadiazole (Example 168), the tile compound was prepared from 5-chloro-3-(2-chloropyridin-4-yl)-1,2,4-thiadiazole and (2-bromo ethyl)benzene.

Example 172

5-(4-(2-(2-methoxypyridin-4-yl)ethyl)piperazin-1-yl)-3-(2-methylpyridin-4-yl)-1,2,4-thiadiazole

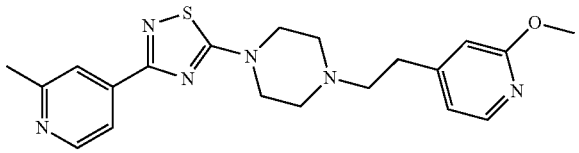

In analogy to the procedure described for the synthesis of 3-(2-chloropyridin-4-yl)-5-(4-(2-(2-methoxypyridin-4-yl)ethyl)piperazin-1-yl)-1,2,4-thiadiazole (Example 168), the tile compound was prepared from 5-chloro-3-(2-chloropyridin-4-yl)-1,2,4-thiadiazole and 1-(2-(2-methoxypyridin-4-yl)ethyl)piperazine trihydrochloride.

The compounds of formula IA or I and their pharmaceutically usable addition salts possess valuable pharmacological properties. Specifically, it has been found that the compounds of the present invention are useful for treating certain neurological disorders characterized by dysfunction of TAU protein, which diseases comprise Alzheimer's disease, Pick's disease, corticobasal degeneration, progressive supranuclear palsy, frontotemporal dementia and parkinsonism (linked to chromosome 17, FTDP-17). The compounds were investigated in accordance with the test given hereinafter.

Construction of a TAU Gene Over-Expressing Cell Line

A TAU expression plasmid was constructed by sub-cloning the cDNA encoding for human TAU-P301L protein, wherein proline at position 301 is substituted by a leucine residue, into mammalian expression vector pcDNA3.1 resulting in the plasmid pcDNA3.1-TAUP301L. Plasmids pcDNA3.1 and pcDNA3.1-TAU P301L were transfected into human neuroblastoma cells (BE-M17; ATCC No. CRL-2267™) using lipofectamine reagent and subsequently, independent clonal cell lines with the plasmids stably integrated into the genome were selected by antibiotic resistance selection (Geneticin (G418)), resulting in cell lines M17.pcDNA3 and M17_3TAUP301L. Expression of the TAUP301L gene in the M17_3TAUP301L cells was confirmed by Western blot analysis.

Use of TAU Expressing Cells as a Model of Neuronal Degeneration

The expression of TAU P301L in M17_3TAU(P301L) cells was found to confer increased toxicity relative to control cells expressing no TAU after 7 days of cell differentiation using retinoic acid (RA). Differentiation of the cells with RA leads to phosphorylation and subsequent aggregation of TAU, inducing a tauopathy in these cells. Cytotoxicity of cells was measured by quantification of lactate dehydrogenase (LDH) levels. In dead cells LDH is leaked out of the cells into the medium due to a loss of plasma-membrane integrity.

Briefly, 3 days preceding the experiment pre-cultures of M17.pcDNA3 and M17_3TAU(P301L) cells were prepared, starting from a stock culture, at a density of 50.000-100.000 cells/cm2 in detection medium (Optimem Reduced Serum without phenol red (Gibco, Cat. 31985-047) supplemented with 1% fetal calf serum (FCS), 1 mM sodium pyruvate, 1× non-essential amino acids (NEAA), 500 µg/ml G418 and 0.5× antibiotic/antimycotic (ABAM)). At the day of the experiment these precultures were diluted to ~0, 1.106 cells/ml in detection medium without FCS and 60 µL of this suspension is dispensed per well into a 96-well microtiter plate. After 3 hours of incubation at 37° C./5% CO2 an equal volume of detection medium containing 2.5 µM RA was added and subsequently incubated for 7 days at 37° C./5% $CO_2$. After 7 days, LDH activity was determined using the Promega Cytotox 96 Non-Radioactive cytotoxicity assay (Cat. G1780), according the manufacturer's instructions. Cytotoxicity is measured as the ratio of LDH increase in the supernatant divided by the LDH increase in the total cell suspension (sum of the LDH measured in cells and supernatant). FIG. 1 shows toxicity after 7 days of differentiation with retinoic acid in M17_3TAU(P301L) cells compared to M17.pcDNA3 cells. Toxicity is clearly higher in the M17_3TAU(P301L) cells demonstrating that it is specifically provoked by the presence of the mutant TAU P301 protein.

Use of the Neuroblastoma Tauopathy Model to Screen Compounds

The M17_3TAU(P301L) cell line makes it possible to assess the ability of novel compounds to inhibit TAU-induced cytotoxicity. Active inhibitors of Tauopathy in these cells were found to inhibit cytotoxicity or LDH increase in the medium of M17_3TAU(P301L) cells treated as described in Example above. Compounds were tested for their ability to hamper TAU-induced toxicity at different concentrations, ranging from low non-effective concentrations to high potent concentrations. Afterwards, the dose-dependent inhibition curve was used to calculate their $EC_{50}$ (Table 1).

Although the pharmacological properties of the compounds disclosed in this invention vary with structural change, active compounds most particularly possess $EC_{50}$ in a cell-based assay in a range from about 0.0001 to 1.0 μM.

The tested compounds show a $EC_{50}$ value (μM) as shown in the table below.

| Example | $EC_{50}$ (μM) |
| --- | --- |
| 2 | 0.5870 |
| 3 | 0.9874 |
| 4 | 0.1152 |
| 5 | 0.3963 |
| 6 | 0.2776 |
| 12 | 0.2685 |
| 13 | 0.2148 |
| 14 | 0.0048 |
| 15 | 0.0214 |
| 16 | 0.0653 |
| 17 | 0.0008 |
| 18 | 0.3672 |
| 19 | 0.0020 |
| 20 | 0.1740 |
| 21 | 0.0095 |
| 22 | 0.0042 |
| 23 | 0.0019 |
| 24 | 0.0007 |
| 25 | 0.0077 |
| 26 | 0.0049 |
| 27 | 0.0167 |
| 28 | 0.0452 |
| 29 | 0.0013 |
| 30 | 0.1469 |
| 31 | 0.0211 |
| 32 | 0.3682 |
| 33 | 0.1578 |
| 34 | 0.0014 |
| 35 | 0.0035 |
| 36 | 0.1189 |
| 37 | 0.0029 |
| 38 | 0.2112 |
| 39 | 0.0435 |
| 40 | 0.0141 |
| 41 | 0.0007 |
| 42 | 0.0003 |
| 43 | 0.0033 |
| 44 | 0.0023 |
| 45 | 0.0007 |
| 46 | 0.0312 |
| 47 | 0.0004 |
| 48 | 0.0006 |
| 49 | 0.0496 |
| 50 | 0.1688 |
| 51 | 0.1519 |
| 52 | 0.3270 |
| 53 | 0.0126 |
| 54 | 0.0161 |
| 55 | 0.0042 |
| 56 | 0.0055 |
| 57 | 0.0145 |
| 58 | 0.0022 |
| 59 | 0.0750 |
| 60 | 0.0412 |
| 61 | 0.0444 |
| 62 | 0.0687 |
| 63 | 0.0074 |
| 64 | 0.0098 |
| 65 | 0.0599 |
| 66 | 0.0015 |
| 67 | 0.0010 |
| 68 | 0.8992 |
| 69 | 0.0437 |
| 70 | 0.1945 |
| 71 | 0.4291 |
| 72 | 0.0943 |
| 73 | 0.0009 |
| 75 | 0.0134 |
| 76 | 0.0408 |
| 77 | 0.2611 |
| 78 | 0.0021 |
| 79 | 0.0028 |
| 80 | 0.0027 |
| 81 | 0.0006 |
| 82 | 0.0040 |
| 83 | 0.0095 |
| 84 | 0.0007 |
| 85 | 0.0031 |
| 86 | 0.0089 |
| 87 | 0.0131 |
| 88 | 0.1206 |
| 89 | 0.0016 |
| 90 | 0.0068 |
| 91 | 0.0009 |
| 92 | 0.0433 |
| 93 | 0.0009 |
| 94 | 0.0095 |
| 95 | 0.0031 |
| 96 | 0.0281 |
| 97 | 0.0513 |
| 98 | 0.0806 |
| 99 | 0.2714 |
| 100 | 0.0043 |
| 101 | 0.0032 |
| 102 | 0.0009 |
| 103 | 0.0034 |
| 104 | 0.0112 |
| 105 | 0.0021 |
| 106 | 0.0030 |
| 107 | 0.0722 |
| 108 | 0.0079 |
| 109 | 0.0030 |
| 110 | 0.0178 |
| 111 | 0.0031 |
| 112 | 0.0567 |
| 113 | 0.0171 |
| 114 | 0.0079 |
| 115 | 0.0023 |
| 116 | 0.0141 |
| 117 | 0.0058 |
| 118 | 0.1808 |
| 119 | 0.0250 |
| 120 | 0.0161 |
| 121 | 0.0346 |
| 122 | 0.0425 |
| 123 | 0.0946 |
| 124 | 0.4584 |
| 125 | 0.0030 |
| 126 | 0.0070 |
| 127 | 0.1092 |
| 128 | 0.1100 |
| 129 | 0.0923 |
| 130 | 0.0009 |
| 131 | 0.0013 |
| 132 | 0.0033 |
| 133 | 0.0014 |
| 134 | 0.0378 |
| 135 | 0.0045 |
| 136 | 0.0062 |
| 137 | 0.0062 |
| 138 | 0.0182 |
| 139 | 0.0472 |
| 140 | 0.0726 |
| 141 | 0.1983 |
| 142 | 0.0037 |
| 143 | 0.1427 |
| 144 | 0.6022 |

-continued

| Example | EC$_{50}$ (µM) |
|---|---|
| 145 | 0.4615 |
| 146 | 0.0601 |
| 147 | 0.1761 |
| 148 | 0.0675 |
| 149 | 0.0030 |
| 150 | 0.1853 |
| 151 | 0.0082 |
| 152 | 0.2150 |
| 153 | 0.0059 |
| 154 | 0.0170 |
| 155 | 0.9765 |
| 156 | 0.0119 |
| 157 | 0.0290 |
| 158 | 0.9984 |
| 159 | 0.1192 |
| 160 | 0.0004 |
| 161 | 0.0396 |
| 162 | 0.0033 |
| 163 | 0.0130 |
| 164 | 0.0034 |
| 165 | 0.0011 |
| 166 | 0.0007 |
| 167 | 0.0059 |
| 168 | 0.0015 |
| 169 | 0.0104 |
| 170 | 0.0007 |
| 171 | 0.0024 |
| 172 | 0.0144 |
| 173 | 0.0029 |
| 174 | 0.0126 |
| 175 | 0.0134 |
| 176 | 0.0195 |
| 177 | 0.0010 |
| 178 | 0.0132 |
| 179 | 0.0034 |
| 180 | 0.1294 |
| 181 | 0.0316 |
| 182 | 0.1917 |
| 183 | 0.1518 |

The compounds of formula IA or I and the pharmaceutically acceptable salts of the compounds of formula IA or I can be used as medicaments, e.g. in the form of pharmaceutical preparations. The pharmaceutical preparations can be administered orally, e.g. in the form of tablets, coated tablets, dragés, hard and soft gelatine capsules, solutions, emulsions or suspensions. The administration can, however, also be effected rectally, e.g. in the form of suppositories, or parenterally, e.g. in the form of injection solutions.

The compounds of formula IA or I can be processed with pharmaceutically inert, inorganic or organic carriers for the production of pharmaceutical preparations. Lactose, corn starch or derivatives thereof; talc, stearic acids or its salts and the like can be used, for example, as such carriers for tablets, coated tablets, dragés and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula IA or I or a pharmaceutically acceptable salt thereof and a therapeutically inert carrier are also an object of the present invention, as is a process for their production, which comprises bringing one or more compounds of formula IA or I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of Alzheimer's disease, Pick's disease, corticobasal degeneration, progressive supranuclear palsy, frontotemporal dementia and parkinsonism (linked to chromosome 17, FTDP-17).

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:
1. A compound of formula IA

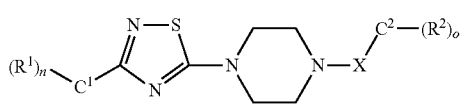

R1 is hydrogen; lower alkyl; lower alkyl substituted by halogen; halogen; lower alkoxy; lower alkoxy substituted by halogen; or cyano;
R2 is hydrogen; lower alkyl; lower alkyl substituted by halogen; halogen; lower alkoxy; or is lower alkoxy substituted by halogen;
C1 is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl;
C2 is phenyl; benzo[1,3]dioxol; pyridine-2-yl; pyridine-3-yl; pyridine-4-yl; thiophen-2-yl; pyrazine-2-yl; pyridazin-4-yl; pyrimidin-5-yl; piperidin-lyl; tetrahydro-2H-pyran-4-yl; or cycloalkyl;
X is —CH$_2$—; —CH$_2$—CHR—; —CH$_2$—CH$_2$—CH$_2$; —CH$_2$C(O)—; —CHR'—CH$_2$—;

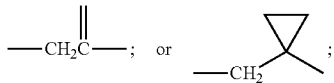

R is hydrogen; hydroxyl; halogen or lower alkyl;
R' is lower alkyl;
n is 1 or 2; if n is 2, R1 may be independently selected from each other;
o is 1 or 2; if o is 2, R2 may be independently selected from each other;
or a pharmaceutically active salt thereof; to a stereoisomeric form, including an individual diastereoisomer or enantiomer of the compound of formula IA as well as to a racemic or non-racemic mixture thereof.

2. A compound of formula IA according to claim 1, wherein C1 is selected from: phenyl; pyridine-2-yl; pyridine-3-yl; pyridine-4-yl; pyrazine-2-yl; pyridazin-4-yl; or pyrimidin-5-yl.

3. A compound of formula IA, according to claim 2, wherein C2 is selected from: phenyl; pyridine-2-yl; pyridine-3-yl; pyridine-4-yl; pyrazine-2-yl; tetrahydro-2H-pyran-4-yl; or cycloalkyl.

4. A compound of formula IA according to claim 3, wherein C1 and C2 are both phenyl.

5. A compound of formula IA according to claim 4, selected from the group consisting of:
1-(2,4-Dichloro-benzyl)-4-(3-p-tolyl-[1,2,4]thiadiazol-5-yl)-piperazine
1-Phenethyl-4-(3-p-tolyl-[1,2,4]thiadiazol-5-yl)-piperazine
1-[2-(3,4-Dichloro-phenyl)-ethyl]-4-(3-p-tolyl-[1,2,4]thiadiazol-5-yl)-piperazine
1-(2-Methyl-benzyl)-4-(3-p-tolyl-[1,2,4]thiadiazol-5-yl)-piperazine
1-[3-(4-Chloro-phenyl)-[1,2,4]thiadiazol-5-yl]-4-(2-methyl-benzyl)-piperazine
1-[3-(3-Methoxy-phenyl)-[1,2,4]thiadiazol-5-yl]-4-(2-methyl-benzyl)-piperazine
1-[3-(4-Chloro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(3-methoxy-phenyl)-[1,2,4]thiadiazol-5-yl]-piperazine
1-[2-(3-Methoxy-phenyl)-ethyl]-4-(3-p-tolyl-[1,2,4]thiadiazol-5-yl)-piperazine
1-[3-(4-Chloro-phenyl)-[1,2,4]thiadiazol-5-yl]-4-[2-(4-methoxy-phenyl)-ethyl]-piperazine
1-[2-(4-Methoxy-phenyl)-ethyl]-4-[3-(3-methoxy-phenyl)-[1,2,4]thiadiazol-5-yl]-piperazine
1-[2-(4-Methoxy-phenyl)-ethyl]-4-(3-p-tolyl-[1,2,4]thiadiazol-5-yl)-piperazine
1-[3-(4-Chloro-phenyl)-[1,2,4]thiadiazol-5-yl]-4-[2-(3-fluoro-phenyl)-ethyl]-piperazine
1-[2-(3-Chloro-phenyl)-ethyl]-4-[3-(4-chloro-phenyl)-[1,2,4]thiadiazol-5-yl]-piperazine
1-[3-(4-Chloro-phenyl)-[1,2,4]thiadiazol-5-yl]-4-(2-m-tolyl-ethyl)-piperazine
1-[3-(4-Chloro-phenyl)-[1,2,4]thiadiazol-5-yl]-4-[2-(4-fluoro-phenyl)-ethyl]-piperazine
1-[2-(4-Chloro-phenyl)-ethyl]-4-[3-(4-chloro-phenyl)-[1,2,4]thiadiazol-5-yl]-piperazine
1-[3-(4-Chloro-phenyl)-[1,2,4]thiadiazol-5-yl]-4-(2-p-tolyl-ethyl)-piperazine
1-[3-(4-Chloro-phenyl)-[1,2,4]thiadiazol-5-yl]-4-[2-(2-methoxy-phenyl)-ethyl]-piperazine
1-[3-(4-Chloro-phenyl)-[1,2,4]thiadiazol-5-yl]-4-[2-(2-fluoro-phenyl)-ethyl]-piperazine
1-[2-(2-Chloro-phenyl)-ethyl]-4-[3-(4-chloro-phenyl)-[1,2,4]thiadiazol-5-yl]-piperazine
1-[3-(3,5-Dichloro-phenyl)-[1,2,4]thiadiazol-5-yl]-4-[2-(3-methoxy-phenyl)-ethyl]-piperazine
1-[3-(4-Chloro-phenyl)-[1,2,4]thiadiazol-5-yl]-4-[3-(3-methoxy-phenyl)-propyl]-piperazine
1-[3-(4-Fluoro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(2-methoxy-phenyl)-[1,2,4]thiadiazol-5-yl]-piperazine
1-[2-(3-Methoxy-phenyl)-ethyl]-4-[3-(4-trifluoromethoxy-phenyl)-[1,2,4]thiadiazol-5-yl]-piperazine
1-[2-(4-Methoxy-phenyl)-ethyl]-4-[3-(4-trifluoromethoxy-phenyl)-[1,2,4]thiadiazol-5-yl]-piperazine
1-[3-(4-Chloro-phenyl)-[1,2,4]thiadiazol-5-yl]-4-[2-(3-trifluoromethoxy-phenyl)-ethyl]-piperazine
1-[3-(4-Chloro-phenyl)-[1,2,4]thiadiazol-5-yl]-4-[3-(2-methoxy-phenyl)-propyl]-piperazine
1-[2-(4-Methoxy-phenyl)-ethyl]-4-[3-(4-methoxy-phenyl)-[1,2,4]thiadiazol-5-yl]-piperazine
1-[3-(3-Chloro-phenyl)-[1,2,4]thiadiazol-5-yl]-4-[2-(4-methoxy-phenyl)-ethyl]-piperazine
1-[2-(4-Methoxy-phenyl)-ethyl]-4-[3-(2-methoxy-phenyl)-[1,2,4]thiadiazol-5-yl]-piperazine
1-[3-(3,5-Dichloro-phenyl)-[1,2,4]thiadiazol-5-yl]-4-[2-(4-methoxy-phenyl)-ethyl]-piperazine
1-[3-(4-Fluoro-phenyl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(3-methoxy-phenyl)-ethyl]-piperazine
1-[2-(3-Methoxy-phenyl)-ethyl]-4-[3-(4-methoxy-phenyl)-[1,2,4]thiadiazol-5-yl]-piperazine
1-[3-(4-Chloro-phenyl)-[1,2,4]thiadiazol-5-yl]-4-[2-(4-ethoxy-phenyl)-ethyl]-piperazine
1-[3-(4-Chloro-phenyl)-[1,2,4]thiadiazol-5-yl]-4-[2-(3-isopropoxy-phenyl)-ethyl]-piperazine
1-[3-(4-Chloro-phenyl)-[1,2,4]thiadiazol-5-yl]-4-[3-(4-methoxy-phenyl)-propyl]-piperazine 2-{4-[3-(4-Chloro-phenyl)-[1,2,4]thiadiazol-5-yl]-piperazin-1-yl}-1-(4-methoxy-phenyl)-ethanone
2-{4-[3-(4-Chloro-phenyl)-[1,2,4]thiadiazol-5-yl]-piperazin-1-yl}-1-(4-methoxy-phenyl)-ethanol
1-[3-(4-Chloro-2-fluoro-phenyl)-[1,2,4]thiadiazol-5-yl]-4-[2-(3-methoxy-phenyl)-ethyl]-piperazine
1-[3-(4-Chloro-2-fluoro-phenyl)-[1,2,4]thiadiazol-5-yl]-4-[2-(4-methoxy-phenyl)-ethyl]-piperazine
1-[3-(2-Chloro-phenyl)-[1,2,4]thiadiazol-5-yl]-4-[2-(3-methoxy-phenyl)-ethyl]-piperazine
1-[3-(2-Chloro-phenyl)-[1,2,4]thiadiazol-5-yl]-4-[2-(4-methoxy-phenyl)-ethyl]-piperazine
1-[3-(4-Chloro-phenyl)-[1,2,4]thiadiazol-5-yl]-4-[2-(4-methoxy-phenyl)-allyl]-piperazine
2-{4-[3-(4-Chloro-phenyl)-[1,2,4]thiadiazol-5-yl]-piperazin-1-yl}-1-(3-methoxy-phenyl)-ethanone
2-{4-[3-(4-Chloro-phenyl)-[1,2,4]thiadiazol-5-yl]-piperazin-1-yl}-1-(3-methoxy-phenyl)-ethanol
2-{4-[3-(4-Chloro-phenyl)-[1,2,4]thiadiazol-5-yl]-piperazin-1-yl}-1-(3-fluoro-phenyl)-ethanone
2-{4-[3-(4-Chloro-phenyl)-[1,2,4]thiadiazol-5-yl]-piperazin-1-yl}-1-(3-fluoro-phenyl)-ethanol
1-[3-(4-Chloro-phenyl)-[1,2,4]thiadiazol-5-yl]-4-[2-fluoro-2-(4-methoxy-phenyl)-ethyl]-piperazine
1-[3-(4-Chloro-phenyl)-[1,2,4]thiadiazol-5-yl]-4-[2-fluoro-2-(3-methoxy-phenyl)-ethyl]-piperazine
1-[3-(4-Fluoro-2-methoxy-phenyl)-[1,2,4]thiadiazol-5-yl]-4-[2-(3-methoxy-phenyl)-ethyl]-piperazine
1-[3-(4-Fluoro-2-methoxy-phenyl)-[1,2,4]thiadiazol-5-yl]-4-[2-(4-methoxy-phenyl)-ethyl]-piperazine
1-[1-(4-Chloro-phenyl)-cyclopropylmethyl-4-[3-(4-chloro-phenyl)-[1,2,4]thiadiazol-5-yl]-piperazine
1-[3-(4-Chloro-phenyl)-[1,2,4]thiadiazol-5-yl]-4-[2-(3-difluoromethoxy-phenyl)-ethyl]-piperazine
1-[3-(4-Chloro-phenyl)-[1,2,4]thiadiazol-5-yl]-4-[2-(4-difluoromethoxy-phenyl)-ethyl]-piperazine
1-[3-(4-Chloro-phenyl)-[1,2,4]thiadiazol-5-yl]-4-[2-(4-isopropoxy-phenyl)-ethyl]-piperazine
1-[3-(4-Chloro-phenyl)-[1,2,4]thiadiazol-5-yl]-4-[2-(4-methoxy-phenyl)-propyl]-piperazine
1-[3-(4-Chloro-phenyl)-[1,2,4]thiadiazol-5-yl]-4-[2-(4-methoxy-phenyl)-1-methyl-ethyl]-piperazine
4-(5-{4-[2-(4-Methoxy-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(3-fluoro-4-methoxy-phenyl)-ethyl]-piperazine
3-(5-{4-[2-(4-Methoxy-phenyl)-ethyl]-piperazin-1-yl}-[1,2,4]thiadiazol-3-yl)-benzonitrile
1-[3-(3-Chloro-phenyl)-[1,2,4]thiadiazol-5-yl]-4-phenethyl-piperazine
1-[3-(3-Fluoro-phenyl)-[1,2,4]thiadiazol-5-yl]-4-phenethyl-piperazine
1-[3-(3-Fluoro-phenyl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(4-fluoro-phenyl)-ethyl]-piperazine
1-[2-(4-Fluoro-phenyl)-ethyl]-4-[3-(3-fluoro-phenyl)-[1,2,4]thiadiazol-5-yl]-piperazine
1-[2-(4-Chloro-phenyl)-ethyl]-4-[3-(3-chloro-phenyl)-[1,2,4]thiadiazol-5-yl]-piperazine
1-[2-(4-Chloro-phenyl)-ethyl]-4-[3-(3-fluoro-phenyl)-[1,2,4]thiadiazol-5-yl]-piperazine
1-[3-(3-Chloro-phenyl)-[1,2,4]thiadiazol-5-yl]-4-(2-methyl-benzyl)-piperazine
1-[3-(3-Fluoro-phenyl)-[1,2,4]thiadiazol-5-yl]-4-(2-methyl-benzyl)-piperazine
1-[3-(3,4-Difluoro-phenyl)-[1,2,4]thiadiazol-5-yl]-4-phenethyl-piperazine
1-[3-(3,4-Difluoro-phenyl)-[1,2,4]thiadiazol-5-yl]-4-[2-(4-methoxy-phenyl)-ethyl]-piperazine
1-[3-(3,4-Difluoro-phenyl)-[1,2,4]thiadiazol-5-yl]-4-[2-(4-fluoro-phenyl)-ethyl]-piperazine
1-[2-(4-Chloro-phenyl)-ethyl]-4-[3-(3,4-difluoro-phenyl)-[1,2,4]thiadiazol-5-yl]-piperazine
1-[3-(3,4-Difluoro-phenyl)-[1,2,4]thiadiazol-5-yl]-4-(2-methyl-benzyl)-piperazine
4-[5-(4-Phenethyl-piperazin-1-yl)-[1,2,4]thiadiazol-3-yl]-benzonitrile
3-[5-(4-Phenethyl-piperazin-1-yl)-[1,2,4]thiadiazol-3-yl]-benzonitrile
4-(5-{4-[2-(4-Fluoro-phenyl)-ethyl]-piperazin-1-yl}-[1,2,4]thiadiazol-3-yl)-benzonitrile
3-(5-{4-[2-(4-Fluoro-phenyl)-ethyl]-piperazin-1-yl}-[1,2,4]thiadiazol-3-yl)-benzonitrile
4-(5-{4-[2-(4-Chloro-phenyl)-ethyl]-piperazin-1-yl}-[1,2,4]thiadiazol-3-yl)-benzonitrile
3-(5-{4-[2-(4-Chloro-phenyl)-ethyl]-piperazin-1-yl}-[1,2,4]thiadiazol-3-yl)-benzonitrile
4-{5-[4-(2-Methyl-benzyl)-piperazin-1-yl]-[1,2,4]thiadiazol-3-yl}-benzonitrile
3-{5-[4-(2-Methyl-benzyl)-piperazin-1-yl]-[1,2,4]thiadiazol-3-yl}-benzonitrile
1-[3-(4-Chloro-phenyl)-[1,2,4]thiadiazol-5-yl]-4-[2-(3,4-difluoro-phenyl)-ethyl]-piperazine
1-[3-(3-Chloro-phenyl)-[1,2,4]thiadiazol-5-yl]-4-[2-(3,4-difluoro-phenyl)-ethyl]-piperazine
1-[2-(3,4-Difluoro-phenyl)-ethyl]-4-[3-(3,4-difluoro-phenyl)-[1,2,4]thiadiazol-5-yl]-piperazine
3-(5-{4-[2-(3,4-Difluoro-phenyl)-ethyl]-piperazin-1-yl}-[1,2,4]thiadiazol-3-yl)-benzonitrile
4-(5-{4-[2-(3,4-Difluoro-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(3-trifluoromethyl-phenyl)-ethyl]-piperazine
1-[3-(3-Fluoro-phenyl)-[1,2,4]thiadiazol-5-yl]-4-[2-(3-trifluoromethyl-phenyl)-ethyl]-piperazine
1-[3-(3-Chloro-phenyl)-[1,2,4]thiadiazol-5-yl]-4-[2-(3-trifluoromethyl-phenyl)-ethyl]-piperazine
4-(5-{4-[2-(3-Trifluoromethyl-phenyl)-ethyl]-piperazin-1-yl}-[1,2,4]thiadiazol-3-yl)-benzonitrile
1-[3-(4-Chloro-phenyl)-[1,2,4]thiadiazol-5-yl]-4-[2-(4-trifluoromethyl-phenyl)-ethyl]-piperazine
1-[3-(3-Chloro-phenyl)-[1,2,4]thiadiazol-5-yl]-4-[2-(4-trifluoromethyl-phenyl)-ethyl]-piperazine
1-[3-(3,4-Difluoro-phenyl)-[1,2,4]thiadiazol-5-yl]-4-[2-(4-trifluoromethyl-phenyl)-ethyl]-piperazine
4-(5-{4-[2-(4-Trifluoromethyl-phenyl)-ethyl]-piperazin-1-yl}-[1,2,4]thiadiazol-3-yl)-benzonitrile
5-(4-(3-phenylpropyl)piperazin-1-yl)-3-(p-tolyl)-1,2,4-thiadiazole
5-(4-(3,4-difluorophenethyl)piperazin-1-yl)-3-(3-fluorophenyl)-1,2,4-thiadiazole and
3-(3,4-difluorophenyl)-5-(4-(3-(trifluoromethyl)phenethyl)piperazin-1-yl)-1,2,4-thiadiazole.

6. A compound of formula IA according to claim 1, wherein at least one of C1 or C2 is pyridine-2-yl, pyridine-3-yl or pyridine-4-yl.

7. A compound of formula IA according to claim 6, selected from the group consisting of:
1-[2-(3-Methoxy-phenyl)-ethyl]-4-(3-pyridin-4-yl-[1,2,4]thiadiazol-5-yl)-piperazine
1-[2-(3-Methoxy-phenyl)-ethyl]-4-[3-(6-trifluoromethyl-pyridin-3-yl)-[1,2,4]thiadiazol-5-yl]-piperazine 1-[2-(4-Methoxy-phenyl)-ethyl]-4-[3-(6-trifluoromethyl-pyridin-3-yl)-[1,2,4]thiadiazol-5-yl]-piperazine
1-[2-(4-Methoxy-phenyl)-ethyl]-4-(3-pyridin-4-yl-[1,2,4]thiadiazol-5-yl)-piperazine
1-[3-(4-Chloro-phenyl)-[1,2,4]thiadiazol-5-yl]-4-[2-(2-methoxy-pyridin-4-yl)-ethyl]-piperazine
1-[3-(4-Chloro-phenyl)-[1,2,4]thiadiazol-5-yl]-4-[2-(6-methoxy-pyridin-3-yl)-ethyl]-piperazine
1-[3-(3-Chloro-phenyl)-[1,2,4]thiadiazol-5-yl]-4-[2-(2-methoxy-pyridin-4-yl)-ethyl]-piperazine
1-[3-(3-Fluoro-phenyl)-[1,2,4]thiadiazol-5-yl]-4-[2-(2-methoxy-pyridin-4-yl)-ethyl]-piperazine
1-[3-(5-Chloro-pyridin-3-yl)-[1,2,4]thiadiazol-5-yl]-4-[2-(4-methoxy-phenyl)-ethyl]-piperazine
1-[3-(3-Chloro-phenyl)-[1,2,4]thiadiazol-5-yl]-4-[2-(6-methoxy-pyridin-3-yl)-ethyl]-piperazine
1-[3-(6-Methyl-pyridin-3-yl)-[1,2,4]thiadiazol-5-yl]-4-phenethyl-piperazine
1-[2-(4-Methoxy-phenyl)-ethyl]-4-[3-(6-methyl-pyridin-3-yl)-[1,2,4]thiadiazol-5-yl]-piperazine
1-[2-(4-Fluoro-phenyl)-ethyl]-4-[3-(6-methyl-pyridin-3-yl)-[1,2,4]thiadiazol-5-yl]-piperazine
1-[2-(2-Methoxy-pyridin-4-yl)-ethyl]-4-[3-(6-methyl-pyridin-3-yl)-[1,2,4]thiadiazol-5-yl]-piperazine
1-[2-(4-Chloro-phenyl)-ethyl]-4-[3-(6-methyl-pyridin-3-yl)-[1,2,4]thiadiazol-5-yl]-piperazine
1-[3-(3-Fluoro-phenyl)-[1,2,4]thiadiazol-5-yl]-4-[2-(6-methoxy-pyridin-3-yl)-ethyl]-piperazine
1-[3-(3,4-Difluoro-phenyl)-[1,2,4]thiadiazol-5-yl]-4-[2-(6-methoxy-pyridin-3-yl)-ethyl]-piperazine
1-[3-(3,4-Difluoro-phenyl)-[1,2,4]thiadiazol-5-yl]-4-[2-(2-methoxy-pyridin-4-yl)-ethyl]-piperazine
4-(5-{4-[2-(6-Methoxy-pyridin-3-yl)-ethyl]-piperazin-1-yl}-[1,2,4]thiadiazol-3-yl)-benzonitrile
3-(5-{4-[2-(6-Methoxy-pyridin-3-yl)-ethyl]-piperazin-1-yl}-[1,2,4]thiadiazol-3-yl)-benzonitrile
4-(5-{4-[2-(2-Methoxy-pyridin-4-yl)-ethyl]-piperazin-1-yl}-[1,2,4]thiadiazol-3-yl)-benzonitrile
3-(5-{4-[2-(2-Methoxy-pyridin-4-yl)-ethyl]-piperazin-1-yl}-[1,2,4]thiadiazol-3-yl)-benzonitrile
1-[3-(4-Chloro-pyridin-2-yl)-[1,2,4]thiadiazol-5-yl]-4-phenethyl-piperazine
1-[3-(5-Chloro-pyridin-2-yl)-[1,2,4]thiadiazol-5-yl]-4-phenethyl-piperazine
1-[3-(4-Chloro-pyridin-2-yl)-[1,2,4]thiadiazol-5-yl]-4-[2-(4-fluoro-phenyl)-ethyl]-piperazine
1-[2-(4-Chloro-phenyl)-ethyl]-4-[3-(4-chloro-pyridin-2-yl)-[1,2,4]thiadiazol-5-yl]-piperazine
1-[2-(4-Chloro-phenyl)-ethyl]-4-[3-(5-chloro-pyridin-2-yl)-[1,2,4]thiadiazol-5-yl]-piperazine
1-[3-(4-Chloro-pyridin-2-yl)-[1,2,4]thiadiazol-5-yl]-4-[2-(4-methoxy-phenyl)-ethyl]-piperazine
1-[3-(5-Chloro-pyridin-2-yl)-[1,2,4]thiadiazol-5-yl]-4-[2-(4-methoxy-phenyl)-ethyl]-piperazine
1-[3-(4-Chloro-pyridin-2-yl)-[1,2,4]thiadiazol-5-yl]-4-[2-(2-methoxy-pyridin-4-yl)-ethyl]-piperazine
1-[3-(4-Chloro-pyridin-2-yl)-[1,2,4]thiadiazol-5-yl]-4-(2-methyl-benzyl)-piperazine
1-[3-(5-Chloro-pyridin-2-yl)-[1,2,4]thiadiazol-5-yl]-4-(2-methyl-benzyl)-piperazine
1-[3-(5-Chloro-pyridin-3-yl)-[1,2,4]thiadiazol-5-yl]-4-phenethyl-piperazine
1-[3-(5-Chloro-pyridin-3-yl)-[1,2,4]thiadiazol-5-yl]-4-[2-(4-fluoro-phenyl)-ethyl]-piperazine
1-[2-(4-Chloro-phenyl)-ethyl]-4-[3-(5-chloro-pyridin-3-yl)-[1,2,4]thiadiazol-5-yl]-piperazine
1-[3-(5-Chloro-pyridin-3-yl)-[1,2,4]thiadiazol-5-yl]-4-[2-(2-methoxy-pyridin-4-yl)-ethyl]-piperazine
1-[3-(5-Chloro-pyridin-2-yl)-[1,2,4]thiadiazol-5-yl]-4-[2-(3,4-difluoro-phenyl)-ethyl]-piperazine
1-[2-(3,4-Difluoro-phenyl)-ethyl]-4-[3-(6-methyl-pyridin-3-yl)-[1,2,4]thiadiazol-5-yl]piperazine
1-[3-(5-Chloro-pyridin-3-yl)-[1,2,4]thiadiazol-5-yl]-4-[2-(3-trifluoromethyl-phenyl)-ethyl]-piperazine
1-(2-Methyl-benzyl)-4-[3-(6-methyl-pyridin-3-yl)-[1,2,4]thiadiazol-5-yl]-piperazine
1-[3-(5-Chloro-pyridin-3-yl)-[1,2,4]thiadiazol-5-yl]-4-(2-methyl-benzyl)-piperazine
1-[3-(5-Chloro-pyridin-3-yl)-[1,2,4]thiadiazol-5-yl]-4-[2-(4-trifluoromethyl-phenyl)-ethyl]-piperazine
3-(4-chloropyridin-2-yl)-5-(4-(3,4-difluorophenethyl)piperazin-1-yl)-1,2,4-thiadiazole
3-(4-chloropyridin-2-yl)-5-(4-(3-(trifluoromethyl)phenethyl)piperazin-1-yl)-1,2,4-thiadiazole
3-(5-chloropyridin-3-yl)-5-(4-(3,4-difluorophenethyl)piperazin-1-yl)-1,2,4-thiadiazole
3-(2-chloropyridin-4-yl)-5-(4-(2-(2-methoxypyridin-4-yl)ethyl)piperazin-1-yl)-1,2,4-thiadiazole
5-(4-(4-chlorophenethyl)piperazin-1-yl)-3-(2-chloropyridin-4-yl)-1,2,4-thiadiazole
3-(2-chloropyridin-4-yl)-5-(4-phenethylpiperazin-1-yl)-1,2,4-thiadiazole
3-(2-methylpyridin-4-yl)-5-(4-phenethylpiperazin-1-yl)-1,2,4-thiadiazole and
5-(4-(2-(2-methoxypyridin-4-yl)ethyl)piperazin-1-yl)-3-(2-methylpyridin-4-yl)-1,2,4-thiadiazole.

8. A compound of formula IA according to claim 1, wherein C2 is cycloalkyl.

9. A compound of formula IA according to claim 8, selected from the group consisting of:
1-(2-Cyclohexyl-ethyl)-4-[3-(3,4-difluoro-phenyl)-[1,2,4]thiadiazol-5-yl]-piperazine
1-(2-Cyclohexyl-ethyl)-4-[3-(3-fluoro-phenyl)-[1,2,4]thiadiazol-5-yl]-piperazine
3-(4-chlorophenyl)-5-(4-(2-cyclohexylethyl)piperazin-1-yl)-1,2,4-thiadiazole and
3-(3-chlorophenyl)-5-(4-(2-cyclohexylethyl)piperazin-1-yl)-1,2,4-thiadiazole.

10. A compound of formula IA according to claim 1, wherein C2 is piperidin-1-yl.

11. A compound of formula IA according to claim 10, which compound is 3-(5-chloropyridin-3-yl)-5-(4-(2-(piperidin-1-yl)ethyl)piperazin-1-yl)-1,2,4-thiadiazole.

12. A compound of formula IA according to claim 1, wherein C2 is tetrahydro-2H-pyran-4-yl.

13. A compound of formula IA according to claim 12, selected from the group consisting of:
3-(3,4-difluorophenyl)-5-(4-(2-(tetrahydro-2H-pyran-4-yl)ethyl)piperazin-1-yl)-1,2,4-thiadiazole
3-(3-chlorophenyl)-5-(4-(2-(tetrahydro-2H-pyran-4-yl)ethyl)piperazin-1-yl)-1,2,4-thiadiazole
3-(5-chloropyridin-3-yl)-5-(4-(2-(tetrahydro-2H-pyran-4-yl)ethyl)piperazin-1-yl)-1,2,4-thiadiazole and
3-(4-chlorophenyl)-5-(4-(2-(tetrahydro-2H-pyran-4-yl)ethyl)piperazin-1-yl)-1,2,4-thiadiazole.

14. A compound of formula IA according to claim 1, wherein C1 is pyridazin-4-yl.

15. A compound of formula IA according to claim 14, selected from the group consisting of:
3-(6-methylpyridazin-4-yl)-5-(4-phenethylpiperazin-1-yl)-1,2,4-thiadiazole
5-(4-(4-fluorophenethyl)piperazin-1-yl)-3-(6-methylpyridazin-4-yl)-1,2,4-thiadiazole 5-(4-(3,4-difluorophenethyl)piperazin-1-yl)-3-(6-methylpyridazin-4-yl)-1,2,4-thiadiazole 5-(4-(2-(2-methoxypyridin-4-yl)ethyl)piperazin-1-yl)-3-(6-methylpyridazin-4-yl)-1,2,4-thiadiazole and 5-(4-(4-methoxyphenethyl)piperazin-1-yl)-3-(6-methylpyridazin-4-yl)-1,2,4-thiadiazole.

16. A compound of formula IA according to claim 1, wherein C1 is pyrimidin-5-yl.

17. A compound of formula IA according to claim 16, selected from the group consisting of:

3-(2-methylpyrimidin-5-yl)-5-(4-phenethylpiperazin-1-yl)-1,2,4-thiadiazole 5-(4-(4-methoxyphenethyl)piperazin-1-yl)-3-(2-methylpyrimidin-5-yl)-1,2,4-thiadiazole 5-(4-(4-chlorophenethyl)piperazin-1-yl)-3-(2-methylpyrimidin-5-yl)-1,2,4-thiadiazole 5-(4-(4-fluorophenethyl)piperazin-1-yl)-3-(2-methylpyrimidin-5-yl)-1,2,4-thiadiazole 5-(4-(3,4-difluorophenethyl)piperazin-1-yl)-3-(2-methylpyrimidin-5-yl)-1,2,4-thiadiazole and 5-(4-(2-(2-methoxypyridin-4-yl)ethyl)piperazin-1-yl)-3-(2-methylpyrimidin-5-yl)-1,2,4-thiadiazole.

18. A process for preparation of compounds of formula IA according to claim 1, which process comprises coupling a compound of formula

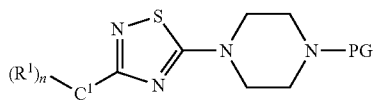
IVa with a compound of formula

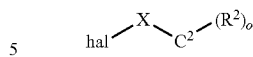

to give a compound of formula

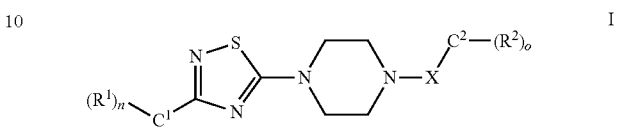
I wherein the definitions are as described in claim 1, wherein PG is hydrogen or a protecting group, and hal is a halogen or
if desired, converting the compounds obtained into pharmaceutically acceptable acid addition salts.

19. A compound manufactured according to a process of claim 18.

20. A pharmaceutical composition comprising the compound according to claim 1.

21. The pharmaceutical composition of claim 20 containing one or more compounds and pharmaceutically acceptable excipients.

22. A method of treating a disease selected from the group consisting of Alzheimer's disease, Pick's disease, corticobasal degeneration, progressive supranuclear palsy, frontotemporal dementia and parkinsonism (linked to chromosome 17, FTDP-17), comprising administering the pharmaceutical composition according to claim 21.

* * * * *